US012209129B2

(12) United States Patent
Vigna et al.

(10) Patent No.: US 12,209,129 B2
(45) Date of Patent: Jan. 28, 2025

(54) ANTI-MET FAB-FC FOR THE TREATMENT OF A TUMOR AND/OR METASTASIS

(71) Applicant: PIERRE FABRE MEDICAMENT, Lavaur (FR)

(72) Inventors: Elisa Vigna, Villarbasse (IT); Cristina Basilico, Pavarolo (IT); Tiziana Crepaldi, Turin (IT); Paolo Maria Comoglio, Arignano (IT)

(73) Assignee: PIERRE FABRE MEDICAMENT, Lavaur (FR)

( * ) Notice: Subject to any disclaimer, the term of this patent is extended or adjusted under 35 U.S.C. 154(b) by 855 days.

(21) Appl. No.: 17/283,482

(22) PCT Filed: Oct. 7, 2019

(86) PCT No.: PCT/EP2019/077116
§ 371 (c)(1),
(2) Date: Apr. 7, 2021

(87) PCT Pub. No.: WO2020/074459
PCT Pub. Date: Apr. 16, 2020

(65) Prior Publication Data
US 2021/0395372 A1 Dec. 23, 2021

(30) Foreign Application Priority Data

Oct. 9, 2018 (IT) .......................... 102018000009282

(51) Int. Cl.
| | | |
|---|---|---|
| *C07K 16/28* | (2006.01) | |
| *A61P 35/00* | (2006.01) | |
| *A61P 35/04* | (2006.01) | |
| *C07K 16/46* | (2006.01) | |
| *A61K 39/00* | (2006.01) | |

(52) U.S. Cl.
CPC .......... *C07K 16/2863* (2013.01); *A61P 35/00* (2018.01); *A61P 35/04* (2018.01); *C07K 16/462* (2013.01); *A61K 2039/505* (2013.01); *C07K 2317/14* (2013.01); *C07K 2317/21* (2013.01); *C07K 2317/24* (2013.01); *C07K 2317/33* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 2317/64; C07K 2317/50; C07K 16/2863
USPC ....................................................... 424/133.1
See application file for complete search history.

(56) References Cited

U.S. PATENT DOCUMENTS

2020/0316218 A1* 10/2020 Germeroth .............. A61P 29/00

FOREIGN PATENT DOCUMENTS

| BR | 102012006063 B1 * | 3/2023 |
|---|---|---|
| WO | 2005/063816 | 7/2005 |
| WO | 2013/033008 | 3/2013 |
| WO | 2014/108829 | 7/2014 |

OTHER PUBLICATIONS

Moritz et al (Electrophoresis 2017, 38, 769-785; Published online Mar. 2, 2017).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Martinelli et al (J Exp Clin Cancer Res Mar. 29, 2022;41(1):112).*
Martinelli et al (J Exp Clin Cancer Res May 24, 2022;41(1):180).*
International Search Report for PCT/EP2019/077116 mailed Mar. 2, 2020, 6 pages.
Written Opinion of the ISA for PCT/EP2019/077116 mailed Mar. 2, 2020, 6 pages.
G. Pacchiana et al., "Monovalency Unleashes the Full Therapeutic Potential of the DN-30 Anti-Met Antibody", *Journal of Biological Chemistry*, vol. 285, No. 46, Nov. 12, 2010, pp. 36149-36157.
Watts et al., "Activation of complement pathways by univalent antibody derivatives with intact Fc zones", *Molecular Immunology*, vol. 22, No. 7, Jul. 1, 1985, pp. 803-810.
Ha et al., "Immunoglobulin Fc Heterodimer Platform Technology: From Design to Applications in Therapeutic Antibodies and Proteins," Front. Immunol. 7, Article 394 (2016).
Comoglio et al., "Known and novel roles of the MET oncogene in cancer: a coherent approach to targeted therapy," Nat Rev Cancer 18(6): 341-358 (2018).
Aftimos et al., "A phase I, first-in-human study of argx-111, a monoclonal antibody targeting c-met in patients with solid tumors," Journal of Clinical Oncology 33(15_suppl1) (2015).
Yoh et al.,"A phase I dose-escalation study of LY2875358, a bivalent MET antibody, given as monotherapy or in combination with erlotinib or gefitinib in Japanese patients with advanced malignancies." Invest New Drugs 34(5):584-95 (2016) and Rosen et al., Clin Cancer Res. 23(8): 1910-1919 (2017).
Sakai et al., "A non-randomized, open-label, single-arm, Phase 2 study of emibetuzumab in Asian patients with MET diagnostic positive, advanced gastric cancer." Cancer Chemother Pharmacol. 80(6):1197-1207 (2017).

(Continued)

*Primary Examiner* — Lynn A Bristol
(74) *Attorney, Agent, or Firm* — Panitch Schwarze Belisario & Nadel LLP; Erin M. Dunston

(57) ABSTRACT

An anti-Met antibody fragment comprising a single antigen binding arm and an Fc region, wherein the antigen binding arm is defined by the variable regions having amino acid sequences as set forth in SEQ ID No.: 7, 8 and wherein the anti-Met antibody fragment is useful in the treatment of a tumor and/or metastasis.

10 Claims, 23 Drawing Sheets
Specification includes a Sequence Listing.

(56) References Cited

OTHER PUBLICATIONS

Jin et al., "MetMAb, the One-Armed 5D5 Anti-c-Met Antibody, Inhibits Orthotopic Pancreatic Tumor Growth and Improves Survival." Cancer Research 68(11): 4360-4368 (2008).

Martens et al., "A Novel One-Armed Anti-c-Met Antibody Inhibits Glioblastoma Growth In vivo." Clin Cancer Research 12(20): 6144-6152 (2006).

Merchant et al., "Monovalent antibody design and mechanism of action of onartuzumab, a MET antagonist with anti-tumor activity as a therapeutic agent." PNAS E2987-E2996 (2013).

Kishi et al., "First-line onartuzumab plus erlotinib treatment for patients with METpositive and EGFR mutation-positive non-small-cell lung cancer." Cancer Treat Res Commun. 18:100113 (2018).

Rosen et al., "A First-in-Human Phase I Study of a Bivalent MET Antibody, Emibetuzumab (LY2875358), as Monotherapy and in Combination with Erlotinib in Advanced Cancer." Clin Cancer Res. 23(8): 1910-1919 (2017).

* cited by examiner

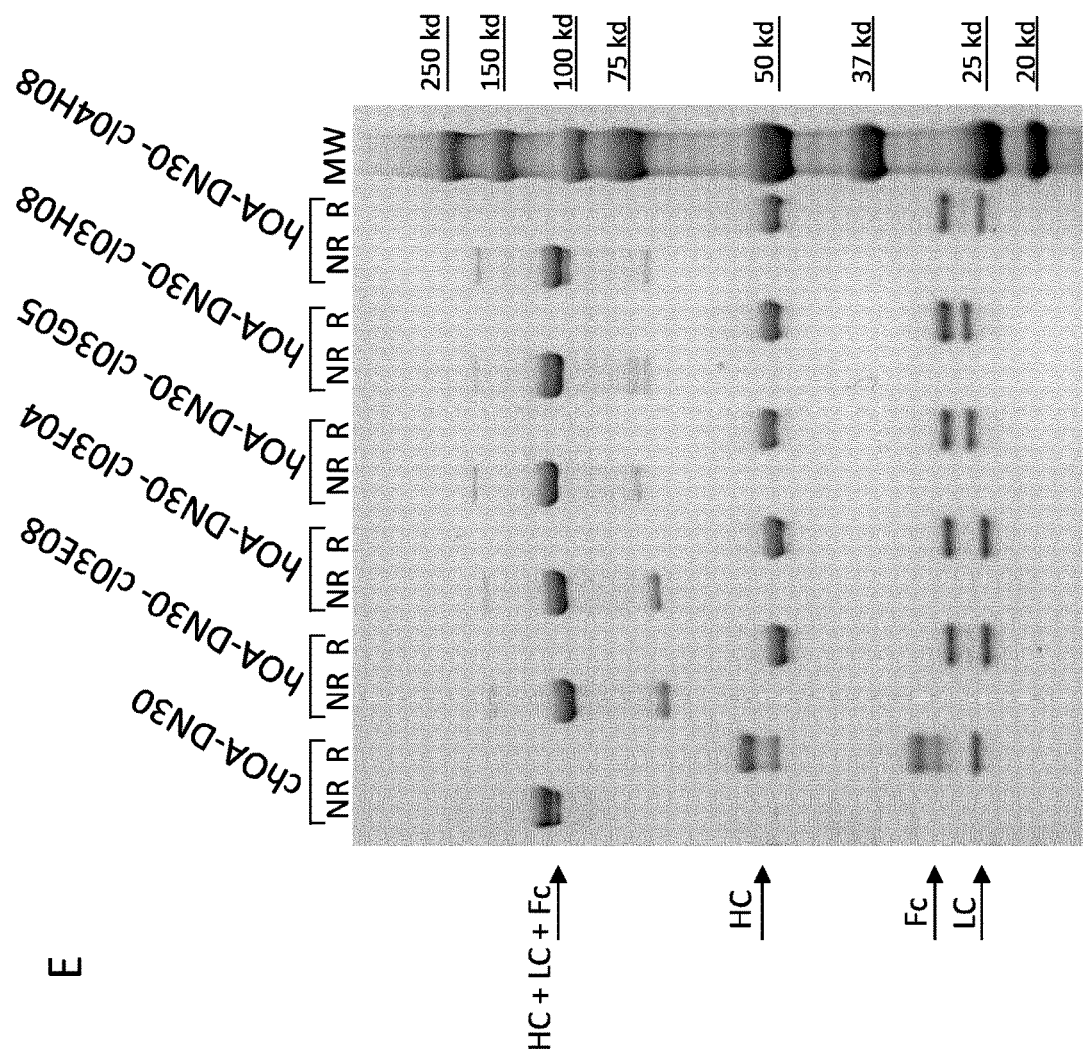
Fig. 1/cont

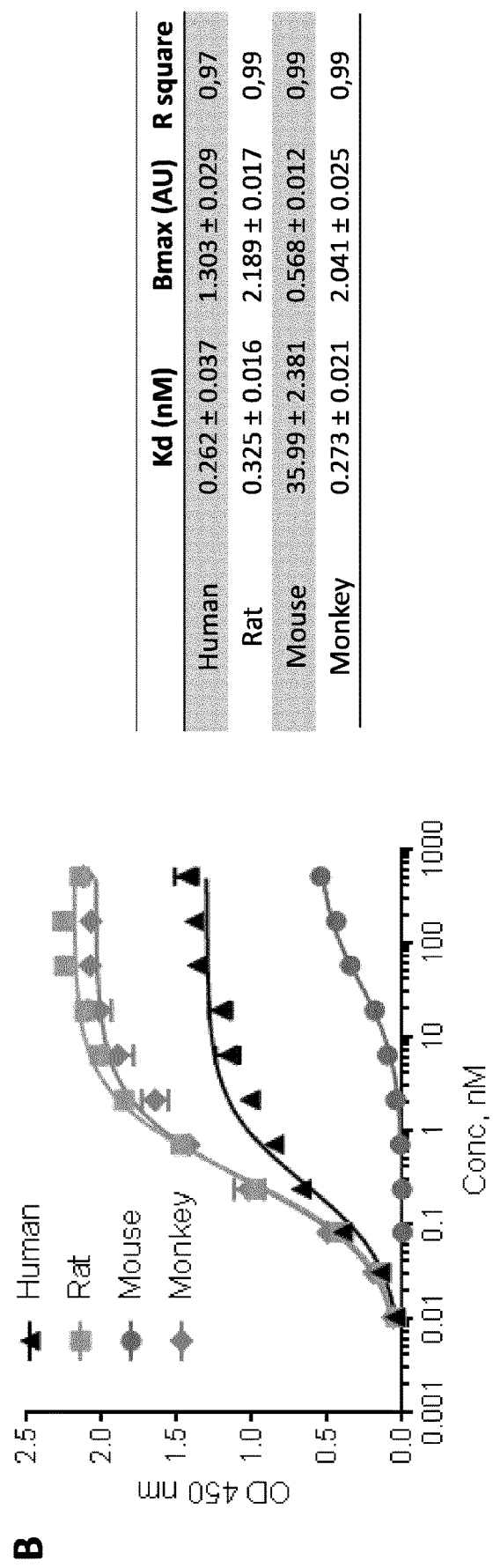
Fig. 2/cont

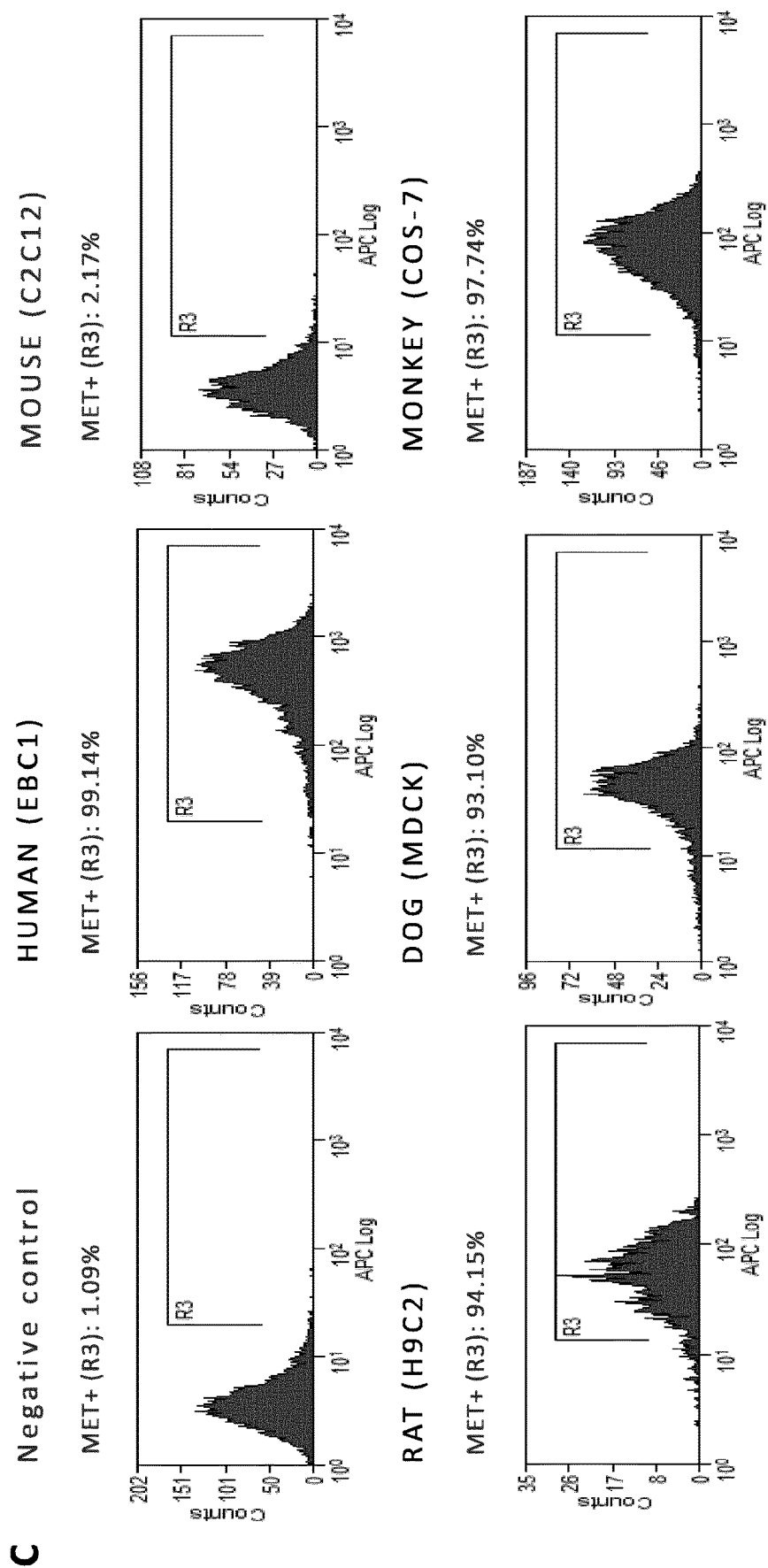
Fig. 2/cont

* N/A: Not applicable as data fitting is ambiguous

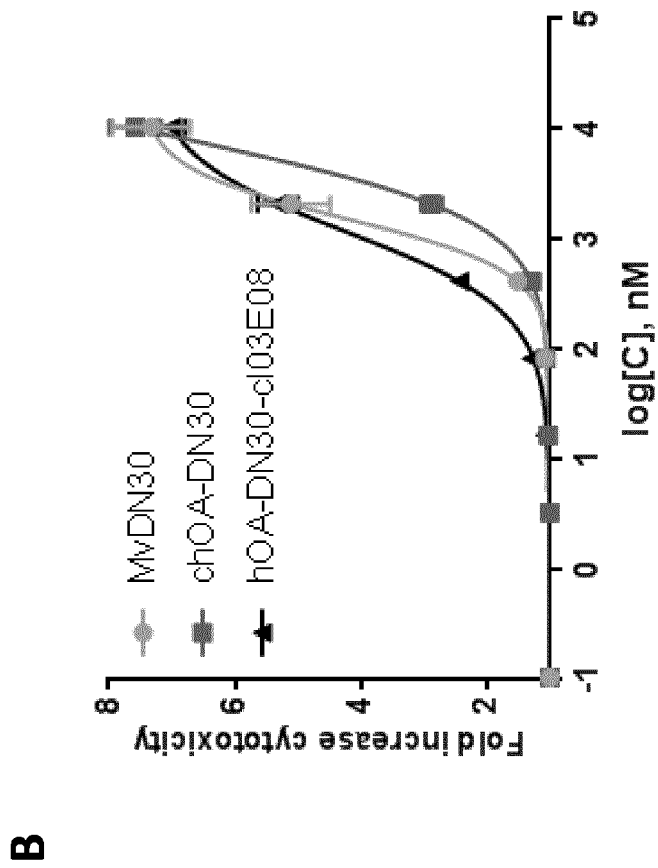
Fig. 7/cont

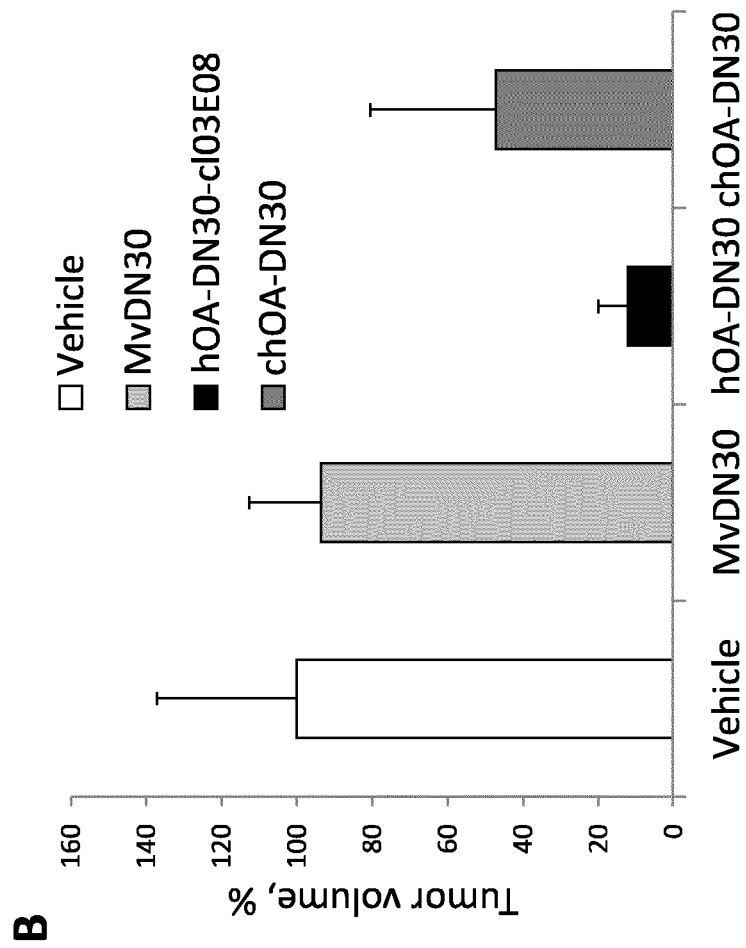
Fig. 12/cont

Seq. ID N°7: VL-c103E08 humanized

METDTILLWVLLLWVPGSTGDIVLTQSPDSLAVSLGQRATINCKASQSVDYDGGSYMSWFQQKPGQPPKLL
IYAASNLESGVPARFSGSGSGTDFTLTISSLQAEDVATYYCQQSYEDPLTFGGGTKVEIK

Seq. ID N°8: VH-c103E08 humanized

MGWSYIILFLVATATDGHSQVQLQQSGAEVKKPGASVKLSCKASGYTFTSYWIHWVRQAPGQGLEWIGE**IN
PSSGRTNYNEKFKNRVTVTVDKSTSTAYMELSSLTSEDSAVYYCASRGY**WGQGTTLTVSS

Seq. ID N°9: human CL

RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC

Seq. ID N°10: human CH1

ASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKV

Fig. 14

Seq. ID N°11: First Fc (Knob mutation)

EPKSCDKTHTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRDELTKN
QVSLWCLVKGFYPSDIAVEWESNGQPENNYKTTPPVLDSDGSFFLYSKLTVDKSRWQQGNVFSCSVMHEALHN
HYTQKSLSLSPGK

Seq. ID N°12: Second Fc (Hole mutations)

MGWSYIILFLVATATDGHSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQPREPQ
VYTLPPSRDELTKNQVSLSCAVKGFYPSDIAVEWESNGQPENNYKTTPPVLDSDGSFFLVSKLTVDKSRWQQG
NVFSCSVMHEALHNHYTQKSLSLSPGK

Fig. 15

Seq. ID N°14: DecoyMet mutation K842E -TAGs

MKAPAVLAPGIILVLLFTLVQRSNGECKEALAKSEMNVNMKYQLPNFTAETPIQNVILHEHHIFLGATNYIYV
LNEEDLQKVAEYKTGPVLEHPDCFPCQDCSSKANLSGGVWKDNINMALVVDTYDDQLISCGSVNRGTCQRH
VFPHNHTADIQSEVHCIFSPQIEEPSQCPDCVVSALGAKVLSSVKDRFINFFVGNTINSSYFPDHPLHSISV
RRLKETKDGFMFLTDQSYIDVLPEFRDSYPIKYVHAFESNNFIYFLTVQRETLDAQTFHTRIRFCSINSGL
HSYMEMPLECILTEKRKKRSTKKEVFNILQAAYVSKPGAQLARQIGASLNDDILFGVFAQSKPDSAEPMDRS
AMCAFPIKYVNDFFNKIVNKNNVRCLQHFYGPNHEHCFNRTLLRNSSGCEARRDEYRTEFTTALQRVDLFMG
QFSEVLLTSISTFIKGDLTIANLGTSEGRFMQVVVSRGPSTPHVNFLLDSHPVSPEVIVEHTLNQNGYTLV
ITGKKITKIPLNGLGCRHFQSCSQCLSAPPFVQCGWCHDKCVRSEECLSGTWTQQICLPAIYKVFPNSAPLE
GGTRLTICGWDFGFRRNNKFDLKKTRVLLGNESCTLTLSESTMNTLKCTVGPAMNKHFNMSIIISNGHGTTQ
YSTFSYVDPVITSISPKYGPMAGGTLLTLTGNYLNSGNSRHISIGGKTCTLKSVSNSILECYTPAQTISTEF
AVKLKIDLANRETSIFSYREDPIVYEIHPTKSFISGGSTITGVGKNLNSVSVPRMVINVHEAGRNFTVACQH
RSNSEICCTTPSLQQLNLQLPLKTKAFFMLDGILSKYFDLIYVHNPVFEPFEKPVMISMGNENVLEIKGND
IDPEAVKGEVLKVGNKSCENIHLHSEAVLCTVPNDLLKLNSELNIEWKQAISSTVLGKVIVQPDQNFTASGA
AWSHPQFEKGAAWSHPQFEKGAAHHHHHH

Fig. 16

Budapest Treaty for the Recognition of Deposit of Microorganisms for Patent purposes International form

| METIS PRECISION MEDICINE SB S.r.l.<br>Via Magenta 35<br>Torino<br>Italy | Duplicate<br>Declaration of viability<br>issued under Rule 10.2<br>By the Deposit International Authority<br>specified below |
|---|---|

| I. Depositor | II. Identification of the microorganism (hybridoma or cell line) |
|---|---|
| Metheresis Translational Research S.A.<br>Via alla Campagna, 2°<br>6900 Lugano (CH)<br><br>Dipart. Scienze Oncologiche Univ. di Torino<br>Strada Provinciale 142, Km 3.95<br>10060 Candiolo (TO)<br><br>New Owner – Assignee of Metheresis Translational Research S.A.<br><br>METIS PRECISION MEDICINE SB S.r.l.<br>Via Magenta 35<br>Torino<br>Italy | Accession number assigned by the Deposit International Authority:<br>PD 08003<br><br>Date of deposit or transfer:<br>16 April 2008 |

III. Declaration of viability

The viability of the microorganism identified under point II has been controlled on 6 May 2008. At that date, the above referenced microorganism resulted
√ viable
  not viable IV. Conditions for carrying out the test[1]

V. Deposit International Authority

| Name:<br>Centro di Biotecnologie Avanzate (CBA)<br>Interlab Cell Line Collection<br><br>Address:<br>L.go R. Benzi, 10<br>16132 GENOVA - ITALY | Signature of the Legal Representative of the Deposit International Authority or of an authorized officer:<br><br><br>Dr. Carlo Castelli<br>The liquidator |
|---|---|

[1] Fill in only if the information was requested and if the test result was negative
Form BP/9 (single page)

FIGURE 17

Budapest Treaty for the Recognition of Deposit of Microorganisms for Patent purposes International form

| | |
|---|---|
| Istituto per la Ricerca e la Cura del Cancro (IRCC)<br>Div. Oncologia Molecolare<br>Strada provinciale 142<br>10060 CANDIOLO (Torino) | Receipt of original deposit<br>Issued under Rule 7.1<br>By the Deposit International Authority specified below |

| |
|---|
| I. Identification of the microorganism (hybridoma or cell line) |
| Identifying reference provided by depositor:<br>DN-30      Accession number assigned by the Deposit International Authority: PD 05006 |
| II. Scientific description and/or proposed taxonomic designation |
| The identified hybridoma under point I. was accompanied by<br>√ a scientific description      a proposed taxonomic description |
| III. Receipt and acceptance |
| This Deposit International Authority accepts the hybridoma identified under point I., received on December 29, 2005 (date of original deposit) |
| IV. Receipt of requested conversion |
| The cell line identified under point I. has been received by this Deposit International Authority on      (date of original deposit)<br><br>A request of converting the original deposit in a deposit under the provisions of the Budapest Treaty has been received on      (date of request of conversion) |
| V. Deposit International Authority |

| | |
|---|---|
| Name:<br>Centro di Biotecnologie Avanzate (CBA)<br>Interlab Cell Line Collection<br><br>Address:<br>L.go R. Benzi, 10<br>16132 GENOVA - ITALY | Signature of the Legal Representative of the Deposit International Authority or of an authorized officer:<br><br><br>Dr. Paolo Rolleri<br>CBA President |

Form BP/4 (single page)

FIGURE 18

```
                             SEQUENCE LISTING

<160> NUMBER OF SEQ ID NOS: 43

<210> SEQ ID NO 1
   <211> LENGTH: 10
   <212> TYPE: PRT
   <213> ORGANISM: artificial
   <220> FEATURE:
   <223> OTHER INFORMATION: VL-CDR1

<400> SEQUENCE: 1

Gln Ser Val Asp Tyr Asp Gly Gly Ser Tyr
   1               5                   10

<210> SEQ ID NO 2
   <211> LENGTH: 3
   <212> TYPE: PRT
   <213> ORGANISM: artificial
   <220> FEATURE:
   <223> OTHER INFORMATION: VL-CDR2

<400> SEQUENCE: 2

Ala Ala Ser
   1

<210> SEQ ID NO 3
   <211> LENGTH: 9
   <212> TYPE: PRT
   <213> ORGANISM: artificial
   <220> FEATURE:
   <223> OTHER INFORMATION: VL-CDR3

<400> SEQUENCE: 3

Gln Gln Ser Tyr Glu Asp Pro Leu Thr
   1               5

<210> SEQ ID NO 4
   <211> LENGTH: 8
   <212> TYPE: PRT
   <213> ORGANISM: artificial
   <220> FEATURE:
   <223> OTHER INFORMATION: VH-CDR1

<400> SEQUENCE: 4

Gly Tyr Thr Phe Thr Ser Tyr Trp
   1               5

<210> SEQ ID NO 5
   <211> LENGTH: 8
   <212> TYPE: PRT
   <213> ORGANISM: artificial
   <220> FEATURE:
   <223> OTHER INFORMATION: VH-CDR2

<400> SEQUENCE: 5

Ile Asn Pro Ser Ser Gly Arg Thr
   1               5

<210> SEQ ID NO 6
```

```
<211> LENGTH: 5
<212> TYPE: PRT
<213> ORGANISM: artificial
<220> FEATURE:
<223> OTHER INFORMATION: VH-CDR3

<400> SEQUENCE: 6

Ala Ser Arg Gly Tyr
1               5

<210> SEQ ID NO 7
<211> LENGTH: 131
<212> TYPE: PRT
<213> ORGANISM: artificial
<220> FEATURE:
<223> OTHER INFORMATION: humanized VL-cl03E08

<400> SEQUENCE: 7

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Asp Ser Leu Ala
            20                  25                  30

Val Ser Leu Gly Gln Arg Ala Thr Ile Asn Cys Lys Ala Ser Gln Ser
        35                  40                  45

Val Asp Tyr Asp Gly Gly Ser Tyr Met Ser Trp Phe Gln Gln Lys Pro
    50                  55                  60

Gly Gln Pro Pro Lys Leu Leu Ile Tyr Ala Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Thr Ile Ser Ser Leu Gln Ala Glu Asp Val Ala Thr Tyr Tyr Cys
            100                 105                 110

Gln Gln Ser Tyr Glu Asp Pro Leu Thr Phe Gly Gly Gly Thr Lys Val
        115                 120                 125

Glu Ile Lys
    130

<210> SEQ ID NO 8
<211> LENGTH: 131
<212> TYPE: PRT
<213> ORGANISM: artificial
<220> FEATURE:
<223> OTHER INFORMATION: humanized VH-cl03E08

<400> SEQUENCE: 8

Met Gly Trp Ser Tyr Ile Ile Leu Phe Leu Val Ala Thr Ala Thr Asp
1               5                   10                  15

Gly His Ser Gln Val Gln Leu Gln Gln Ser Gly Ala Glu Val Lys Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Arg Gln Ala Pro Gly Gln Gly Leu
    50                  55                  60

Glu Trp Ile Gly Glu Ile Asn Pro Ser Ser Gly Arg Thr Asn Tyr Asn
65                  70                  75                  80

Glu Lys Phe Lys Asn Arg Val Thr Val Thr Val Asp Lys Ser Thr Ser
                85                  90                  95

Thr Ala Tyr Met Glu Leu Ser Ser Leu Thr Ser Glu Asp Ser Ala Val
            100                 105                 110
```

```
Tyr Tyr Cys Ala Ser Arg Gly Tyr Trp Gly Gln Gly Thr Thr Leu Thr
            115                 120                 125

Val Ser Ser
    130

<210> SEQ ID NO 9
<211> LENGTH: 107
<212> TYPE: PRT
<213> ORGANISM: Homo sapiens

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 98
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 11
<211> LENGTH: 232
<212> TYPE: PRT
<213> ORGANISM: artificial
<220> FEATURE:
<223> OTHER INFORMATION: First Fc (Knob mutation)

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
65                   70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 12
<211> LENGTH: 246
<212> TYPE: PRT
<213> ORGANISM: artificial
<220> FEATURE:
<223> OTHER INFORMATION: Second Fc (Hole mutations)

<400> SEQUENCE: 12

```
Met Gly Trp Ser Tyr Ile Ile Leu Phe Leu Val Ala Thr Ala Thr Asp
1               5                   10                  15

Gly His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160
```

-continued

```
Gln Val Ser Leu Ser Cys Ala Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Val Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 13
<211> LENGTH: 976
<212> TYPE: PRT
<213> ORGANISM: artificial
<220> FEATURE:
<223> OTHER INFORMATION: Decoy Met wt-TAGs

<400> SEQUENCE: 13

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270
```

```
Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
    355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
    435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
    515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
    595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
    675                 680                 685

His Ile Ser Ile Gly Gly Lys Thr Cys Thr Leu Lys Ser Val Ser Asn
```

```
                690             695             700
Ser Ile Leu Glu Cys Tyr Thr Pro Ala Gln Thr Ile Ser Thr Glu Phe
705             710             715             720

Ala Val Lys Leu Lys Ile Asp Leu Ala Asn Arg Glu Thr Ser Ile Phe
            725             730             735

Ser Tyr Arg Glu Asp Pro Ile Val Tyr Glu Ile His Pro Thr Lys Ser
            740             745             750

Phe Ile Ser Gly Gly Ser Thr Ile Thr Gly Val Gly Lys Asn Leu Asn
            755             760             765

Ser Val Ser Val Pro Arg Met Val Ile Asn Val His Glu Ala Gly Arg
    770             775             780

Asn Phe Thr Val Ala Cys Gln His Arg Ser Asn Ser Glu Ile Ile Cys
785             790             795             800

Cys Thr Thr Pro Ser Leu Gln Gln Leu Asn Leu Gln Leu Pro Leu Lys
            805             810             815

Thr Lys Ala Phe Phe Met Leu Asp Gly Ile Leu Ser Lys Tyr Phe Asp
            820             825             830

Leu Ile Tyr Val His Asn Pro Val Phe Lys Pro Phe Glu Lys Pro Val
            835             840             845

Met Ile Ser Met Gly Asn Glu Asn Val Leu Glu Ile Lys Gly Asn Asp
    850             855             860

Ile Asp Pro Glu Ala Val Lys Gly Glu Val Leu Lys Val Gly Asn Lys
865             870             875             880

Ser Cys Glu Asn Ile His Leu His Ser Glu Ala Val Leu Cys Thr Val
            885             890             895

Pro Asn Asp Leu Leu Lys Leu Asn Ser Glu Leu Asn Ile Glu Trp Lys
            900             905             910

Gln Ala Ile Ser Ser Thr Val Leu Gly Lys Val Ile Val Gln Pro Asp
            915             920             925

Gln Asn Phe Thr Ala Ser Gly Ala Ala Trp Ser His Pro Gln Phe Glu
            930             935             940

Lys Gly Ala Ala Trp Ser His Pro Gln Phe Glu Lys Gly Ala Ala Trp
945             950             955             960

Ser His Pro Gln Phe Glu Lys Gly Ala Ala His His His His His His
            965             970             975

<210> SEQ ID NO 14
<211> LENGTH: 976
<212> TYPE: PRT
<213> ORGANISM: artificial
<220> FEATURE:
<223> OTHER INFORMATION: Decoy Met mutation K842E-TAGs

<400> SEQUENCE: 14

Met Lys Ala Pro Ala Val Leu Ala Pro Gly Ile Leu Val Leu Leu Phe
1               5               10              15

Thr Leu Val Gln Arg Ser Asn Gly Glu Cys Lys Glu Ala Leu Ala Lys
            20              25              30

Ser Glu Met Asn Val Asn Met Lys Tyr Gln Leu Pro Asn Phe Thr Ala
            35              40              45

Glu Thr Pro Ile Gln Asn Val Ile Leu His Glu His His Ile Phe Leu
    50              55              60

Gly Ala Thr Asn Tyr Ile Tyr Val Leu Asn Glu Glu Asp Leu Gln Lys
65              70              75              80

Val Ala Glu Tyr Lys Thr Gly Pro Val Leu Glu His Pro Asp Cys Phe
```

```
                        85                  90                  95
Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
                115                 120                 125

Gln Leu Ile Ser Cys Gly Ser Val Asn Arg Gly Thr Cys Gln Arg His
                130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
                210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510
```

```
Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Glu Pro Phe Glu Lys Pro Val
        835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925
```

```
Gln Asn Phe Thr Ala Ser Gly Ala Ala Trp Ser His Pro Gln Phe Glu
        930                 935                 940

Lys Gly Ala Ala Trp Ser His Pro Gln Phe Glu Lys Gly Ala Ala Trp
945                 950                 955                 960

Ser His Pro Gln Phe Glu Lys Gly Ala Ala His His His His His His
                965                 970                 975
```

<210> SEQ ID NO 15
<211> LENGTH: 131
<212> TYPE: PRT
<213> ORGANISM: artificial
<220> FEATURE:
<223> OTHER INFORMATION: murine VL

<400> SEQUENCE: 15

```
Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
            100                 105                 110

Gln Gln Ser Tyr Glu Asp Pro Leu Thr Phe Gly Ala Gly Thr Lys Val
        115                 120                 125

Glu Ile Lys
    130
```

<210> SEQ ID NO 16
<211> LENGTH: 131
<212> TYPE: PRT
<213> ORGANISM: artificial
<220> FEATURE:
<223> OTHER INFORMATION: murine VH

<400> SEQUENCE: 16

```
Met Gly Trp Ser Tyr Ile Ile Leu Phe Leu Val Ala Thr Ala Thr Asp
1               5                   10                  15

Gly His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Lys Gln Arg Pro Gly Gln Gly Leu
50                  55                  60

Glu Trp Ile Gly Glu Ile Asn Pro Ser Ser Gly Arg Thr Asn Tyr Asn
65                  70                  75                  80

Glu Lys Phe Lys Asn Lys Val Thr Val Thr Val Asp Lys Ser Ser Thr
                85                  90                  95

Thr Ala Tyr Met Gln Leu Ser Asn Leu Thr Ser Glu Asp Ser Ala Val
            100                 105                 110

Tyr Tyr Cys Ala Ser Arg Gly Tyr Trp Gly Gln Gly Thr Thr Leu Thr
        115                 120                 125
```

Val Ser Ser
    130

<210> SEQ ID NO 17
<211> LENGTH: 131
<212> TYPE: PRT
<213> ORGANISM: artificial
<220> FEATURE:
<223> OTHER INFORMATION: humanized VL-cl03G05

<400> SEQUENCE: 17

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Glu Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
    50                  55                  60

Gly Gln Pro Pro Lys Leu Leu Ile Tyr Ala Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Asn Ile Ser Pro Leu Glu Ala Glu Asp Val Ala Val Tyr Tyr Cys
            100                 105                 110

Gln Gln Ser Tyr Glu Asp Pro Leu Thr Phe Gly Gly Gly Thr Lys Val
        115                 120                 125

Glu Ile Lys
    130

<210> SEQ ID NO 18
<211> LENGTH: 131
<212> TYPE: PRT
<213> ORGANISM: artificial
<220> FEATURE:
<223> OTHER INFORMATION: humanized VH-cl03G05

<400> SEQUENCE: 18

Met Gly Trp Ser Tyr Ile Ile Leu Phe Leu Val Ala Thr Ala Thr Asp
1               5                   10                  15

Gly His Ser Gln Val Gln Leu Val Gln Pro Gly Thr Glu Val Lys Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Arg Gln Ala Pro Gly Gln Gly Leu
    50                  55                  60

Glu Trp Met Gly Glu Ile Asn Pro Ser Ser Gly Arg Thr Asn Tyr Asn
65                  70                  75                  80

Glu Lys Phe Lys Asn Arg Val Thr Ile Thr Ala Asp Lys Ser Thr Ser
                85                  90                  95

Thr Ala Tyr Met Gln Leu Ser Ser Leu Arg Ser Glu Asp Thr Ala Val
            100                 105                 110

Tyr Tyr Cys Ala Ser Arg Gly Tyr Trp Gly Gln Gly Thr Thr Val Thr
        115                 120                 125

Val Ser Ser
    130

```
<210> SEQ ID NO 19
<211> LENGTH: 131
<212> TYPE: PRT
<213> ORGANISM: artificial
<220> FEATURE:
<223> OTHER INFORMATION: humanized VL-cl03F04

<400> SEQUENCE: 19

Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Ser
        35                  40                  45

Val Asp Tyr Asp Gly Ser Tyr Met Ser Trp Tyr Gln Gln Lys Pro
    50                  55                  60

Gly Gln Pro Pro Lys Leu Leu Ile Ser Ala Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile His Ser Leu Gln Ala Glu Asp Val Ala Val Tyr Tyr Cys
            100                 105                 110

Gln Gln Ser Tyr Glu Asp Pro Leu Thr Phe Gly Ala Gly Thr Lys Val
        115                 120                 125

Glu Ile Lys
    130

<210> SEQ ID NO 20
<211> LENGTH: 131
<212> TYPE: PRT
<213> ORGANISM: artificial
<220> FEATURE:
<223> OTHER INFORMATION: humanized VH-cl03F04

<400> SEQUENCE: 20

Met Gly Trp Ser Tyr Ile Ile Leu Phe Leu Val Ala Thr Ala Thr Asp
1               5                   10                  15

Gly His Ser Gln Val Gln Leu Gln Gln Pro Gly Ala Glu Val Lys Lys
            20                  25                  30

Pro Gly Ser Ser Val Lys Leu Ser Cys Lys Ala Ser Gly Tyr Thr Phe
        35                  40                  45

Thr Ser Tyr Trp Ile His Trp Val Lys Gln Ala Pro Gly Gln Gly Leu
    50                  55                  60

Glu Trp Ile Gly Glu Ile Asn Pro Ser Ser Gly Arg Thr Asn Tyr Asn
65                  70                  75                  80

Glu Lys Phe Lys Asn Lys Val Thr Ile Thr Val Asp Lys Ser Thr Ser
                85                  90                  95

Thr Ala Tyr Met Glu Leu Ser Asn Leu Arg Ser Glu Asp Ser Ala Val
            100                 105                 110

Tyr Tyr Cys Ala Ser Arg Gly Tyr Trp Gly Gln Gly Thr Thr Leu Thr
        115                 120                 125

Val Ser Ser
    130

<210> SEQ ID NO 21
<211> LENGTH: 131
<212> TYPE: PRT
<213> ORGANISM: artificial
<220> FEATURE:
```

<223> OTHER INFORMATION: humanized VL-cl03H08

<400> SEQUENCE: 21

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Glu Arg Ala Thr Ile Ser Cys Lys Ala Ser Gln Ser
        35                  40                  45

Val Asp Tyr Asp Gly Gly Ser Tyr Met Ser Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Asn Ile Ser Ser Val Gln Glu Glu Asp Val Ala Thr Tyr Tyr Cys
            100                 105                 110

Gln Gln Ser Tyr Glu Asp Pro Leu Thr Phe Gly Ala Gly Thr Lys Val
        115                 120                 125

Glu Ile Lys
    130

<210> SEQ ID NO 22
<211> LENGTH: 131
<212> TYPE: PRT
<213> ORGANISM: artificial
<220> FEATURE:
<223> OTHER INFORMATION: humanized VH-cl03H08

<400> SEQUENCE: 22

Met Gly Trp Ser Tyr Ile Ile Leu Phe Leu Val Ala Thr Ala Thr Asp
1               5                   10                  15

Gly His Ser Gln Val Gln Leu Val Gln Ser Gly Ala Glu Val Lys Lys
            20                  25                  30

Pro Gly Ser Ser Val Lys Leu Ser Cys Lys Ala Ser Gly Tyr Thr Phe
        35                  40                  45

Ser Ser Tyr Trp Ile His Trp Val Arg Gln Ala Pro Gly Gln Gly Leu
    50                  55                  60

Glu Trp Met Gly Glu Ile Asn Pro Ser Ser Gly Arg Thr Asn Tyr Asn
65                  70                  75                  80

Glu Lys Phe Lys Asn Arg Val Thr Ile Thr Ala Asp Lys Ser Thr Ser
                85                  90                  95

Thr Ala Tyr Met Glu Leu Ser Asn Leu Arg Ser Glu Asp Ser Ala Val
            100                 105                 110

Tyr Tyr Cys Ala Ser Arg Gly Tyr Trp Gly Gln Gly Thr Thr Leu Thr
        115                 120                 125

Val Ser Ser
    130

<210> SEQ ID NO 23
<211> LENGTH: 131
<212> TYPE: PRT
<213> ORGANISM: artificial
<220> FEATURE:
<223> OTHER INFORMATION: humanized VL-cl04H08

<400> SEQUENCE: 23

Met Glu Thr Asp Thr Ile Leu Leu Trp Val Leu Leu Leu Trp Val Pro

```
1               5                   10                  15
Gly Ser Thr Gly Asp Ile Val Leu Thr Gln Ser Pro Ala Ser Leu Ala
                20                  25                  30

Val Ser Leu Gly Glu Arg Ala Thr Ile Asn Cys Lys Ala Ser Gln Ser
                35                  40                  45

Val Asp Tyr Asp Gly Gly Ser Tyr Met Ser Trp Tyr Gln Gln Arg Pro
    50                  55                  60

Gly Gln Pro Pro Lys Leu Leu Ile Tyr Ala Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile His Ser Leu Gln Ala Glu Asp Val Ala Thr Tyr Tyr Cys
                100                 105                 110

Gln Gln Ser Tyr Glu Asp Pro Leu Thr Phe Gly Gly Gly Thr Lys Val
                115                 120                 125

Glu Ile Lys
    130

<210> SEQ ID NO 24
<211> LENGTH: 131
<212> TYPE: PRT
<213> ORGANISM: artificial
<220> FEATURE:
<223> OTHER INFORMATION: humanized VH-c104H08

<400> SEQUENCE: 24

Met Gly Trp Ser Tyr Ile Ile Leu Phe Leu Val Ala Thr Ala Thr Asp
1               5                   10                  15

Gly His Ser Gln Val Gln Leu Gln Gln Pro Gly Ala Glu Val Lys Lys
                20                  25                  30

Pro Gly Ser Ser Val Lys Leu Ser Cys Lys Ala Ser Gly Tyr Thr Phe
                35                  40                  45

Thr Ser Tyr Trp Ile His Trp Val Lys Gln Ala Pro Gly Gln Gly Leu
    50                  55                  60

Glu Trp Ile Gly Glu Ile Asn Pro Ser Ser Gly Arg Thr Asn Tyr Asn
65                  70                  75                  80

Glu Lys Phe Lys Asn Lys Val Thr Ile Thr Val Asp Lys Ser Thr Ser
                85                  90                  95

Thr Ala Tyr Met Glu Leu Ser Ser Leu Arg Ser Glu Asp Thr Ala Val
                100                 105                 110

Tyr Tyr Cys Ala Ser Arg Gly Tyr Trp Gly Gln Gly Thr Thr Val Thr
                115                 120                 125

Val Ser Ser
    130

<210> SEQ ID NO 25
<211> LENGTH: 717
<212> TYPE: DNA
<213> ORGANISM: artificial
<220> FEATURE:
<223> OTHER INFORMATION: humanized VL+CL-c103E08 (nucleotides)

<400> SEQUENCE: 25
atggagacag acacaatcct gctatgggtg ctgctgctct gggttccagg ctccactggt      60
gatattgtgc tgacccagag cccggacagc ctggcagtga gtctgggtca acgcgccacc     120
attaactgca aagccagcca gagcgtggat tatgacggcg gtagctacat gagctggttt     180
```

| | |
|---|---|
| cagcagaaac cgggtcagcc gccgaaactg ctgatttatg ccgccagcaa tctggaaagc | 240 |
| ggcgttccgg cccgtttag cggtagcggc agcggcaccg attttaccct gaccattagc | 300 |
| tcgctgcagg cggaggatgt ggccacctat tactgccagc agagctacga agatccgctg | 360 |
| acctttggcg gcgtaccaa agtggagatt aaacgaactg tggctgcacc atctgtcttc | 420 |
| atcttcccgc catctgatga gcagttgaaa tctggaactg cctctgttgt gtgcctgctg | 480 |
| aataacttct atcccagaga ggccaaagta cagtggaagg tggataacgc cctccaatcg | 540 |
| ggtaactccc aggagagtgt cacagagcag gacagcaagg acagcaccta cagcctcagc | 600 |
| agcaccctga cgctgagcaa agcagactac gagaaacaca aagtctacgc ctgcgaagtc | 660 |
| acccatcagg gcctgagctc gcccgtcaca aagagcttca acaggggaga gtgttaa | 717 |

<210> SEQ ID NO 26
<211> LENGTH: 717
<212> TYPE: DNA
<213> ORGANISM: artificial
<220> FEATURE:
<223> OTHER INFORMATION: humanized VL+CL-cl03G05 (nucleotides)

<400> SEQUENCE: 26

| | |
|---|---|
| atggagacag acacaatcct gctatgggtg ctgctgctct gggttccagg ctccactggt | 60 |
| gacatcgtgc tgacccagtc ccctgcttcc ctcgctgtgt ccctgggcga gagggctacc | 120 |
| atctcctgta aggcctccca gtccgtggac tacgacggcg ctcctacat gtcctggttc | 180 |
| cagcagaggc ctggccagcc tcccaagctg ctgatctacg ctgcctccaa cctggagtcc | 240 |
| ggcgtgcctg ataggttcag cggatccggc tccggcaccg acttcaccct gaatatctcc | 300 |
| cctctggagg ctgaggacgt ggccgtgtac tactgccagc agtcctacga ggaccctctg | 360 |
| accttcggcg gcggcaccaa ggtggagatc aagagaactg tcgcagcacc ttccgtcttt | 420 |
| atttccac catcagatga acagctgaaa tccggtactg ccagtgtggt ctgtctgctc | 480 |
| aataatttct atcccgggga ggctaaagtc cagtggaaag tggataatgc ccttcagtcc | 540 |
| ggcaactccc aggagagcgt gaccgagcag gattctaagg actcaacata ttcactgtca | 600 |
| tctactctca ccctgtctaa ggctgattac gaaaagcaca aggtgtacgc ttgcgaagtt | 660 |
| actcatcagg gcctctcttc ccctgtgacc aagagtttca ccggggcga gtgctaa | 717 |

<210> SEQ ID NO 27
<211> LENGTH: 717
<212> TYPE: DNA
<213> ORGANISM: artificial
<220> FEATURE:
<223> OTHER INFORMATION: humanized VL+CL-cl03F04 (nucleotides)

<400> SEQUENCE: 27

| | |
|---|---|
| atggagacag acacaatcct gctatgggtg ctgctgctct gggttccagg ctccactggt | 60 |
| gacatcgtga tgacccagtc ccctgactcc ctggctgtgt ccctgggcga aagggccacc | 120 |
| atcaactgca aggcctccca gtccgtggac tacgacggcg ctcctacat gtcctggtac | 180 |
| cagcagaagc ccggccagcc tcccaagctg ctgatctccg ccgcttccaa tctggagtcc | 240 |
| ggcgtgcccg ataggttttc cggctccggc tccggcaccg actttaccct gaccatccac | 300 |
| tccctgcagg ccgaggacgt ggctgtgtac tactgccagc agtcctacga ggaccctctg | 360 |
| accttcggcg ccggcaccaa ggtggagatc aagagaactg tcgcagcacc ttccgtcttt | 420 |
| atttccac catcagatga acagctgaaa tccggtactg ccagtgtggt ctgtctgctc | 480 |
| aataatttct atcccgggga ggctaaagtc cagtggaaag tggataatgc ccttcagtcc | 540 | ggcaactccc aggagagcgt gaccgagcag gattctaagg actcaacata ttcactgtca   600 tctactctca ccctgtctaa ggctgattac gaaaagcaca aggtgtacgc ttgcgaagtt   660 actcatcagg gcctctcttc ccctgtgacc aagagtttca accggggcga gtgctaa      717

<210> SEQ ID NO 28
<211> LENGTH: 717
<212> TYPE: DNA
<213> ORGANISM: artificial
<220> FEATURE:
<223> OTHER INFORMATION: humanized VL+CL-cl03H08 (nucleotides)

<400> SEQUENCE: 28
atggagacag acacaatcct gctatgggtg ctgctgctct gggttccagg ctccactggt    60
gacatcgtgc tgacccagtc ccctgcttcc ctggctgtgt ccctgggcga gagggctacc   120
atctcctgca aggcctccca gtccgtggac tacgacggcg ctcctacat gtcctggtac    180 cagcagaagc ccggccagcc tcccaagctg ctgatctacg ccgcctccaa cctggagtcc   240
ggcgtgcccg ataggttctc cggatccggc tccggcaccg acttcaccct gaacatctcc   300
tccgtgcagg aggaggacgt ggccacctac tactgccagc agtcctatga ggacccctg    360 accttcggcg ctggcaccaa ggtggagatc aagagaactg tcgcagcacc ttccgtcttt   420
attttcccac catcagatga acagctgaaa tccggtactg ccagtgtggt ctgtctgctc   480
aataatttct atcccggga ggctaaagtc cagtggaaag tggataatgc ccttcagtcc    540
ggcaactccc aggagagcgt gaccgagcag gattctaagg actcaacata ttcactgtca   600
tctactctca ccctgtctaa ggctgattac gaaaagcaca aggtgtacgc ttgcgaagtt   660
actcatcagg gcctctcttc ccctgtgacc aagagtttca accggggcga gtgctaa      717

<210> SEQ ID NO 29
<211> LENGTH: 717
<212> TYPE: DNA
<213> ORGANISM: artificial
<220> FEATURE:
<223> OTHER INFORMATION: humanized VL+CL-cl04H08 (nucleotides)

<400> SEQUENCE: 29
atggagacag acacaatcct gctatgggtg ctgctgctct gggttccagg ctccactggt    60
gacatcgtgc tgacccagtc ccctgcttcc ctggctgtgt ccctgggaga gagggccacc   120
atcaactgca aggcctccca gtccgtggac tacgacggcg ctcctacat gtcctggtac    180 cagcagaggc ccggacagcc tcccaagctg ctgatctacg ctgcctccaa cctggagtcc   240
ggcgtgcctg ataggttttc cggctccggc tccggaaccg acttcaccct gaccatccac   300
tccctgcagg cggaggacgt ggccacctac tactgccagc agtcctacga ggacccctg    360 acattcggcg ccggaaccaa ggtggagatc aagagaactg tcgcagcacc ttccgtcttt   420
attttcccac catcagatga acagctgaaa tccggtactg ccagtgtggt ctgtctgctc   480
aataatttct atcccggga ggctaaagtc cagtggaaag tggataatgc ccttcagtcc    540
ggcaactccc aggagagcgt gaccgagcag gattctaagg actcaacata ttcactgtca   600
tctactctca ccctgtctaa ggctgattac gaaaagcaca aggtgtacgc ttgcgaagtt   660
actcatcagg gcctctcttc ccctgtgacc aagagtttca accggggcga gtgctaa      717

<210> SEQ ID NO 30
<211> LENGTH: 717
<212> TYPE: DNA

```
<213> ORGANISM: artificial
<220> FEATURE:
<223> OTHER INFORMATION: chimeric VL+CL (nucleotides)

<400> SEQUENCE: 30
atggagacag acacaatcct gctatgggtg ctgctgctct gggttccagg ctccactggt      60
gacattgtgc tgacccaatc tccagcttct ttggctgtgt ctctagggca gagggccacc     120
atctcctgca aggccagcca aagtgttgat tatgatggtg gtagttatat gagttggttc     180
caacagagac caggacagcc acccaaactc ctcatctctg ctgcatccaa ccttgaatct     240
ggcatcccag ccaggtttag tggcagtggg tctgggacag acttcaccct caatatccat     300
cctgtggagg aggaggatgt tgcaacctat tactgtcagc aaagttatga agacccgctc     360
acgttcggtg ctggtaccaa ggtggagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660 acccatcagg gcctgagctc gcccgtcaca aagagcttca caggggaga gtgttaa        717

<210> SEQ ID NO 31
<211> LENGTH: 1386
<212> TYPE: DNA
<213> ORGANISM: artificial
<220> FEATURE:
<223> OTHER INFORMATION: humanized VH+CH1+CH2+CH3-cl03E08, knob
      mutation, (nucleotides)

<400> SEQUENCE: 31
atgggatgga gctatatcat cctcttttg gtagcaacag ctacagatgg ccactcccag       60
gtgcagctgc agcagtcggg tgccgaagtg aaaaaaccgg tgctagtgt gaaactgagc      120 tgcaaagcca gcggctatac cttcaccagc tactggatcc actgggtgcg tcaggcgcct     180
ggccagggcc tggaatggat tgcgaaaatc aatccgagca gcggtcgcac caattacaat     240
gaaaaattta aaaatcgtgt gaccgttacc gtggataaaa gcacctccac cgcctatatg     300
gagctgagca gcctgaccag cgaagatagc gccgtgtatt attgcgccag ccgcggttat     360
tggggccagg gtaccaccct gaccgtgagc agcgctagca cgaagggccc atcggtcttc     420
cccctggcac cctcctccaa gagcacctct gggggcacag cggccctggg ctgcctggtc     480
aaggactact ccccgaacc ggtgacggtg tcgtggaact caggcgccct gaccagcggc     540
gtgcacacct tcccggctgt cctacagtcc tcaggactct actccctcag cagcgtggtg     600
accgtgccct ccagcagctt gggcacccag acctacatct gcaacgtgaa tcacaagccc     660
agcaacacca aggtggacaa gaaagttgag cccaaatctt gtgacaaaac tcacacatgc     720
ccaccgtgcc cagcacctga actcctgggg ggaccgtcag tcttcctctt ccccccaaaa     780
cccaaggaca cctcatgat ctcccggacc cctgaggtca catgcgtggt ggtggacgtg      840
agccacgaag accctgaggt caagttcaac tggtacgtgg acggcgtgga ggtgcataat     900
gccaagacaa agccgcggga ggagcagtac aacagcacgt accgtgtgg cagcgtcctc      960 accgtcctgc accaggactg gctgaatggc aaggagtaca agtgcaaggt ctccaacaaa    1020
gccctcccag cccccatcga gaaaaccatc tccaaagcca agggcagcc ccgagaacca     1080 caggtgtaca ccctgccccc atcccgggat gagctgacca agaaccaggt cagcctgtgg    1140
```

```
tgcctggtca aaggcttcta tcccagcgac atcgccgtgg agtgggagag caatgggcag   1200
ccggagaaca actacaagac cacgcctccc gtgctggact ccgacggctc cttcttcctc   1260
tacagcaagc tcaccgtgga caagagcagg tggcagcagg ggaacgtctt ctcatgctcc   1320
gtgatgcatg aggctctgca caaccactac acgcagaaga gcctctccct gtctccgggt   1380
aaatag                                                              1386
```

<210> SEQ ID NO 32
<211> LENGTH: 1386
<212> TYPE: DNA
<213> ORGANISM: artificial
<220> FEATURE:
<223> OTHER INFORMATION: humanized VH+CH1+CH2+CH3-cl03G05, knob
      mutation, (nucleotides)

<400> SEQUENCE: 32

```
atgggatgga gctatatcat cctcttttg gtagcaacag ctacagatgg ccactcccag    60
gtgcagctgg tgcagcccgg cacagaggtg aagaagcctg gcgcctccgt gaagctgtcc   120
tgcaaggcct ccggctacac cttcaccagc tactggatcc actgggtgag gcaggctcct   180
ggacagggcc tggagtggat gggcgagatc aaccctcct ccggcaggac caactacaac    240
gagaagttca gaaccgggt gaccatcacc gccgacaagt ccacctccac cgcctacatg    300
cagctgtcct ccctgaggtc cgaggacacc gccgtgtact actgcgcctc caggggatat   360
tggggccagg gcaccacagt gaccgtgagc tccgctagca cgaagggccc atcggtcttc   420
cccctggcac cctcctccaa gagcacctct gggggcacag cggccctggg ctgcctggtc   480
aaggactact tccccgaacc ggtgacggtg tcgtggaact caggcgccct gaccagcggc   540
gtgcacacct tccggctgt cctacagtcc tcaggactct actccctcag cagcgtggtg   600
accgtgccct ccagcagctt gggcacccag acctacatct gcaacgtgaa tcacaagccc   660
agcaacacca aggtggacaa gaaagttgag cccaaatctt gtgacaaaac tcacacatgc   720
ccaccgtgcc cagcacctga actcctgggg ggaccgtcag tcttcctctt ccccccaaaa   780
cccaaggaca cctcatgat ctcccggacc cctgaggtca catgcgtggt ggtggacgtg    840
agccacgaag accctgaggt caagttcaac tggtacgtgg acggcgtgga ggtgcataat   900
gccaagacaa agccgcggga ggagcagtac aacagcacgt accgtgtggt cagcgtcctc   960
accgtcctgc accaggactg gctgaatggc aaggagtaca agtgcaaggt ctccaacaaa   1020
gccctcccag cccccatcga gaaaaccatc tccaaagcca agggcagcc cgagaacca   1080 caggtgtaca ccctgccccc atcccgggat gagctgacca gaaccaggt cagcctgtgg   1140 tgcctggtca aggcttcta tcccagcgac atcgccgtgg agtgggagag caatgggcag   1200
ccggagaaca actacaagac cacgcctccc gtgctggact ccgacggctc cttcttcctc   1260
tacagcaagc tcaccgtgga caagagcagg tggcagcagg ggaacgtctt ctcatgctcc   1320
gtgatgcatg aggctctgca caaccactac acgcagaaga gcctctccct gtctccgggt   1380
aaatag                                                              1386
```

<210> SEQ ID NO 33
<211> LENGTH: 1386
<212> TYPE: DNA
<213> ORGANISM: artificial
<220> FEATURE:
<223> OTHER INFORMATION: humanized VH+CH1+CH2+CH3-cl03F04, knob mutation
      (nucleotides)

<400> SEQUENCE: 33

| | |
|---|---|
| atgggatgga gctatatcat cctcttttg gtagcaacag ctacagatgg ccactcccag | 60 |
| gtgcagctgc agcagcccgg agccgaagtg aagaagcccg gctccagcgt gaagctgtcc | 120 |
| tgcaaggcct ccggctacac cttcacctcc tactggatcc actgggtgaa gcaggctcct | 180 |
| ggacagggcc tggagtggat cggcgagatc aaccnctcct ccggccggac caactacaac | 240 |
| gagaagttca gaacaaggt gaccatcacc gtggacaagt ccacctccac cgcctacatg | 300 |
| gagctgtcca acctgcggtc cgaggactcc gccgtgtact actgtgcctc aggggctat | 360 |
| tggggccagg gcacaaccct gaccgtgtcc tccgctagca cgaagggccc atcggtcttc | 420 |
| cccctggcac cctcctccaa gagcacctct gggggcacag cggccctggg ctgcctggtc | 480 |
| aaggactact cccccgaacc ggtgacggtg tcgtggaact caggcgccct gaccagcggc | 540 |
| gtgcacacct tcccggctgt cctacagtcc tcaggactct actccctcag cagcgtggtg | 600 |
| accgtgccct ccagcagctt gggcacccag acctacatct gcaacgtgaa tcacaagccc | 660 |
| agcaacacca aggtggacaa gaaagttgag cccaaatctt gtgacaaaac tcacacatgc | 720 |
| ccaccgtgcc cagcacctga actcctgggg ggaccgtcag tcttcctctt ccccccaaaa | 780 |
| cccaaggaca ccctcatgat ctcccggacc cctgaggtca catgcgtggt ggtggacgtg | 840 |
| agccacgaag accctgaggt caagttcaac tggtacgtgg acggcgtgga ggtgcataat | 900 |
| gccaagacaa agccgcggga ggagcagtac aacagcacgt accgtgtggt cagcgtcctc | 960 |
| accgtcctgc accaggactg gctgaatggc aaggagtaca agtgcaaggt ctccaacaaa | 1020 |
| gccctcccag cccccatcga gaaaaccatc tccaaagcca agggcagccc cgagaaccca | 1080 |
| caggtgtaca ccctgccccc atcccgggat gagctgacca agaaccaggt cagcctgtgg | 1140 |
| tgcctggtca aaggcttcta tcccagcgac atcgccgtgg agtgggagag caatgggcag | 1200 |
| ccggagaaca actacaagac cacgcctccc gtgctggact ccgacggctc cttcttcctc | 1260 |
| tacagcaagc tcaccgtgga caagagcagg tggcagcagg ggaacgtctt ctcatgctcc | 1320 |
| gtgatgcatg aggctctgca caaccactac acgcagaaga gcctctccct gtctccgggt | 1380 |
| aaatag | 1386 |

<210> SEQ ID NO 34
<211> LENGTH: 1386
<212> TYPE: DNA
<213> ORGANISM: artificial
<220> FEATURE:
<223> OTHER INFORMATION: humanized VH+CH1+CH2+CH3-cl03H08, knob mutation, (nucleotides)

<400> SEQUENCE: 34

| | |
|---|---|
| atgggatgga gctatatcat cctcttttg gtagcaacag ctacagatgg ccactcccag | 60 |
| gtgcagctgg tgcagtccgg cgccgaagtg aagaagcccg gctcctccgt gaagctgagc | 120 |
| tgcaaggcct ccggctacac cttctcctcc tactggatcc actgggtgag gcaggctcct | 180 |
| ggacagggcc tggagtggat gggcgagatc aaccnctcct ccggcaggac caactacaac | 240 |
| gagaagttca gaaccgggt gaccatcacc gccgacaagt ccacctccac cgcctacatg | 300 |
| gagctgtcca acctgaggtc cgaggactcc gccgtgtact actgcgcctc aggggatat | 360 |
| tggggccagg gcaccaccct gacagtgtcc tccgctagca cgaagggccc atcggtcttc | 420 |
| cccctggcac cctcctccaa gagcacctct gggggcacag cggccctggg ctgcctggtc | 480 |
| aaggactact cccccgaacc ggtgacggtg tcgtggaact caggcgccct gaccagcggc | 540 |
| gtgcacacct tcccggctgt cctacagtcc tcaggactct actccctcag cagcgtggtg | 600 |

```
accgtgccct ccagcagctt gggcacccag acctacatct gcaacgtgaa tcacaagccc      660
agcaacacca aggtggacaa gaaagttgag cccaaatctt gtgacaaaac tcacacatgc      720
ccaccgtgcc cagcacctga actcctgggg ggaccgtcag tcttcctctt ccccccaaaa      780
cccaaggaca ccctcatgat ctcccggacc cctgaggtca catgcgtggt ggtggacgtg      840
agccacgaag accctgaggt caagttcaac tggtacgtgg acggcgtgga ggtgcataat      900
gccaagacaa agccgcggga ggagcagtac aacagcacgt accgtgtggt cagcgtcctc      960
accgtcctgc accaggactg gctgaatggc aaggagtaca agtgcaaggt ctccaacaaa     1020
gccctcccag cccccatcga gaaaaccatc tccaaagcca agggcagccc cgagaaccca     1080
caggtgtaca ccctgccccc atcccgggat gagctgacca gaaccaggtc agcctgtgg     1140 tgcctggtca aaggcttcta tcccagcgac atcgccgtgg agtgggagag caatgggcag     1200
ccggagaaca actacaagac cacgcctccc gtgctggact ccgacggctc cttcttcctc     1260
tacagcaagc tcaccgtgga caagagcagg tggcagcagg ggaacgtctt ctcatgctcc     1320
gtgatgcatg aggctctgca aaccactac acgcagaaga gcctctccct gtctccgggt     1380
aaatag                                                                1386
```

<210> SEQ ID NO 35
<211> LENGTH: 1386
<212> TYPE: DNA
<213> ORGANISM: artificial
<220> FEATURE:
<223> OTHER INFORMATION: humanized VH+CH1+CH2+CH3-cl04H08, knob
      mutation, (nucleotides)

<400> SEQUENCE: 35

```
atgggatgga gctatatcat cctcttttg gtagcaacag ctacagatgg ccactcccag       60
gtgcagctgc agcagcctgg agccgaggtg aagaagcccg gctcctccgt gaagctgtcc     120
tgcaaggcct ccggctacac cttcacctcc tactggatcc actgggtgaa gcaggccct      180 ggacagggcc tggagtggat cggcgagatc aaccccctcct ccggcaggac caactacaac     240
gagaagttca gaacaaggt gaccatcacc gtggacaagt ccacctccac cgcctacatg       300
gagctgtcct ccctgaggtc cgaggacacc gccgtgtact actgtgcctc caggggctat     360
tggggccagg gcacaaccgt gaccgtgtcc tccgctagca cgaagggccc atcggtcttc     420
cccctggcac cctcctccaa gagcacctct gggggcacag cggccctggg ctgcctggtc     480
aaggactact tccccgaacc ggtgacggtg tcgtggaact caggcgccct gaccagcggc     540
gtgcacacct tccggctgt cctacagtcc tcaggactct actccctcag cagcgtggtg      600
accgtgccct ccagcagctt gggcacccag acctacatct gcaacgtgaa tcacaagccc     660
agcaacacca aggtggacaa gaaagttgag cccaaatctt gtgacaaaac tcacacatgc     720
ccaccgtgcc cagcacctga actcctgggg ggaccgtcag tcttcctctt ccccccaaaa     780
cccaaggaca ccctcatgat ctcccggacc cctgaggtca catgcgtggt ggtggacgtg     840
agccacgaag accctgaggt caagttcaac tggtacgtgg acggcgtgga ggtgcataat     900
gccaagacaa agccgcggga ggagcagtac aacagcacgt accgtgtggt cagcgtcctc     960
accgtcctgc accaggactg gctgaatggc aaggagtaca agtgcaaggt ctccaacaaa    1020
gcccccccag cccccatcga gaaaaccatc tccaaagcca agggcagccc cgagaacca     1080 caggtgtaca ccctgccccc atcccgggat gagctgacca gaaccaggt cagcctgtgg     1140 tgcctggtca aaggcttcta tcccagcgac atcgccgtgg agtgggagag caatgggcag    1200
```

| ccggagaaca actacaagac cacgcctccc gtgctggact ccgacggctc cttcttcctc | 1260 |
| tacagcaagc tcaccgtgga caagagcagg tggcagcagg ggaacgtctt ctcatgctcc | 1320 |
| gtgatgcatg aggctctgca caaccactac acgcagaaga gcctctccct gtctccgggt | 1380 |
| aaatag | 1386 |

<210> SEQ ID NO 36
<211> LENGTH: 1386
<212> TYPE: DNA
<213> ORGANISM: artificial
<220> FEATURE:
<223> OTHER INFORMATION: chimeric VH+CH1+CH2+CH3, knob mutation, (nucleotides)

<400> SEQUENCE: 36

| atgggatgga gctatatcat cctcttttg gtagcaacag ctacagatgg ccactcccag | 60 |
| gtccaactgc aacagcctgg gactgaactg gtgaagcctg ggcttcagt gaagctgtcc | 120 |
| tgcaaggctt ctggctacac cttcaccagt tactggatac actgggtgaa gcagaggcct | 180 |
| ggacaaggcc ttgagtggat tggagagatt aatcctagca gcggtcgtac taactacaac | 240 |
| gagaaattca gaacaaggt cacagtgact gtagacaaat cttccaccac agcctacatg | 300 |
| caactcagca acctgacatc tgaggactct gcggtctatt actgtgcaag taggggctac | 360 |
| tgggggccaag gcaccactct cacagtctcc tcagctagca cgaagggccc atcggtcttc | 420 |
| cccctggcac cctcctccaa gagcacctct ggggggcacag cggccctggg ctgcctggtc | 480 |
| aaggactact tccccgaacc ggtgacggtg tcgtggaact caggcgccct gaccagcggc | 540 |
| gtgcacacct tcccggctgt cctacagtcc tcaggactct actccctcag cagcgtggtg | 600 |
| accgtgccct ccagcagctt gggcacccag acctacatct gcaacgtgaa tcacaagccc | 660 |
| agcaacacca aggtggacaa gaaagttgag cccaaatctt gtgacaaaac tcacacatgc | 720 |
| ccaccgtgcc cagcacctga actcctgggg ggaccgtcag tcttcctctt ccccccaaaa | 780 |
| cccaaggaca cctcatgat ctcccggacc cctgaggtca catgcgtggt ggtggacgtg | 840 |
| agccacgaag accctgaggt caagttcaac tggtacgtgg acggcgtgga ggtgcataat | 900 |
| gccaagacaa agccgcggga ggagcagtac aacagcacgt accgtgtggt cagcgtcctc | 960 |
| accgtcctgc accaggactg gctgaatggc aaggagtaca agtgcaaggt ctccaacaaa | 1020 |
| gccctcccag cccccatcga gaaaaccatc tccaaagcca agggcagcc cgagaaccca | 1080 |
| caggtgtaca ccctgccccc atcccgggat gagctgacca agaaccaggt cagcctgtgg | 1140 |
| tgcctggtca aaggcttcta tcccagcgac atcgccgtgg agtgggagag caatgggcag | 1200 |
| ccggagaaca actacaagac cacgcctccc gtgctggact ccgacggctc cttcttcctc | 1260 |
| tacagcaagc tcaccgtgga caagagcagg tggcagcagg ggaacgtctt ctcatgctcc | 1320 |
| gtgatgcatg aggctctgca caaccactac acgcagaaga gcctctccct gtctccgggt | 1380 |
| aaatag | 1386 |

<210> SEQ ID NO 37
<211> LENGTH: 741
<212> TYPE: DNA
<213> ORGANISM: artificial
<220> FEATURE:
<223> OTHER INFORMATION: human CH2+CH3, Hole mutations, (nucleotides)

<400> SEQUENCE: 37

| atgggatgga gctatatcat cctcttttg gtagcaacag ctacagatgg ccactccgac | 60 |

```
aaaactcaca catgcccacc gtgcccagca cctgaactcc tgggggggacc gtcagtcttc    120 ctcttccccc caaaacccaa ggacaccctc atgatctccc ggaccCCtga ggtcacatgc    180
gtggtggtgg acgtgagcca cgaagaccct gaggtcaagt tcaactggta cgtggacggc    240
gtggaggtgc ataatgccaa gacaaagccg cgggaggagc agtacaacag cacgtaccgt    300
gtggtcagcg tcctcaccgt cctgcaccag gactggctga atggcaagga gtacaagtgc    360
aaggtctcca acaaagccct cccagccccc atcgagaaaa ccatctccaa agccaaaggg    420
cagccccgag aaccacaggt gtacaccctg cccccatccc gggatgagct gaccaagaac    480
caggtcagcc tgagttgcgc ggtcaaaggc ttctatccca gcgacatcgc cgtggagtgg    540
gagagcaatg ggcagccgga gaacaactac aagaccacgc ctcccgtgct ggactccgac    600
ggctccttct cctcgtcag caagctcacc gtggacaaga gcaggtggca gcaggggaac    660
gtcttctcat gctccgtgat gcatgaggct ctgcacaacc actacacgca gaagagcctc    720
tccctgtctc cgggtaaata g                                              741
```

```
<210> SEQ ID NO 38
<211> LENGTH: 18
<212> TYPE: DNA
<213> ORGANISM: artificial
<220> FEATURE:
<223> OTHER INFORMATION: His-TAG (nucleotide)

<400> SEQUENCE: 38
caccatcacc atcaccat                                                   18

<210> SEQ ID NO 39
<211> LENGTH: 6
<212> TYPE: PRT
<213> ORGANISM: artificial
<220> FEATURE:
<223> OTHER INFORMATION: His-TAG

<400> SEQUENCE: 39

His His His His His His
1               5

<210> SEQ ID NO 40
<211> LENGTH: 108
<212> TYPE: DNA
<213> ORGANISM: artificial
<220> FEATURE:
<223> OTHER INFORMATION: Strep-TAG (nucleotide)

<400> SEQUENCE: 40
ggtgccgcat ggagccaccc ccagttcgaa aaaggggccg catggagcca ccccagttc      60 gaaaaagggg ccgcatggag ccacccccag ttcgaaaaag gggccgca               108

<210> SEQ ID NO 41
<211> LENGTH: 36
<212> TYPE: PRT
<213> ORGANISM: artificial
<220> FEATURE:
<223> OTHER INFORMATION: Strep-TAG

<400> SEQUENCE: 41

Gly Ala Ala Trp Ser His Pro Gln Phe Glu Lys Gly Ala Ala Trp Ser
1               5                   10                  15

His Pro Gln Phe Glu Lys Gly Ala Ala Trp Ser His Pro Gln Phe Glu
            20                  25                  30
```

```
<210> SEQ ID NO 42
<211> LENGTH: 39
<212> TYPE: DNA
<213> ORGANISM: artificial
<220> FEATURE:
<223> OTHER INFORMATION: K842E sense nucleotide

<400> SEQUENCE: 42
gtacataatc ctgtgtttga gcctttgaa aagccagtg                    39

<210> SEQ ID NO 43
<211> LENGTH: 39
<212> TYPE: DNA
<213> ORGANISM: artificial
<220> FEATURE:
<223> OTHER INFORMATION: K842E antisense nucleotide

<400> SEQUENCE: 43
cactggcttt tcaaaaggct caaacacagg attatgtac                    39
```

ANTI-MET FAB-FC FOR THE TREATMENT OF A TUMOR AND/OR METASTASIS

FIELD OF THE INVENTION

The present disclosure concerns a novel antibody-derived therapeutic agent for the treatment of a tumor and/or metastasis.

BACKGROUND

Cancer is a genetic disease in which somatic endogenous genes undergo mutations. Only a handful of genes—known as oncogenes and tumor suppression genes—are altered in cancer cells and drive tumorigenesis.

The activated oncogenes are accelerators and the inactivated tumor suppressor genes are missing brakes for cancer cell growth. Subsequent to the discovery of cancer-causing mutated genes, a new concept emerged for oncogenes: the "oncogene addiction", which indicates that a cancer cell, despite its abundance of genetic alterations, is still dependent on a single oncogenic protein for its sustained proliferation or survival. Therefore, new therapeutic inroads were undertaken to develop "target therapy" to cure cancer. In the last 20 years, pharmacological targeting of proteins encoded by cancer-causing mutated genes—through chemical drugs or antibodies—has represented the forefront armamentarium to eliminate the mutated cells and combat cancer disease. Target therapies promise to be more effective than conventional cytotoxic chemotherapies, often fewer side effects. However, only the patients bearing in their tumors the altered specific target gene are likely to benefit from target therapy. Thus, personalized medicine is required in parallel to assess the druggable genetic lesions through comprehensive genomic profiling of the patient tumor.

The MET oncogene encodes for a unique receptor tyrosine kinase endowed with pleiotropic functions. When genetically altered (by point mutations, gene fusion, translocation, and/or amplification), MET initiates transformation of the cells by virtue of its ability to activate the invasive growth program. Thus, MET genetic lesions leading to constitutive Met kinase hyperactivation initiate and maintain the transformed phenotype ("MET addiction") 1.

MET genetic lesions occur in most solid tumors with an overall frequency of 1-4% and are able to upregulate its kinase activity[1]. Point mutations are concentrated in domains critical for Hepatocyte Growth Factor (HGF) ligand binding or receptor signalling (SEMA domain, juxtamembrane domain, and catalytic domain). Most recently, next-generation sequencing revealed exon 14 splice site mutations in 3% of non-small cell lung cancers[2], which lead to exon skipping and deletion of the juxtamembrane region of the MET transcript, where a serine residue (Ser985) negatively regulates the Met kinase activity[3] and a tyrosine residue (Tyr1003) is required for Met internalization and degradation[4].

In the "invasive growth" program elicited by MET, the proliferative response is coupled with migration, survival, extracellular degradation, matrix and induction of cell polarity[5]. These biological responses are strived by cells to adapt to adverse conditions and/or escape to find a more convenient environment. In a hostile context, Met is overexpressed-via transcriptional upregulation—by a variety of stimuli such as hypoxia, inflammatory cytokines, pro-angiogenic factors, mitogens and even HGF itself. Lastly, Met is overexpressed in conditions of radiation-induced DNA damage and contributes to resistance to radiotherapy by promoting activation of DNA repair and evasion of programmed cell death of cancer cells.

Several Met-targeting molecules have been developed to erase the hyperactive Met signalling in a selective, robust, and highly effective manner. These drugs include: HGF antagonists (either blocking antibodies or decoys), mAbs targeting the Met receptor, and chemical tyrosine kinase inhibitors (TKIs). Anti-Met mAbs potentially represent a major step in the battle against the cancers driven by MET. Nowadays, four anti-Met mAbs have entered early clinical trials: MetMab (Onartuzumab, Roche), LY2875358 (Emibetuzumab, Eli Company), ARGX-111 (Argenx), SAIT301 Lilly & (Samsung) and Sym015 (Symphogen A/S), a mixture of two antibodies. They act by blocking HGF binding to MET in a competitive fashion (Onartuzumab, ARGX-111) and/or downregulating MET (Emibetuzumab, SAIT301, Sym015).

The murine DN30 mAb (disclosed in WO 2007/090807) is an IgG2A which binds the extracellular domain of the human Met receptor and induces only some of the Met-triggered biological effects[6]. It partially activates receptor phosphorylation due to its bivalent nature which allows simultaneous binding to two distinct antigen molecules, resulting in stabilization of receptor complexes in a fashion similar to that achieved by natural ligands. This unwanted partial agonistic activity on Met was not observed in the monovalent DN30 Fab fragment (MvDN30) 7. Conversion of the bivalent DN30 parental antibody into the monovalent Fab fragment unleashes the therapeutic potential of the DN30 anti-Met antibody, leading to a full antagonist molecule. However, the short half-life of the Fab, due to its low molecular weight, is a severe limitation for the deployment in therapy. The present inventors thus developed new engineered molecules called DCD (Dual Constant Domain Fab) characterized by the duplication of the constant domains present in the DN30 Fab: DCD-1, in which the duplication was done in tandem, and DCD-2, in which the constant domains of the light and heavy chain were reciprocally swapped (disclosed in WO 2014/108829). Both the new recombinant molecules show biochemical properties in vitro comparable to the original Fab, acting as full Met antagonists. In vivo, upon systemic administration, the new recombinant molecules reduce Met-addicted tumor growth. DCD-1 and DCD-2 show a pharmacokinetic profile improved over the original DN30 Fab, nevertheless none of two reach the behavior comparable to the mAb of origin[8].

It has been previously reported that conversion from bivalent to a monovalent form of an antibody can be reached also by deleting-trough a molecular engineering approach-one of the two antibody arms (disclosed in WO 2005/063816). Data reported an improvement in the in vivo stability of the molecule, mainly due to the activity of the Fc domain, which binds the Fc receptor expressed in the organs.

SUMMARY OF THE INVENTION

The object of this disclosure is to provide a novel anti-tumor agent derived from a monoclonal antibody useful in the treatment of oncologic patients, namely the DN30 monoclonal antibody.

According to the invention, the above object is achieved thanks to the subject matter recalled specifically in the ensuing claims, which are understood as forming an part integral of this disclosure.

The present invention concerns an anti-Met antibody fragment comprising a single antigen binding arm and an Fc region, wherein the Fc region comprises a complex of a first and a second Fc polypeptide. The antibody fragment comprises:

(i) a first polypeptide comprising one humanized light chain variable (VL) domain, and one human light chain constant (CL) domain, wherein the humanized light chain variable (VL) domain is fused to the human light chain constant (CL) domain in the N- to C-term direction, and wherein the humanized light chain variable (VL) domain contains three complementary determining regions (CDRs) having the amino acid sequences set forth in SEQ ID No.: 1, 2 and 3, and wherein the humanized VL domain has an amino acid sequence as set forth in SEQ ID No.: 7;

(ii) a second polypeptide comprising one humanized heavy chain variable (VH) domain, one human heavy chain constant CH1 domain and the first Fc polypeptide, wherein the first Fc polypeptide comprises one human hinge region, one human constant CH2 domain and one human constant CH3 domain, wherein the humanized heavy chain variable (VH) domain is fused to the human heavy chain constant CH1 domain, that is fused to the human hinge region, that is fused to the human constant CH2 domain, that is fused to the human constant CH3 domain in the N- to C-term direction, and wherein the humanized heavy chain variable (VH) domain contains three complementary determining regions (CDRs) having the amino acid sequences set forth in SEQ ID No.: 4, 5 and 6, and wherein the humanized VH domain has an amino acid sequence as set forth in SEQ ID No.: 8; 30

(iii) a third polypeptide comprising the second human Fc polypeptide, wherein the second human Fc polypeptide comprises one hinge region, one human constant CH2 domain and one human constant CH3 domain, wherein the hinge region is fused to the human CH2 constant domain that is fused to the human CH3 constant domain in the N- to C-term direction, wherein the hinge region is truncated at the N-terminus.

The improved therapeutic properties of the above described antibody fragment are dependent from the structure of the variable regions, and are not simply due to the monovalent form of the antibody and/or the presence of the Fc region.

The present invention also concerns a product comprising, in a single bottle or in two bottles, (a) the anti-Met antibody fragment as defined above, and a pharmaceutically acceptable vehicle, and (b) an extracellular portion of human Met and a vehicle, pharmaceutically acceptable wherein the extracellular portion of human Met is capable of binding to Hepatocyte Growth Factor (HGF) in a stable manner and contains at least one amino acid mutation within the epitope recognized by the anti-Met antibody fragment to prevent binding of the anti-Met antibody fragment thereto.

BRIEF DESCRIPTION OF THE DRAWINGS

The invention will now be described in detail, purely by way of an illustrative and non-limiting example and, with reference to the accompanying drawings, wherein:

FIG. 14: Amino acid sequences of VL, VH, CL and CH1 domains of choA-DN30 and hOA-DN30-c103E08 antibodies. The Complementary Determining Regions sequences are highlighted by a bold, underlined character.

FIG. 15: Amino acid sequences of the first and the second Fc polypeptides of OA-DN30. The amino acid mutations within the CH3 domains of the first and second Fc polypeptides-necessary for generating the knob and the hole, respectively,—are highlighted by a bold, underlined character.

FIG. 16: Amino acid sequence of the mutated form of DecoyMet. The amino acid mutation K842E is highlighted by a bold, underlined character.

FIG. 17: A copy of the Viability Statement for the biological material "DN30" due to the deposit on Apr. 16, 2008, of material assigned Deposit Number PD08003.

FIG. 18: A copy of the Receipt in the Case of an Original Deposit of the biological material "DN30" due to the deposit on Dec. 29, 2005, of material assigned Deposit Number PD 05006.

DETAILED DESCRIPTION OF THE INVENTION

Figure 1:
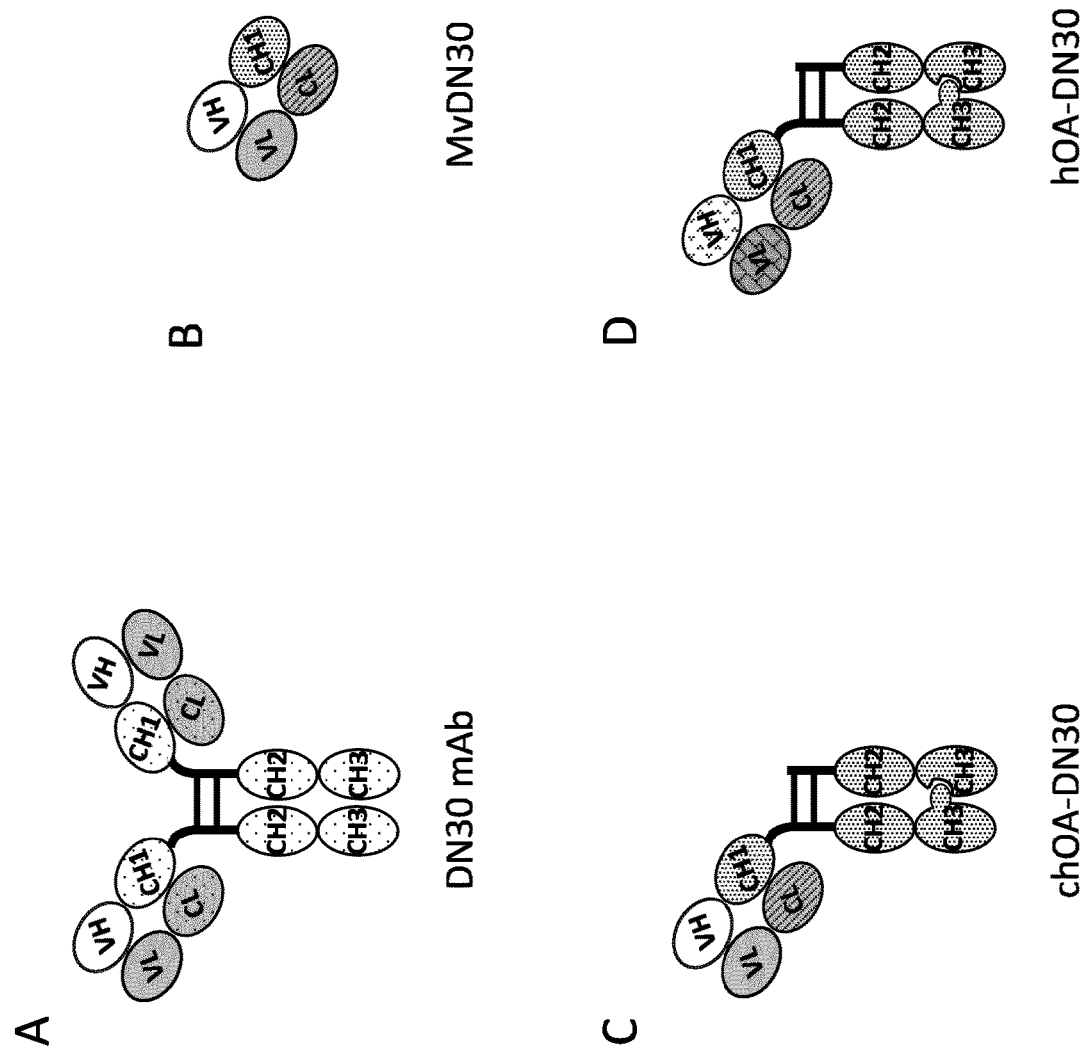
FIG. 1: Schematic representation of the DN30 antibody and its monovalent derivatives. (A) the original murine bivalent mAb; (B) MvDN30, the chimeric Fab; (C) choA-DN30, the chimeric monovalent 'One-Arm' antibody; (D) hOA-DN30, the humanized monovalent 'One-Arm' antibody; (E) The OA-DN30 antibodies were subjected to SDS-PAGE under reducing and not reducing conditions. The gel was stained with Gel Code blue.

In the following description, numerous specific details are given to provide a thorough understanding of the embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The instant disclosure concerns a novel therapeutic agent for the treatment of a tumor and/or metastasis.

It is estimated that more than 200,000 patients per year are "MET-addicted", and Met inhibition may potentially result in remission of the disease. Considering that mutations accumulate with aging and over the next 20 years the ageing population will increase, the burden of cancer is expected to rise and to have a high impact on global healthcare resources for patients' management. Genetic alterations responsible for "MET-addiction" have been found in gastric, oesophageal, colorectal, renal, and lung carcinoma, melanoma, and brain tumors (see COSMIC database: www.sanger.ac.uk). Moreover, selection of MET genetic lesions has been found as an acquired mechanism of resistance to a number of other targeted therapies in colorectal and non-small cell lung cancer (NSCLC)[9].

The role of Met in metastasis is also associated with the ability of Met in helping cells to adapt to a harsh environment. The metastatic capabilities driven by Met not only depend on genetic and epigenetic alterations, but also on paracrine secretion of HGF by tumor stromal tissue which is composed by a large variety of cell types, including fibroblasts, resident epithelial cells, pericytes, myofibroblasts, vascular and lympho-vascular endothelial cells, and infiltrating cells of the immune system.

Met is nowadays recognized as a cancer-specific target for: (i) personalized treatment of tumors with MET mutations/amplifications ('addicted to MET'); (ii) for prevention/reversion of Met-driven primary and resistance to other targeted cancer secondary therapies; and (iii) for prevention/reversion of Met-driven invasive/metastatic phenotype[1].

The DN30 inhibitory activity lies on its ability to promote the physiological activity of the metalloprotease ADAM-10 acting at the cell surface[10], which releases from the plasma membrane the intact extracellular portion of the receptor (Met-shedding), followed by the rapid degradation of the Met intracellular kinase domain[11]. As a consequence of these processes, Met is physically removed from the cell surface and the extracellular domain acts as soluble 'decoy', preventing ligand binding by sequestering HGF. Thus, the advantage of DN30 is to inhibit both HGF-dependent and HGF-independent activation of Met[12].

As compared with other anti-Met antibodies, DN30 blocks the receptor functions by a unique mechanism that rise to different and synergic activities: (i) removal of Met from the cell surface by 'shedding' of the ectodomain; (ii) sequestration of the HGF ligand; (iii) inhibition of the homo- or hetero-dimerization of Met receptor at the membrane; (iv) stimulation of receptor degradation. Thus, DN30 offers the opportunity to kill two birds with one stone, allowing optimal blockade of the Met pathway, as it can potentially act not only on cancer cells but also on the tumor microenvironment (HGF-driven biological responses of endothelial cells, fibroblasts, and macrophages).

The present invention relies on the idea that, to reach the highest therapeutic potential against a tumor by means of an anti-Met antibody, it is mandatory to apply a molecule that: i) is not eliciting, even also in part, intracellular responses evoked upon Met activation, i.e. is not an agonist or a partial agonist; ii) impairs Met activation through a mechanism of action different from ligand (HGF) displacement; iii) has a favorable pharmacokinetic profile, suitable for deployment in the clinic; iv) reasonably does not immune-response in humans. To fulfill all the exert above considerations, the inventors converted the murine DN30 antibody—that blocks Met activation by a shedding mechanism—into a fully humanized, monovalent and highly stable molecule, by formatting it in the "One-Arm" form, named in the following as "hOA-DN30".

In an embodiment, the present invention concerns an anti-Met antibody fragment comprising a single antigen binding arm and an Fc region, wherein the Fc region comprises a complex of a first and a second Fc polypeptide. The antibody fragment comprises, preferably consists of:

(i) a first polypeptide comprising, preferably consisting of, one humanized light chain variable (VL) domain, and one human light chain constant (CL) domain, wherein the humanized light chain variable (VL) domain is fused to the human light chain constant (CL) domain in the N- to C-term direction, and wherein the humanized light chain variable (VL) domain contains three complementary determining regions (CDRs) having the amino acid sequences set forth in SEQ ID No.: 1, 2 and 3, and wherein the humanized light chain variable (VL) domain has an amino acid sequence as set forth in SEQ ID No.: 7;

(ii) a second polypeptide comprising one humanized heavy chain variable (VH) domain, one human heavy chain constant CH1 domain and the first Fc polypeptide, wherein the first Fc polypeptide comprises one human hinge region, one human constant CH2 domain and one human constant CH3 domain, wherein the humanized heavy chain variable (VH) domain is fused to the human heavy chain constant CH1 domain, that is fused to the human hinge region, that is fused to the human constant CH2 domain, that is fused to the human constant CH3 domain in the N- to C-term direction, and wherein the humanized heavy chain variable (VH) domain contains three complementary determining regions (CDRs) having the amino acid sequences set forth in SEQ ID No.: 4, 5 and 6, and wherein the humanized heavy chain variable (VH) domain has an amino acid sequence as set forth in SEQ ID No.: 8.;

(iii) a third polypeptide comprising, preferably consisting of, the second human Fc polypeptide, wherein the second human Fc polypeptide comprises, preferably consists of, one human hinge region, one human constant CH2 domain and one human constant CH3 domain, wherein the hinge region is fused to the human CH2 constant domain, that is fused to the human CH3 constant domain in the N- to C-term direction, wherein the hinge region is truncated at the N-terminus.

In one embodiment, the human light chain constant (CL) domain is a human light kappa type domain.

In one embodiment, the human hinge region and the human constant domains CH1, CH2 and CH3 are from human IgG1.

In one embodiment, the two Fc polypeptides are linked through intermolecular disulfide bonds at the hinge region.

In one embodiment, the first Fc polypeptide and the second Fc polypeptide meet at an interface, and one between the first and the second Fc polypeptide comprises a knob at the interface, and the other between the first and the second Fc polypeptide comprises a hole at the interface, wherein the knob is positionable into the hole.

In a preferred embodiment, one between the first and the second Fc polypeptide comprises a mutated CH3 constant domain, wherein the mutated CH3 constant domain carries an amino acid mutation at position 389, wherein the original amino acid at position 389 has been mutated to import an amino acid having a larger side chain volume than the original amino acid, so as to create a knob at the interface between the Fc polypeptides; and wherein the other between the first and the second Fc polypeptide comprises a mutated CH3 constant domain, wherein the mutated CH3 constant domain carries three amino acid mutations at positions 389, 391 and 438, wherein the original amino acids have been mutated to import amino acids having smaller side chain volumes than the original amino acids, so as to create a hole at the interface between the Fc polypeptides, wherein the knob is positionable into the hole, and wherein the amino acid numbering is according to the EU numbering scheme of Kabat (pp. 688-696 in Sequences of proteins of immunological interest, 5th ed., Vol. 1, 1991; NIH, Bethesda, MD).

In a still preferred embodiment, the original amino acids at positions 389, 391 and 438 are threonine, leucine tyrosine respectively; and wherein in one between the first and the second Fc polypeptide the threonine in position 389 has been mutated to tryptophan; and wherein in the other between the first and the second Fc polypeptide the threonine at position 389 has been mutated to serine, the leucine at position 391 has been mutated to alanine and the tyrosine at position 438 has been mutated to valine.

In a preferred embodiment, the human light chain constant (CL) domain has an amino acid sequence as set forth in SEQ ID No.: 9 and the human heavy chain constant CH1 domain has an amino acid sequence as set forth in SEQ ID No.: 10.

In a preferred embodiment, the first human Fc polypeptide has an amino acid sequence as set forth in SEQ ID No.: 11, and the second human Fc polypeptide has an amino acid sequence as set forth in SEQ ID No.: 12.

In an embodiment, the present invention concerns an isolated nucleic acid encoding the anti-Met antibody fragment as disclosed above.

In an embodiment, the present invention concerns a composition comprising two or more recombinant nucleic acids which collectively encode the anti-Met antibody fragment as disclosed above.

The anti-Met antibody fragment disclosed herein when bound to Met induces shedding of the extracellular domain of Met. The anti-Met antibody fragment when bound to Met does not exert an agonistic activity towards Met. The anti-Met antibody fragment when bound to Met inhibits Met phosphorylation. The anti-Met antibody fragment when bound to Met further blocks proliferation and induces cytotoxicity in MET-addicted cells. The anti-Met antibody fragment when bound to Met further inhibits cell motility and cell invasion induced by Hepatocyte Growth Factor (HGF). The aforementioned properties of the anti-Met antibody fragment object of the instant description provide said antibody fragment with anti-tumor and/or anti-metastasis activity.

The expression "antigen binding arm", as used herein, refers to a component part of an antibody fragment of the invention that has an ability to bind specifically a target molecule of interest. The antigen binding arm is a complex of variable domain sequences (VL and VH), including the CDRs and the Frame Regions of an immunoglobulin light and heavy chain, and constant domain (CL sequences and CH) of an immunoglobulin light and heavy chain.

"Humanized" forms of non-human (e.g., murine) antibodies are non-natural recombinant antibodies that contain minimal amino acid residues derived from non-human immunoglobulin. For the most part, humanized antibodies are human immunoglobulins (recipient antibody) in which residues from a hypervariable region of the recipient (i.e. the Complementarity Determining Regions-CDRs) are replaced by residues from a hypervariable region of a non-human species (donor antibody) having the desired specificity, affinity, and properties. In some instances, framework region (FR) residues of the human immunoglobulin can be replaced by corresponding non-human residues.

Furthermore, humanized antibodies may comprise residues that are not found in the recipient antibody or in the donor antibody. These modifications are made to further refine antibody performance. In general, the humanized antibody will comprise two variable domains, in which all or substantially all of the hypervariable loops correspond to those of a non-human immunoglobulin and all or substantially all of the Frame residues (FRs) are those of a human immunoglobulin sequence. The humanized antibody also comprises a portion of an immunoglobulin constant region (Fc), typically that of a human immunoglobulin. For further details, see 13-15. See also the following review articles and references cited therein: 16-18.

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG1 heavy chain Fc sequence is usually defined to stretch from an amino acid residue included between Asp 234 and Thr 238, to the carboxyl terminus of the Fc sequence according to the EU numbering scheme of Kabat. The Fc sequence of an immunoglobulin generally comprises one hinge region, two constant domains, a CH2 domain and a CH3 domain, and optionally comprises a CH4 domain. By "Fc polypeptide" herein is meant one of the polypeptides that make up an Fc region. The Fc region stability of the antibody fragment compared to a Fab molecule comprising an antigen binding arm.

The "hinge region", "hinge sequence", and variations thereof, as used herein, includes the meaning known in the art, which is illustrated in, for example, Janeway et al., Immuno Biology: the immune system in health and disease, (Elsevier Science Ltd., NY) (4th ed., 1999) and in [19,20].

The phrase "truncated hinge region", as used herein, refers to a polypeptide comprising parts, but not all, of a hinge sequence. The truncated hinge region is capable of linkage to the "first" Fc polypeptide. If the wild type hinge sequence is not present, the remaining sequence in the "second" Fc polypeptide would comprise a component that is capable of linkage to the "first" Fc polypeptide. For example, said component can be a modified residue or an added cysteine residue capable of forming a disulfide linkage.

A "knob" refers to at least one amino acid side chain which projects from the interface of a first Fc polypeptide and is therefore positionable in a compensatory hole in the adjacent interface (i.e. the interface of a second Fc polypeptide) so as to stabilize the heteromultimer, and thereby favor heteromultimer formation over homomultimer formation, for example. The knob may exist in the original interface or may be introduced synthetically (e.g. by altering nucleic acid encoding the interface). Normally, a nucleic acid encoding the interface of the first polypeptide is altered to encode the knob. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide.

A "hole" refers to at least one amino acid side chain which is recessed from the interface of a second Fc polypeptide and therefore accommodates a corresponding knob on the adjacent interface of a first Fc polypeptide. The hole may exist in the original interface or may be introduced synthetically (e.g. by altering nucleic acid encoding the interface). Normally, nucleic acid encoding the interface of the second polypeptide is altered to encode the hole. To achieve this, the nucleic acid encoding at least one "original" amino acid residue in the interface of the second polypeptide is replaced with nucleic acid encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide.

The knob is "positionable" into the hole which means that the spatial location of the knob and hole on the interface of a first Fc polypeptide and second Fc polypeptide respectively and the sizes of the knob and hole are such that the knob can be located into the significantly perturbing the normal hole without association of the first and second polypeptides at the interface. Since knobs do not typically extend perpendicularly from the axis of the interface and have preferred conformations, the alignment of a knob with a corresponding hole relies on modeling the knob/hole pair based upon a three-dimensional structure such as that obtained by X-ray crystallography or nuclear magnetic resonance (NMR). This can be achieved using widely accepted techniques in the art.

The expression "non-agonist activity" of the anti-Met antibody fragment as used herein refers to the anti-Met antibody fragment that does not exert any activity that elicits, even also in part, cellular responses evoked upon Met activation. The non-agonistic activity of the anti-Met antibody fragment can be measured by the evaluation of the Met level of phosphorylation by conventional techniques such as western blot, immunofluorescence, immunohistochemistry, ELISA, cytofluorimeter analysis or any other method that includes the use of an antibody that recognizes specifically Met, or the Met residues Tyr1234-1235 if phosphorylated (i.e. the major phosphorylation site of Met[21]), or Met Tyr the residues 1349/1356 if phosphorylated (i.e. the docking site of Met[22]) upon incubation of the cells with the said non-agonist antibody. As an alternative, the evaluation of cellular biological responses upon antibody treatment compared to the responses induced by HGF treatment can be applied.

The present invention further concerns a product comprising, in a single bottle or in two bottles, (a) the anti-Met antibody fragment as disclosed herein, and a pharmaceutically acceptable vehicle, and (b) an extracellular portion of human Met and a pharmaceutically acceptable vehicle, wherein the extracellular portion of human Met is capable of binding to Hepatocyte Growth Factor (HGF) in a stable manner and contains at least one amino acid mutation within the epitope recognized by the anti-Met antibody fragment to prevent binding of the anti-Met antibody fragment thereto.

In an embodiment, the extracellular portion of human Met contains SEMA, PSI, IPT-1, IPT-2, IPT-3 and IPT-4 domains.

In a preferred embodiment, the extracellular portion of human Met has an amino acid sequence as set forth in SEQ ID No.: 13, wherein at least one of the amino acids between position 797 and position 875 of SEQ ID No.: 13 is mutated in order to prevent binding of the anti-Met antibody fragment thereto.

In a more preferred embodiment, the extracellular portion of human Met has the amino acid sequence set forth in SEQ ID No.: 14.

The present description also concerns a nucleic acid molecule encoding the extracellular portion of human Met capable of binding to Hepatocyte Growth Factor (HGF) in a stable manner and containing at least one amino acid mutation within the epitope recognized by the anti-Met antibody fragment to prevent binding of the anti-Met antibody fragment thereto, preferably the extracellular portion of human Met having the amino acid sequence set forth in SEQ ID No.: 14.

As used herein, the expression "the extracellular portion of human Met is capable of binding to human HGF in a stable manner" means that extracellular portion of human Met binds to HGF with a calculated Kd not higher than 100 nM.

The expression "the extracellular portion of human Met contains at least one amino acid mutation at the epitope recognized by the anti-Met antibody fragment", as used herein, means the presence of one or more mutations (i.e. amino acid substitutions and/or deletions and/or insertions) within the extra-cellular portion of Met, able to induce a modification within the extra-cellular portion of Met that prevents the engagement of the above region by the anti-Met antibody variable domains. The skilled man in view of his common general knowledge (represented i.a. by the possibility to generate a cDNA including a single nucleotide change in a given DNA sequence using specific primers during DNA duplication; see Maniatis T. Molecular cloning: A laboratory manual Cold Spring Harbor Laboratory, 1982) does not need further details about the realization of a mutated form of the extracellular portion of human Met retaining the ability to bind to human HGF but not to the anti-Met antibody fragment. The present invention must not therefore be interpreted as encompassing only the mutated extra-cellular portion of human Met as disclosed herein (i.e. SEQ ID No.: 14), since the skilled man in view of the common general knowledge can produce further mutated versions of the extra-cellular portion of human Met having SEQ ID No.: 13 that prevent the bind of the anti-Met antibody thereto.

The terms "SEMA", "PSI", "IPT-1", "IPT-2", "IPT-3" and "IPT-4" refer to the Met domains constituting the extracellular region of Met. Such domain names belong to the common general knowledge of a skilled man as represented i.a. by [23,24]. SEMA domain is a protein interacting module in common with semaphorins and plexins encompassing the region comprised between amino acids 25-516 of Met (SEQ ID No.: 13); PSI is a domain in common with Plexins, Semaphorins, and Integrins encompassing the region comprised between amino acids 519-561 of Met (SEQ ID No.: 13); the IPT domain—repeated four times—is a region Immunoglobulin-like in common with Plexins and Transcription factors, encompassing the region comprised between amino acids 563-934 of MET (SEQ ID No.: 13). In detail, IPT repeat 1 covers the amino acid positions 563-656 of SEQ ID No.: 13, IPT repeat 2 covers the amino acid positions 657-740 of SEQ ID No.: 13, IPT repeat 3 covers the amino acid positions 741-837 of SEQ ID No.: 13, IPT repeat 4 covers the amino acid positions 838-934 of SEQ ID No.: 13.

The present invention further concerns the therapeutic use of the anti-Met antibody fragment as disclosed herein, optionally in combination with an extracellular portion of human Met as disclosed herein, for use in the treatment of a patient suffering from a tumor and/or metastasis, wherein the patient carries genetic alterations of the MET gene.

The present invention further concerns the therapeutic use of the anti-Met antibody fragment as disclosed herein in combination with an extracellular portion of human Met as disclosed herein for use in the treatment of a patient suffering from a tumor and/or metastasis, wherein the patient carries a wild-type MET gene.

In one aspect, the invention provides a method of treating a tumor and/or metastasis in a subject, said method comprising administration to the subject of an effective amount of the anti-Met antibody fragment, optionally in combination with an extracellular portion of human Met, whereby said condition is treated.

In one aspect, the invention provides a method of inhibiting the growth of a cell that expresses Met, said method comprising contacting said cell with the anti-Met antibody fragment disclosed herein, optionally in combination with an extracellular portion of human Met of the invention, thereby causing an inhibition of growth of said cell.

In one aspect, the invention provides a method of therapeutically treating a mammal having a cancerous tumor and/or metastasis, said method comprising administration to said mammal of an effective amount of the anti-Met antibody fragment disclosed herein, optionally in combination with an extracellular portion of human Met, thereby effectively treating said mammal.

In one aspect, the invention provides a method for treating a cell proliferative disorder, said method comprising administration to a subject in need of such treatment of an effective amount of the anti-Met antibody fragment object of the present disclosure, optionally in combination with an extracellular portion of human Met, thereby effectively treating or preventing said cell proliferative disorder.

In one aspect, the invention provides a method of therapeutically treating a tumor and/or metastasis in a mammal, wherein the growth of said tumor is at least in part dependent upon a growth potentiating effect of the Met/HGF system, as the consequence of either an increase in cell proliferation, a protection from apoptosis, or both. Said method comprises contacting a tumor cell with an effective amount of the anti-Met antibody fragment, optionally in combination with an effective amount of an extracellular portion of human Met of the invention, thereby effectively treating said tumor and/or metastasis.

The tumor, that can be effectively treated with the anti-Met antibody, optionally in combination with an extracellular portion of human Met, is selected from breast, colorectal, lung, colon, pancreatic, prostate, ovarian, cervical, central nervous system, renal, hepatocellular, bladder, gastric, head and neck tumor cell, papillary carcinoma (e.g. the thyroid gland), melanoma, lymphoma, myeloma, glioma/glioblastoma (e.g. anaplastic astrocytoma, multiforme glioblastoma, anaplastic oligodendroglioma, anaplastic oligodendroastrocytoma), leukemia cell, sarcoma, rhabdomyosarcoma, or a tumor from a Cancer of Unknown Primary origin (CUP).

In one embodiment, a cell that is therapeutically targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic a cell. In further embodiment, a cell that is targeted in a method of the invention is a Met expressing cell belonging to the microenvironment sustaining the tumor and/or the metastasis.

The present inventors demonstrated that the One-Arm structure, obtained by selected point mutations of the CH3 domain and resulting in efficient Fc heterodimerization, originates an antibody into a monovalent form.

Monovalency is essential to avoid the eventual agonistic activity of the DN30 due to the bivalent native structure of the antibody.

Unexpectedly and surprisingly the present inventors discovered that one of the humanized One-Arm format of the DN30 (i.e. hOA-DN30-c103E08) displays strong inhibitory properties in vitro and in vivo.

In vitro hOA-DN30-c103E08 shows a superior activity as compared to the corresponding chimeric form (named in the following as "chOA-DN30") and to all the other humanized One-Arm derivatives herein disclosed (named "hOA-DN30 antibodies") (see Material and Methods section for a detailed description of all the One-Arm antibodies derived from DN30). Unexpectedly hOA-DN30-c103E08 binds to Met with a higher affinity as compared to the other OA-DN30 antibodies tested, either chimeric or human. Unpredictably, the inventors found that the shedding response is potentiated by increasing the affinity of the DN30 antibody for Met. Consequently, the inhibition of Met activation, measured as amount of phosphorylated Met receptors, was stronger. These activities translate into a repression of Met-mediated biological responses. Impairment of MET-addicted tumor cell growth occurs at very low dose; the hOA-DN30-c103E08 $IC_{50}$ is the lowest among all those measured for the OA-DN30 antibodies included in the analysis, either chimeric or human. A better inhibition of tumor cell growth can be due to a more extensive block of cell proliferation, and/or to a more pronounced increment of cytotoxicity.

The hOA-DN30-c103E08 shows improved therapeutic potential also in vivo. This is expected if the comparison is done with MvDN30, a molecule that, due to its low molecular weight, is subjected to high kidney clearance. The poor pharmacokinetic properties of MvDN30 considerably affect the performance of the molecule in the in vivo experimental models.

One can consider that reaching a molecular weight higher than the cut-off of renal clearance is per se sufficient to elicit the best therapeutic response, but this is not the case. In fact, the results obtained with the DCD-1 and DCD-2 derivatives of the DN30 mAb-recombinant molecules with increased size with respect MvDN30-clearly show that the pharmacokinetic profile is only partially improved and the therapeutic response is limited to a reduction of the tumor growth rate[8].

The superior activity of the hOA-DN30-c103E08 can in part be due to the presence of the Fc region that generates differences in the tissue/organ distribution of the antibody due to the binding to the Fc Receptor, thus providing a highly favourable pharmacokinetic profile.

The positive aspects related to the in vivo stability due to the presence of the Fc region have been already discussed and disclosed during Onartuzumab application. This is an anti-Met antibody designed in the One-Arm format[25]. Nevertheless this antibody is produced in bacteria, thus is not glycosylated. Consequently, it lacks the ability to activate Antibody Dependent Cellular Cytotoxicity (ADCC) and/or Complement Dependent cytotoxicity (CDC). On the contrary, hOA-DN30-c103E08 is produced in mammalian cells and therefore, it must be considered fully able to elicit Fc effector functions.

hOA-DN30-c103E08 is different from Onartuzumab also for the mechanism of action. While the first antibody induces Met receptor shedding, wiping out Met from the cell surface and sponging HGF in the extracellular environment, the second one competes with HGF for Met binding. As result, hOA-DN30 inhibits Met independently from the mechanisms that sustain the aberrant activation of the onco-receptor, while Onartuzumab is effective only in the cases of ligand-dependent activation.

The presence of the Fc region cannot be of the responsible notable improvement of the therapeutic response in vivo obtained by the hOA-DN30-c103E08, as this domain is present in all the humanized and chimeric One-Arm antibody tested. What the humanized and the chimeric One-Arm antibodies do not share are the variable regions, in which lies the binding site of the antibodies. In particular, the DN30 CDRs—identical in all the derivatives—are inserted in the frame regions. These parts of the antibody, even if not directly involved in the formation of the binding pocket, include particular amino acids, called Vernier residues[26], that could influence the final conformation of the CDR structures and therefore could determine the final affinity of the antibody for the antigen. The DN30 CDRs in combination with the frame sequences, i.e. the sequences of the heavy and light variable domains, of the c103E08 originate an anti-Met antibody with a stronger affinity probably because the sequence combination generates a binding pocket fitting better with the corresponding epitope on the Met receptor. A more robust interaction between the antibody and Met further implements the shedding of the receptor and the consequent impairment of Met-mediated biological responses. This, conjugated with the improved plasma stability due to the One-Arm format, gives rise to an antibody—i.e. the c103E08—with unexpected superior activity against MET-addicted/driven cancers.

Data reported in Basilico et al. 27 show that concomitant targeting of both HGF and Met gives rise to a higher therapeutic robustness in the treatment of tumors and/or metastasis. The experimental data witnessed herein unexpectedly show that inhibition of the MET/HGF axis by means of hOA-DN30 in combination with DecoyMet$^{K842E}$ is superior to the one obtained upon the application of MvDN30 in combination with DecoyMet$^{K842E}$. In fact, comparing the results obtained in the invasion assay (here reported in FIG. 9) with the ones published in Basilico et al. [27], hOA-DN30 abrogates the HGF-driven invasion of cancer cells, while a residual activity is still present if MvDN30 is part of the combination.

Cancer cells without MET genetic alterations exploit the 'physiological' program triggered by the MET oncogene as an 'expedient' to boost the malignant phenotype and to unleash the invasive metastatic phenotype in response to stress conditions such as hypoxia, ionizing radiation or chemotherapy. 'Expedience' requires stimulation of wild-type MET by its ligand HGF. The data provided herein show that, in conditions of MET 'expedience', a concomitant intervention hitting both sides of the MET/HGF axis results in improved inhibitory activity. The hOA-DN30-cl03E08 induces the physical removal of MET from the cell surface by 'shedding' of the ectodomain. The latter is released in the extracellular environment and acts as 'decoy' for HGF. Exogenous supply of recombinant DecoyMet reinforces the HGF-sequestering activity of the endogenous DecoyMet generated by hOA-DN30-c103E08. The combination of hOA-DN30-c103E08 and DecoyMet$^{K842E}$ acts simultaneously on Met-expressing cancer cells and on HGF-secreting tumor stroma. This allows optimal blockade of the HGF-driven Met signalling and thus represents a reliable therapeutic option for a large cohort of patients carrying tumors expressing wild-type MET that rely on MET for sustaining the invasive/metastatic phenotype.

The proteins disclosed herein (i.a. the humanized anti-Met antibody and the extracellular portion of human Met) can be easily manufactured either in the form of proteins or in the form of nucleic acid molecules encoding the proteins by a skilled man in view of the common general knowledge of the field related to the recombinant DNA technology, as represented i.a. by Maniatis T. Molecular cloning: A laboratory manual Cold Spring Harbor Laboratory (1982). For example, the following standard procedure can be followed: (i) synthesis of the corresponding cDNA sequences, (ii) insertion of the cDNAs into a plasmid suitable for expression in mammalian by conventional recombinant DNA methods, (iii) transient or stable co-transfection with the above mentioned plasmids of a mammalian cell line, (iv) collection of the culture supernatant, (v) purification by affinity chromatography of the recombinant protein.

Therapeutic compositions comprising the active ingredient(s) of the instant invention, i.e. the humanized anti-Met antibody fragment alone or in combination with an extracellular portion of human Met, can be prepared with physiologically acceptable carriers, excipients, or stabilizers (Remington's Pharmaceutical Sciences 16th edition, Osol, A. Ed., 1980), in the form of aqueous solutions, lyophilized, or other dried formulations. Acceptable carriers, excipients, or stabilizers are nontoxic to recipients at the dosages and concentrations employed, and include buffers; antioxidants; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates; chelating agents; sugars; salt-forming counter-ions; metal complexes and/or non-ionic surfactants. The formulations may also contain other active compound(s) as necessary for the particular indication being treated, preferably those with complementary activities that do not adversely affect the therapeutic activity of hOA-DN30 alone or in combination with the extracellular portion of human Met. Such molecules are suitably present in combination in amounts that are effective for the purpose intended.

The active ingredient(s) may also be entrapped in microcapsules prepared by means of techniques disclosed i.a. in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the active ingredients of the invention, which matrices are in the form of shaped articles, e.g. films, or microcapsule.

The active ingredient(s) of the invention can be used either alone or in combination with another antibody, small molecule tyrosine kinase inhibitors, chemotherapeutic agent(s) (including cocktails of chemotherapeutic agents), other cytotoxic agent(s), anti-angiogenic agent(s), cytokines, and/or growth inhibitory agent(s). Such combined therapies noted above include combined administration (where the two or agents are included in the same or separate more formulations), and separate administration, in which case, administration of hOA-DN30 can occur prior to, and/or following, administration of the adjunct therapy or therapies.

The active ingredient(s) of the present invention (and adjunct therapeutic agent(s)) is (are) administered any means, by suitable including parenteral, subcutaneous, intraperitoneal, intrapulmonary, and intranasal, and, if desired for local treatment, intralesional administration. The active ingredient(s) of the instant invention can be suitably administered by pulse infusion, particularly with declining doses of the active ingredients. Dosing can be by any suitable route, e.g. by injections, such as intravenous or subcutaneous injections, depending in part on whether the administration is brief or chronic.

The active ingredient(s) of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The active ingredient(s) of the invention need not be, but may optionally be, formulated with one or more agents currently used to prevent or treat the disorder in question. The effective amount of such other agents depends on the amount of active ingredient(s) of the invention present in the formulation, the type of disorder or treatment, and other factors discussed above. These are generally used in the same dosages and with administration routes as used hereinbefore or about from 1 to 99% of the heretofore employed dosages.

For the treatment of disease, the appropriate dosage of the active ingredient(s) of the invention (when used alone or in combination with other agent(s) such as chemotherapeutic agent(s)) will depend on the type of disease to be treated, the severity and course of the disease, whether the active ingredients are administered for preventive or therapeutic purposes, the patient's clinical history and response to the active ingredients of the invention are duly taken into consideration, and at the discretion of the attending physician.

hOA-DN30 is suitably administered to the patient at one time or over a series of treatments. Depending on the type and severity of the disease, about 1 mg/kg to 30 mg/kg of antibody is an initial candidate dosage for administration to patient, whether, for example, by one or more separate administrations, or by continuous infusion. One typical daily dose might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody fragment would be in the range from about 0.05 mg/kg to about 20 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays. With respect to the combination therapy, the extracellular portion of human Met is preferably delivered at the same time of hOA-DN30 and dosed in proportion to hOA-DN30, preferentially but not limited to, the molar ratio 1:1 hOA-DN30: DecoyMet$^{K842E}$ depending on the type and severity of the disease.

Results

Generation of the Chimeric and Humanized One-Arm Formats of the DN30 Antibody.

Through classical molecular biology techniques, the present inventors substituted the constant domains of the DN30 mAb heavy and light chains with constant domains derived from human immunoglobulins. The light chain constant domain was substituted with the human kappa type domain, (the one more represented in the natural human antibodies), while the heavy chain constant domains were substituted with the homologous domains derived from the human IgG1 (the one that can induce ADCC/CDC).

Humanization of the DN30 mouse antibody has been done by Fair Journey Biologics using a phage display library approach. They started from the identification of deviating FR (frame) residues and the analysis of the closest human V germline, chosen from germlines with identical canonical fold combination for CDR1-CDR2, using available tools and databases: abYsistool from Dr. Andrew Martin at UCL plus, http://www.bioc.uzh.ch/plueckthun/antibody/and http://www2.mrc-lmb.cam.ac.uk/vbase/. Upon generation of phage display libraries—in which randomization of the VH and VL region has been performed—four affinity-driven phage display rounds of selection have been done. At the end of the process, the DN30 humanized variants with the highest human identity and homology were selected. Variable regions were linked through classical molecular biology techniques to the constant domain sequences derived from human immunoglobulins, i.e. human kappa light chain and IgG1 heavy chain constant domains.

To format the chimeric and the humanized antibodies One-Arm single chain form, into the specific amino acid modifications have been inserted in the CH3 region to produce the 'knob into hole' structure[28, 29]; one CH3 domain carries the knob mutation: $^{389}$T→W, the other CH3 domain carries the hole mutations: $^{389}$T→S; $^{391}$L→A; $^{438}$Y→V. CDNAs encoding for the chimeric or humanized light chains, the chimeric or humanized heavy chains (mutated in the CH3 domain) and the human Fc domain (mutated in the CH3 domain) were cloned into expression plasmids and then expressed into eukaryotic cells. Assembled One-Arm antibodies were purified from cell culture supernatants by affinity chromatography and gel filtration. FIG. 1 shows a schematic drawing of the DN30 derivatives and the SDS-Page separation under not reducing and reducing condition of the purified recombinant OA-DN30 molecules.

DN30 One-Arm Antibodies Recognize Met with High Affinity.

Figure 2:
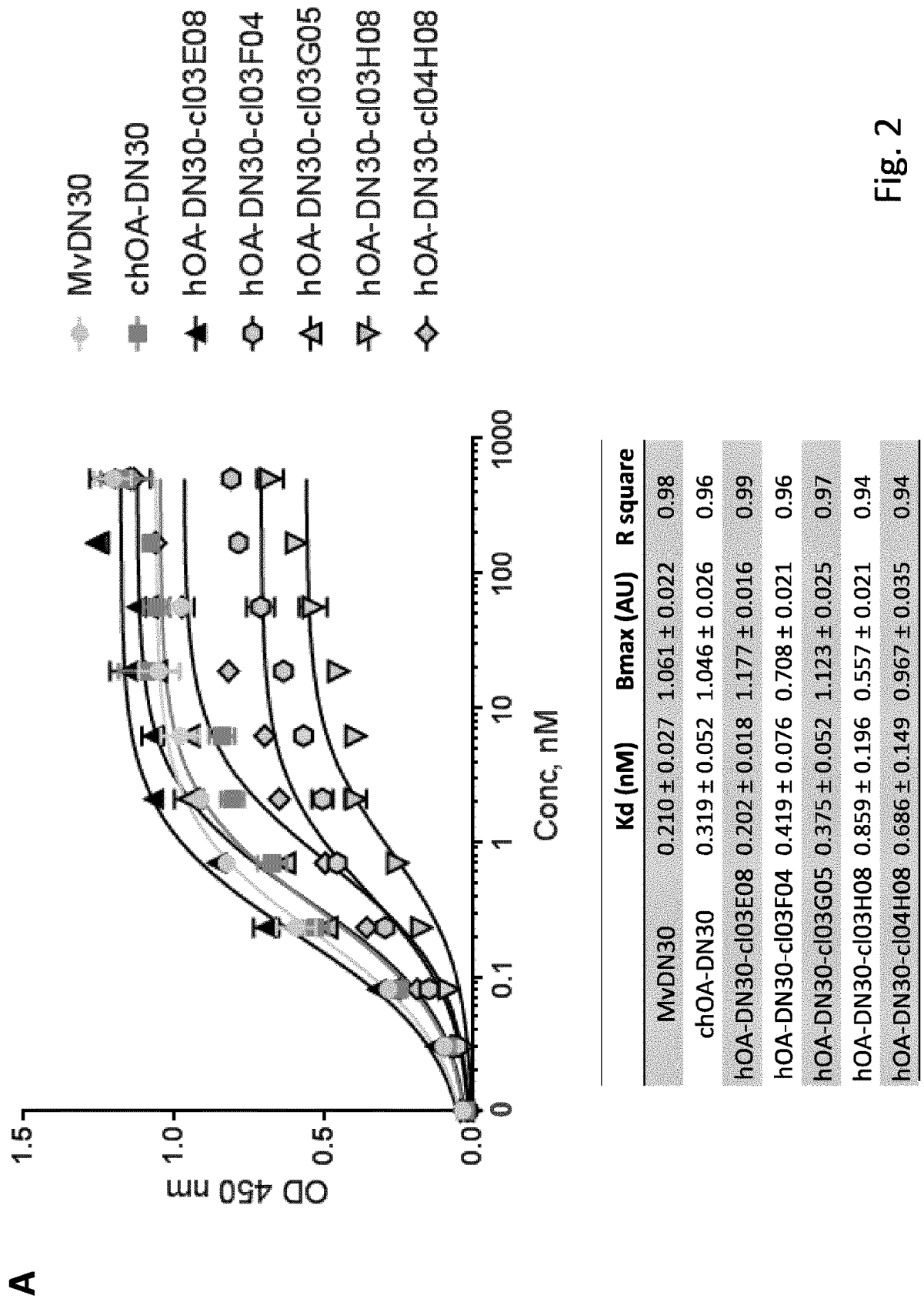
FIG. 2: Binding to Met of the monovalent DN30-derived molecules. (A) ELISA binding analysis of MvDN30, chOA-DN30, hOA-DN30 antibodies (liquid phase) to a human Met-Fc chimera (solid phase). (B) ELISA binding analysis of hOA-DN30-c103E08 (liquid phase) to Met-Fc chimera (solid phase); Met of human, murine, rat, monkey origin were included in the assay. Binding was revealed using anti-human k chain antibodies. O.D.: Optical Density; AU: arbitrary units. Each point is the mean of triplicate values; bars represent standard deviations. Tables below the graphs report Kd values, binding maximum values (Bmax), and the fitting score (R2). (C) Flow-cytometer analysis of hOA-DN30-c103E08 binding to Met expressed at the surface of a panel of cell lines derived from different species (EBC-1, human lung cancer; C2C12 mouse muscle myoblasts; H9C2 rat cardiac myoblasts; MDCK dog kidney cells; Cos-7 monkey kidney cells). The new molecules bind to human Met-Fc with high affinity; the antibody cross-reacts with human, rat, dog, and monkey Met.

Purified One-Arm forms of the chimeric or humanized DN30 antibodies were analysed for binding to the Met receptor by an ELISA assay. As reference, the chimeric DN30 Fab (MvDN30) 12 was included in the analysis. The assay was assembled to include Met-Fc in solid phase and the DN30 derivatives in liquid phase. Binding was revealed using anti-human k chain antibodies. Data showed that both the chimeric and the humanized antibodies bind to Met, the hOA-DN30-c103E08 showing the highest affinity (FIG. 2A).

Analysis of hOA-DN30-c103E08 Cross-Reactivity with Non-Human Met Receptors.

The present inventors analysed the species cross reactivity of the hOA-DN30-c103E08 performing: (i) an ELISA assay with purified Met extracellular domains of human, mouse, rat, and monkey origin (FIG. 2B); (ii) a flow-cytometer analysis of antibody binding to surface Met expressed by cells of human, mouse, rat, dog and monkey origin (FIG. 2C). Results of the experiments showed that hOA-DN30-c103E08 binds Met of human, rat, dog, monkey origin, while the interaction with mouse Met was very weak.

DN30 One-Arm Antibodies do not Exert Agonistic Properties.

Figure 3:
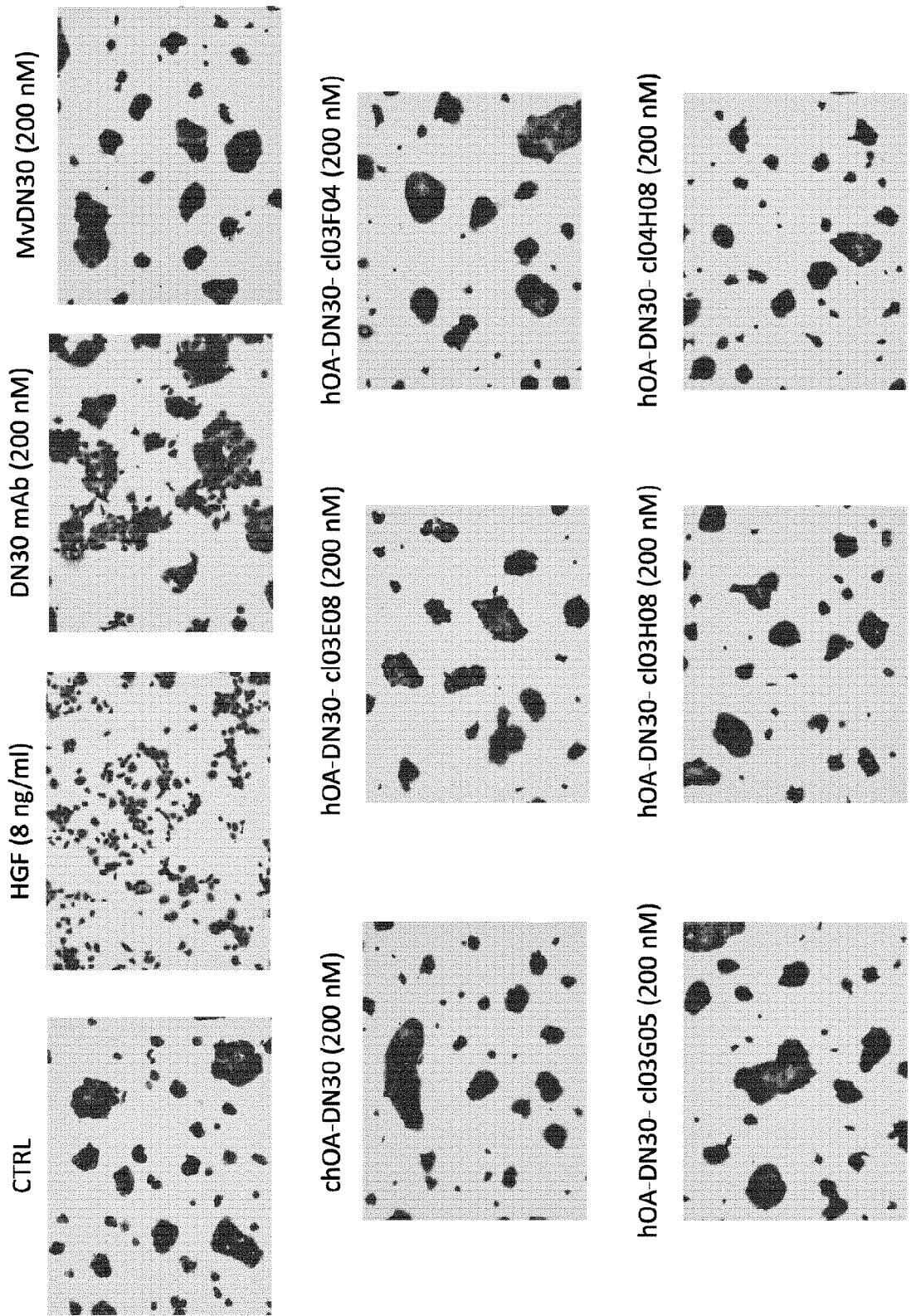
FIG. 3: Agonistic activity of the monovalent DN30-derived molecules. Scatter assay. HPAF-II cells were incubated for 24 with hrs the indicated concentration of HGF (Met ligand), DN30 mAb (partial agonist), MvDN30 (full antagonist) and the chimeric or humanized One-Arm antibodies. All the DN30-derived monovalent molecules do not induce cell scattering, a Met-mediated biological response.
Figure 4:
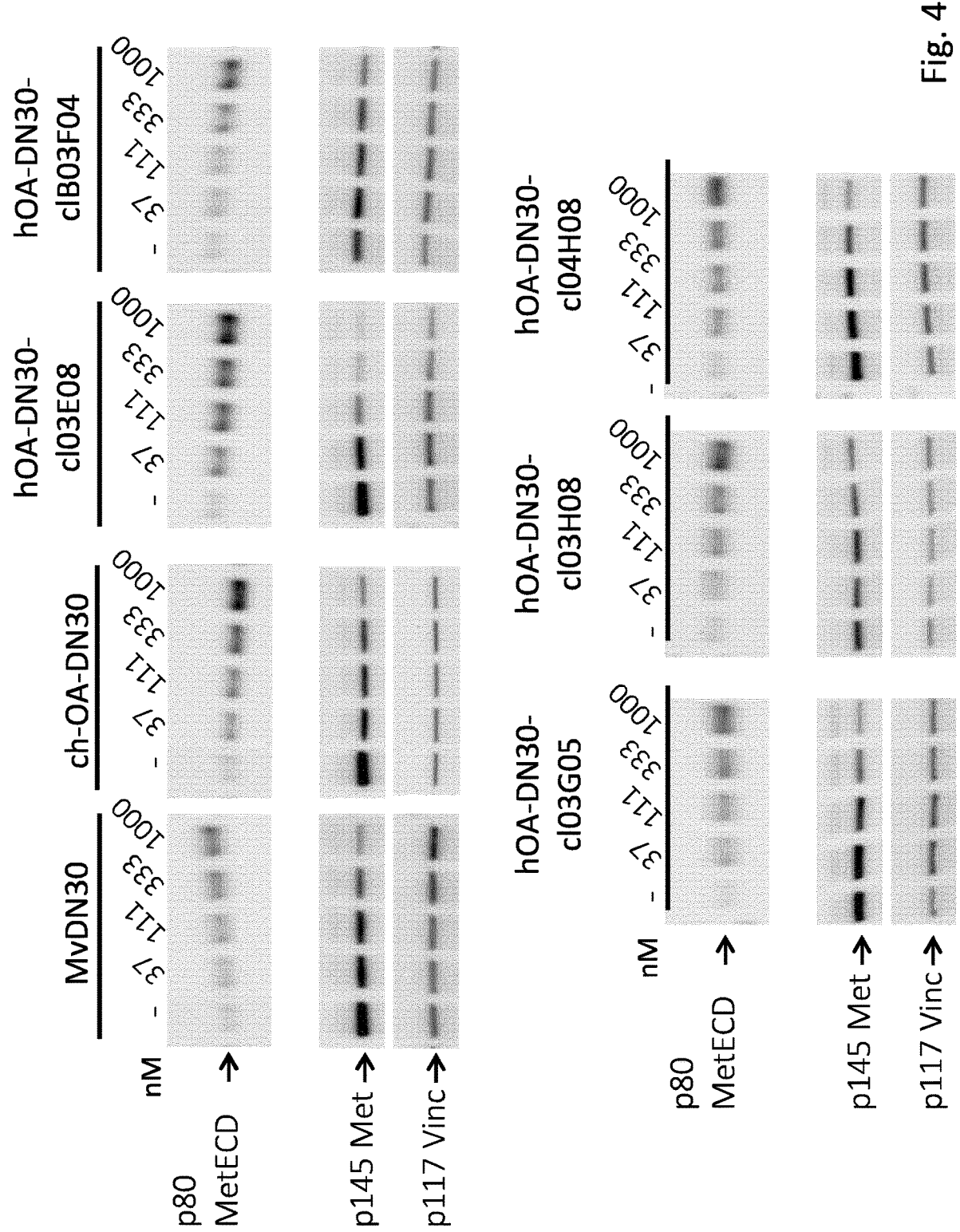
FIG. 4: Met shedding and down-regulation in cells treated by the monovalent DN30-derived molecules. A549 cells were incubated for 48 hrs in serum free medium with the indicated increasing concentration of MvDN30, chOA-DN30, or hOA-DN30 derivatives. Total Met levels were determined by Western blot analysis of cell extracts using anti-Met antibodies. The detected bands correspond to the mature form of the receptor (p145 Met). As a loading control, the filter was probed with an unrelated protein (vinculin). Met shedding was determined by Western blot analysis of conditioned medium using anti-Met antibodies. The detected bands correspond to the shed extracellular domain of the receptor (p80 Met ectodomain). The table reports pixel intensity quantification of each western blot band normalized on the corresponding vinculin signal, as measured by densitometry with ImageJ software. All the monovalent One-Arm antibodies downregulate Met and induce Met shedding.

The present inventors tested whether the new DN30 derivatives could display Met agonistic activity in a highly sensitive assay, the scatter assay. HPAF-II human pancreatic carcinoma cells, which represent a standard system for determining cell motility in response to HGF stimulation, were stimulated for 24 hrs with increasing concentrations of the antibody. As a positive control, HGF and bivalent DN30 mAb were included in the assay. While cells stimulated with the positive controls were clearly scattered, the phenotype of the cells treated with all the monovalent DN30 derivatives (MvDN30, chOA-DN30, and hOA-DN30 antibodies) was indistinguishable from the untreated ones (FIG. 3).

hOA-DN30 Potently Induces Met 'Shedding',

The present inventors also investigated whether hOA-DN30 maintained the ability to promote receptor shedding and downregulation. A549 cells were incubated with increasing concentrations of choA-DN30 and hOA-DN30 antibodies. As a reference, MvDN30 was included in the assay. After 48 hours, Met ectodomains released in the conditioned medium were scored by immunoblotting using a monoclonal antibody directed against the extracellular portion of Met. Total cellular levels of Met were also determined on cell lysates using the same antibody. This analysis revealed that all the OA-DN30 antibodies shedding, resulting in the release of soluble Met ectodomains in the extracellular space and physically removing Met from the cell surface (FIG. 4). Unexpectedly, the activity of the hOA-DN30-c103E08 was superior as compared with all the other DN30 derivatives included in the test.

hOA-DN30-c103E08 Strongly Inhibits Met Phosphorylation.

Figure 5:
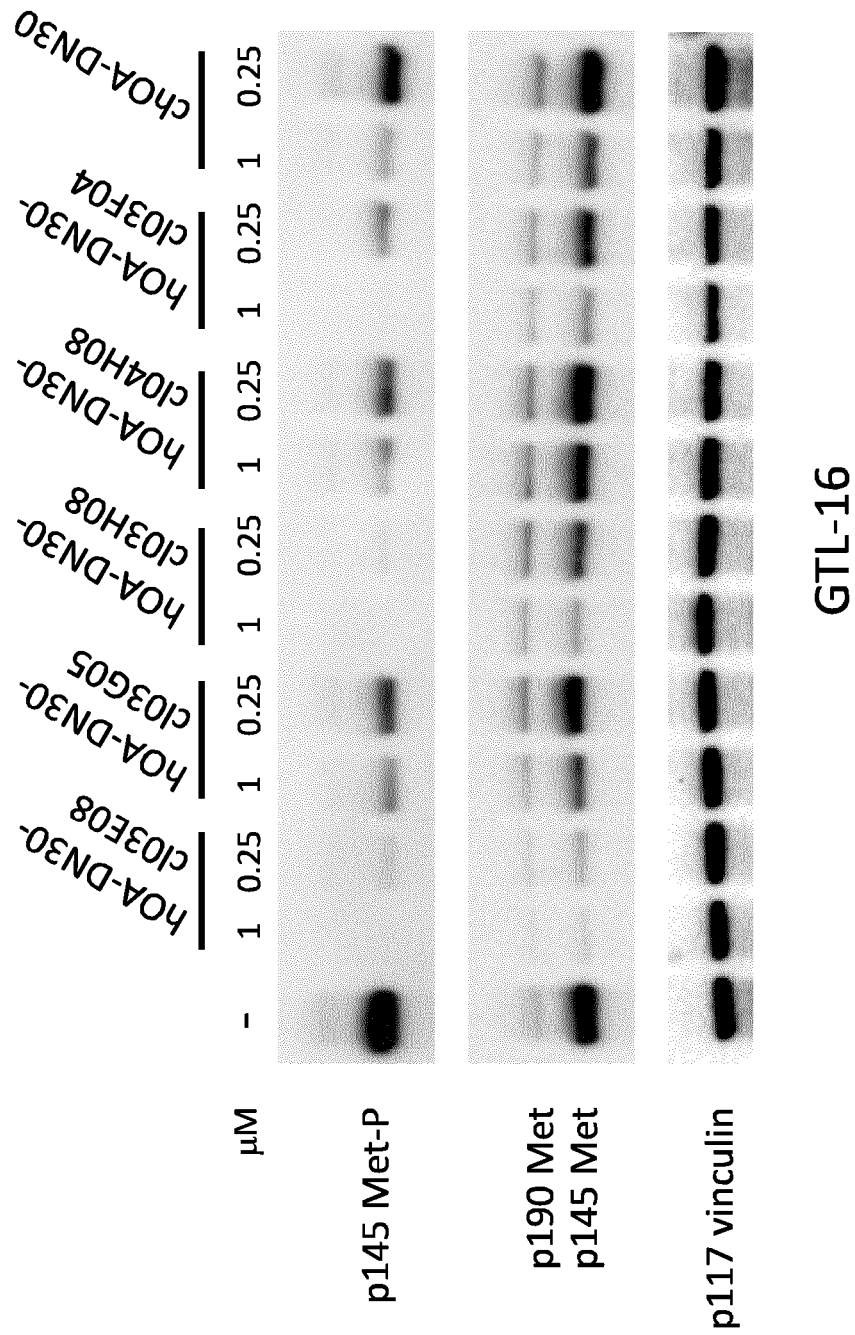
FIG. 5: Inhibition of Met-activation by the monovalent DN30-derived molecules. GTL-16 (MET-addicted cells carrying a constitutively active Met due to receptor overexpression sustained MET by gene amplification) were incubated for 24 hrs in serum free medium plus hOA-DN30 or chOA-DN30 antibodies (1000 or 250 nM). Met activation was determined in total cell lysates by Western blotting with anti-Met antibodies specific for the phosphorylated Tyr1234/1235 Met residues, the major phosphorylation site. The same blot was re-probed with anti-Met antibodies. To control protein loading, the filter was also probed with anti-vinculin antibodies. Chimeric and humanized One-Arm antibodies inhibit Met phosphorylation.

The present inventors investigated if the chOA-DN30 and the hOA-DN30 antibodies inhibited Met phosphorylation in cells derived from human carcinomas, i.e. GTL-16. These cells have a constitutive active Met as the consequence of receptor over-expression due to gene amplification. Met activation was determined by immunoblotting with anti-phosphoMet antibodies. As shown in FIG. 5, all the molecules impaired Met phosphorylation/activation, with a dose-response modality. hOA-DN30-c103E08, inducing the strongest impairment of Met levels in the cells, was the DN30 derivative more active.

hOA-DN30-c103E08 Powerfully Inhibits MET-Addicted Cell Growth.

Figure 6:
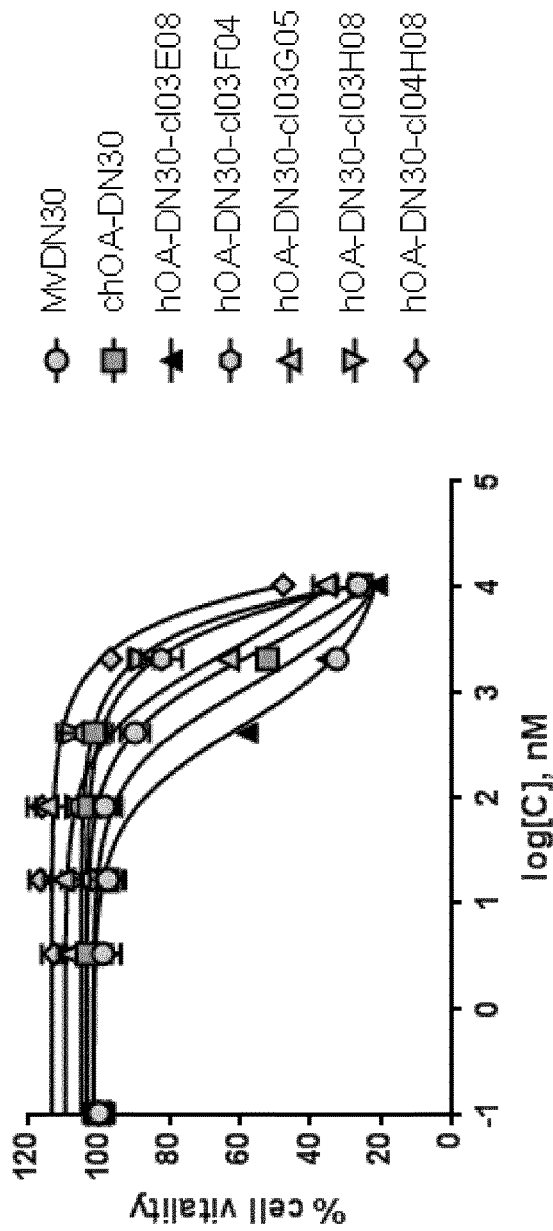
FIG. 6: Vitality of MET-addicted cells treated with the monovalent DN30-derived molecules. GTL-16 human gastric carcinoma cells were plated in 96 well plates in 10% FCS medium. After 24 hrs, cells were treated with increasing concentrations of MvDN30, chOA-DN30, or hOA-DN30 antibodies for a further 72 hrs. Number of cells was evaluated by Cell titer-glo. The plot represents the percentage of alive cells with respect to untreated control. Each point is the mean of triplicate values. The table reports the calculated $IC_{50}$ values and the fitting score (R2). One-Arm molecules inhibit cell growth of MET-addicted cells.

Cell growth (viability) can be impaired by a Met-inhibitor only in MET-addicted cells, which rely on Met-signalling for proliferation/survival. To test the activity of the DN30 derivatives, exponentially growing GTL-16 cells (MET-addicted gastric carcinoma cells) were incubated with increasing concentrations of chOA-DN30 or hOA-DN30 antibodies. MvDN30 was included in the assay as a positive control. After 72 hours, cell viability was determined using a luminescence-based ATP assay. All the DN30 derivatives inhibited MET-addicted cell growth in a dose-dependent manner (FIG. 6). hOA-DN30-c103E08 showed the highest inhibition, being the $IC_{50}$ 2.5 folds lower as compared to MvDN30, 5.4 folds lower as compared to the choA-DN30, and at least 5.2 folds lower as compared to the other hOA-DN30 antibodies (see table in FIG. 6).

hOA-DN30-c103E08 is Highly Effective in Blocking Proliferation and in Inducing Cytotoxicity in MET-Addicted Cells.

Figure 7:
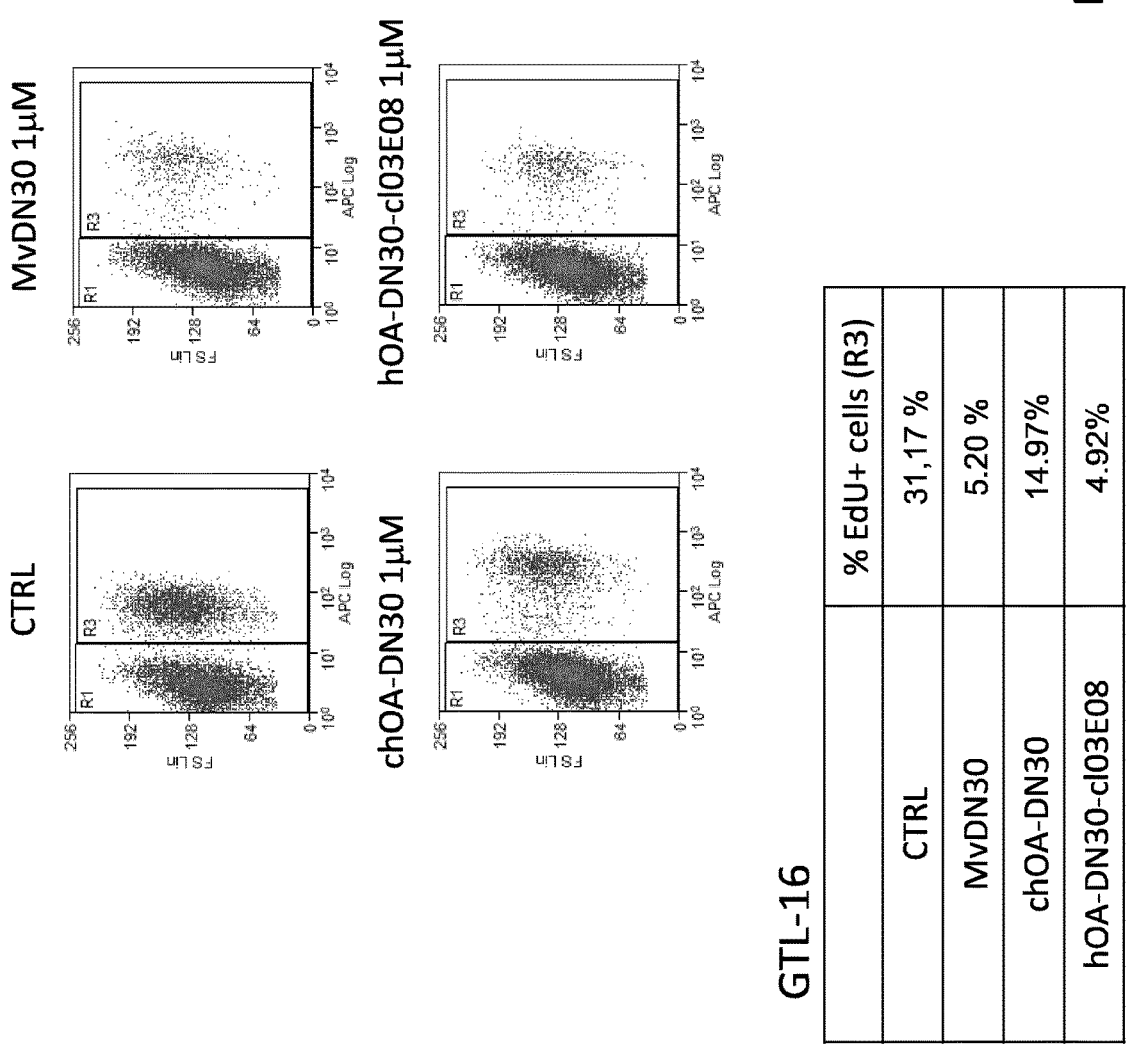
FIG. 7: Proliferation and death of MET-addicted cells induced by treatment with the monovalent DN30-derived molecules. (A) Proliferation assay: GTL-16 human gastric carcinoma cells were plated in 6 well plates in 10% FCS medium. After 24 hrs, cells were treated with a fixed concentration (1 µM) of MvDN30, chOA-DN30, or hOA-DN30-c103E08 for a further 48 hrs. EdU (10n µM) was then added to the culture medium for a further 2 hrs. Percentage of cells in S phase was determined by cytofluorimeter analysis following the procedure of the Click-iT EdU Flow Cytometry assay. The plots represent the cells negative and positive for the APC staining (EdUt, S phase cells). Table reports percentage of cells in S phase. (B) Cytotoxicity Assay: GTL-16 human gastric carcinoma cells were plated in 96 well plates in 10% FCS medium. After 24 hrs, cells were treated with increasing concentrations of MvDN30, choA-DN30, or hOA-DN30-c103E08 for a further 48 hrs. Cell cytotoxicity was evaluated by Cell-Tox green assay. The graphs represent the increment of cytotoxicity respect to untreated control. Each point is the mean of triplicate values. The table reports the calculated EC50 values, and the fitting score (R2). One-Arm molecule efficiently block proliferation and induce cytotoxicity in MET-addicted cells.

To further analyze the mechanisms underlining the inhibition of MET-addicted cell growth exerted by the DN30 derivatives, the inventors evaluated cell proliferation and cell cytotoxicity, comparing MvDN30, chOA-DN30, and hOA-DN30-c103E08. GTL-16 cells were incubated with a single dose (1 µM) of the DN30 derivatives and cell proliferation was assessed by measuring the incorporation of EdU—a thymidine analogous—by the cells during the S phase of the cell cycle, with the ClickIT Edu flow cytometry assay. MvDN30 was included in the assay as a positive control. This analysis revealed that DN30 derivatives affected proliferation, as the percentage of treated cells in S-phase was dramatically reduced as compared with control. In particular, the most effective molecule was hOA-DN30-c103E08, where only 4.9% of cells were still proliferating (84.2% reduction versus control). The proliferating cells in the population treated with chOA-DN30 were the 14.97% (52% reduction versus control) (FIG. 7A).

To test if DN30 derivatives induced only a block of proliferation or if they caused also cytotoxicity, exponentially growing MET-addicted GTL-16 cells were incubated with increasing concentrations of choA-DN30 or hOA-DN30-c103E08. MvDN30 was included in the assay as a positive control. After 72 hours, cytotoxicity was determined adding CellTox™ Green dye to the cells and measuring the fluorescence of the cells that is directly proportional to the number of dead cells. All the DN30 derivatives induced cytotoxicity in GTL-16 cells in a dose-dependent manner (FIG. 7B). hOA-DN30-c103E08 showed the highest induction, being the $EC_{50}$ 1.3 and 6.1 folds lower as compared to MvDN30 and chOA-DN30, respectively.

hOA-DN30-c103E08 Inhibits HGF-Induced Cell Motility, Alone and in Combination with DecoyMet.

Figure 8:
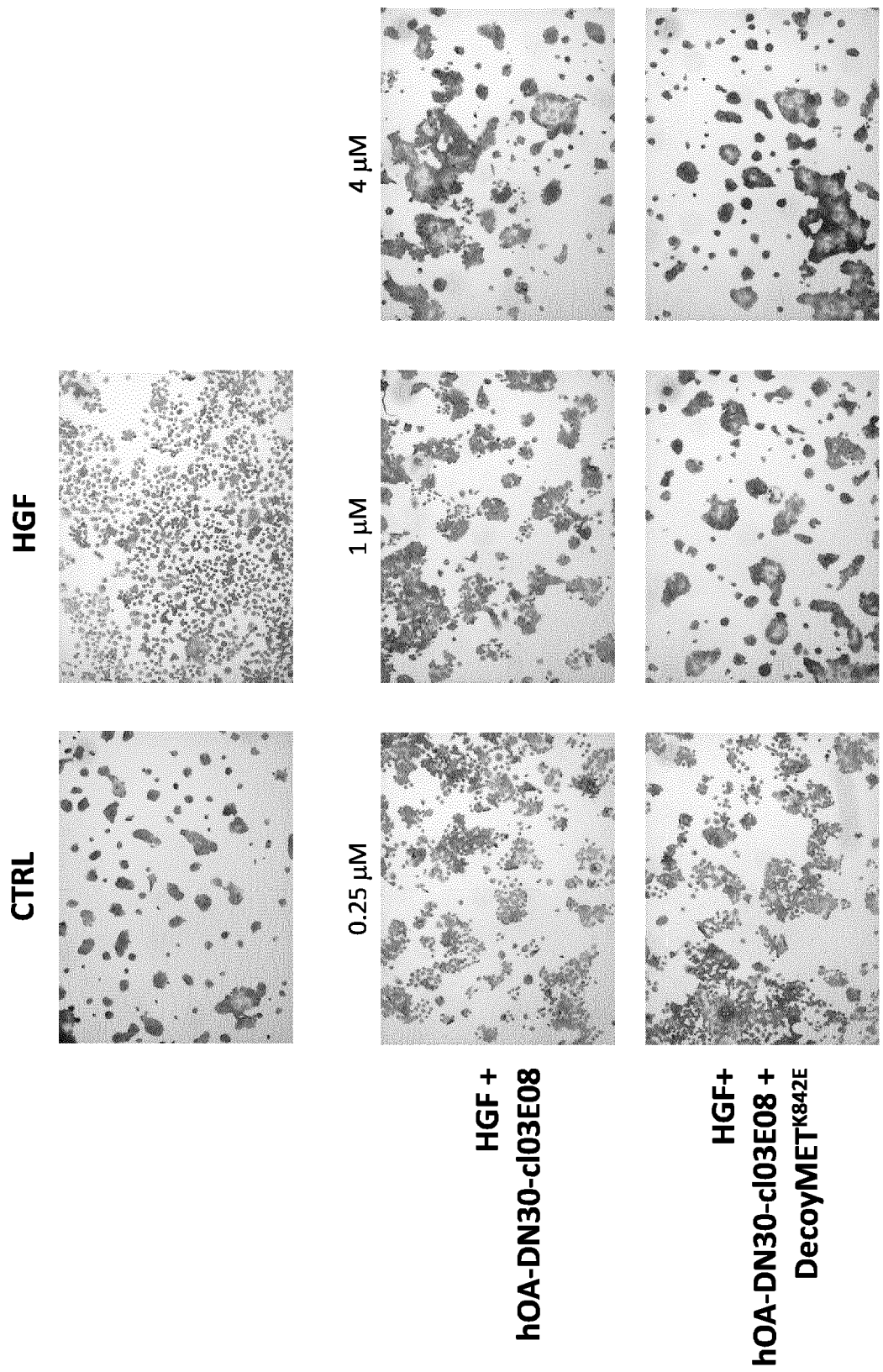
FIG. 8: HGF-induced cell motility in cells treated with hOA-DN30-c103E08. HPAF-II cells were pre-treated for 18 hrs with the indicated concentrations of hOA-DN30-c103E08 alone in or combination with DecoyMet$^{K842E}$ (same amount as hOA-DN30-c103E08) and then incubated for 24 hrs with HGF (6.25 ng/ml). hOA-DN30-c103E08 inhibits HGF-induced cell motility; the combination with DecoyMet$^{K842E}$ more efficiently counteracts the cell response.

The present inventors tested the ability of hOA-DN30-c103E08 to inhibit HGF-dependent cell motility of HPAF-II human pancreatic carcinoma cells. Cells were incubated or not with HGF and treated with increasing dose of hOA-DN30-c103E08. After 24 hrs, cell colonies were stained and analysed. In this assay, hOA-DN30-c103E08 strongly reduced HGF-dependent cell scattering (FIG. 8).

In the above cellular system it has been reported that a more effective inhibition of the HGF-induced biological response can be achieved by blocking concomitantly the ligand (HGF) the and receptor (Met) 27. The present inventors thus tested if hOA-DN30-c103E08 in combination with DecoyMet$^{K842E}$ induced a higher therapeutic response. DecoyMet$^{K842E}$ is a recombinant soluble receptor encompassing the whole extracellular region of Met carrying a mutation that abolishes the interaction with DN30; it binds HGF with high affinity and inhibits ligand-driven biological activities by sponging and neutralizing HGF and by forming heterodimers with intact Met receptors still present on the cell surface, rendering them inactive. With equimolar amount of the two molecules in combination, the effective dose completely reverting the scattered phenotype was 4 times lower than the dose of hOA-DN30-c103E08 alone able to eliciting a similar cell phenotype (FIG. 8).

hOA-DN30-c103E08 Inhibit HGF-Induced Cell Invasion, Alone and in Combination with DecoyMet.

Figure 9:
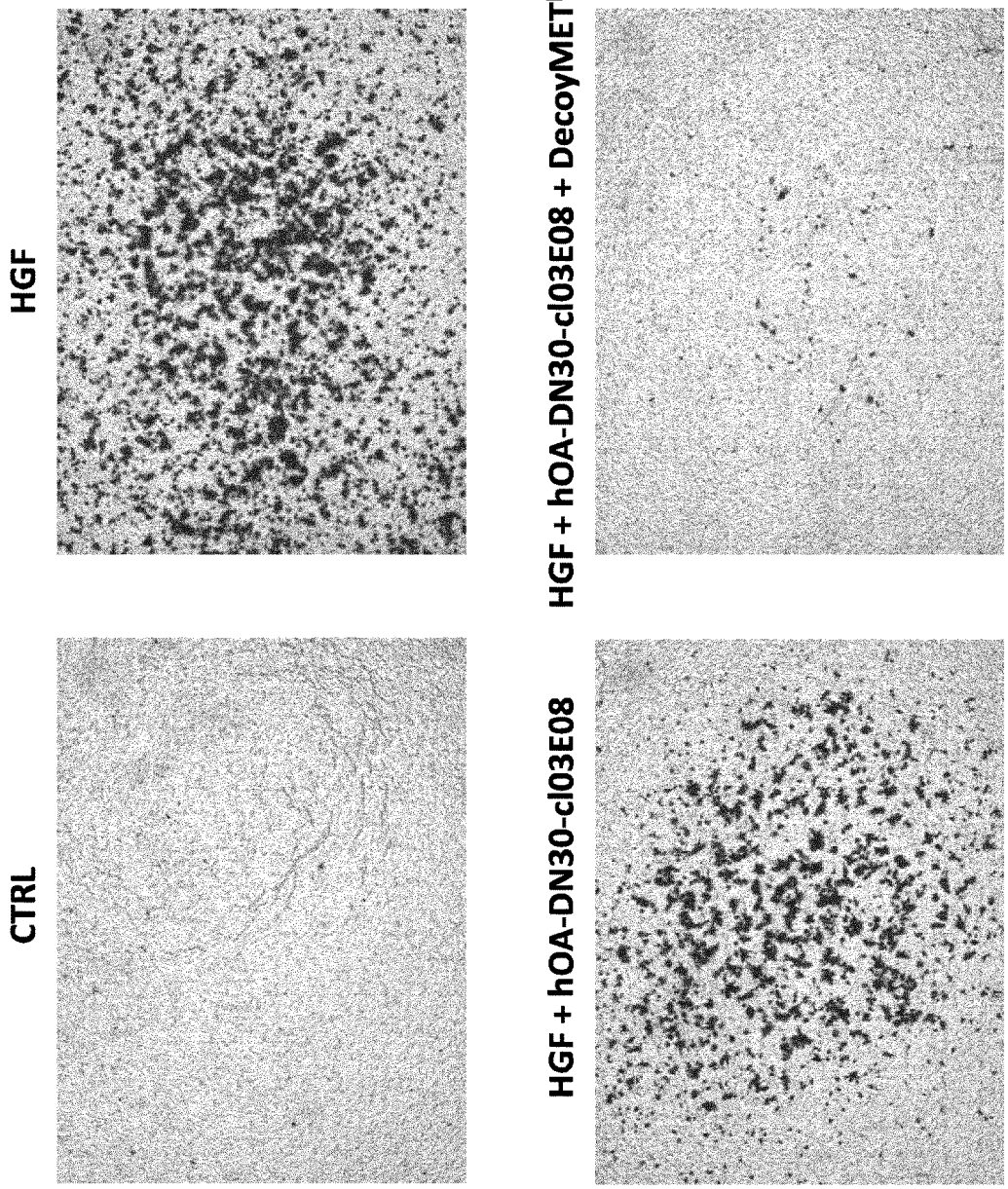
FIG. 9: Invasion of cells treated with hOA-DN30-c103E08. HPAF-II cells were plated in the upper chamber of transwell filters coated with matrigel in serum free medium with 0.5 µM of hOA-DN30-c103E08 alone or in combination with 1 µM of DecoyMetK842E. Medium with HGF (25 ng/ml) was added in the lower chamber. After 24 hrs, cells that migrated on the lower part of the filter were evaluated by staining and microscope observation. hOA-DN30-c103E08 inhibits HGF-induced cell invasion; the combination with DecoyMet$^{K842E}$ blocks the biological response.

The present inventors tested the ability of hOA-DN30-c103E08 to inhibit HGF-dependent cell invasion of HPAF-II cells. Cells were seeded in the upper chambers of transwell filters coated with matrigel in serum free medium with hOA-DN30-c103E08 (0.5 µM) alone or in combination with DecoyMet$^{K842E}$ (1 UM). The lower chambers were filled with medium containing HGF (25 ng/ml). After 24 hrs, cells migrating on the lower part of the filter were evaluated by staining and microscope observation. In this assay, hOA-DN30-c103E08 strongly reduced HGF-dependent cell invasion; the cell response was almost abolished by the combination hOA-DN30-c103E08 and DecoyMet$^{K842E}$ (FIG. 9).

hOA-DN30-c103E08 Revokes Interferon-Gamma Induction of PD-L1 Expression.

Programmed cell death ligand 1 (PD-L1) and programmed cell death receptor 1 (PD-1) are key modulatory molecules, known as immune-checkpoints, that play a central role at the interface between immune response and tumor microenvironment[30]. They may significantly impair the ability of the immune system to control tumor progression. The expression of PD-L1 by tumor cells is inducible and interferon gamma (IFNgamma) is the most potent inducer[31].

Figure 10:
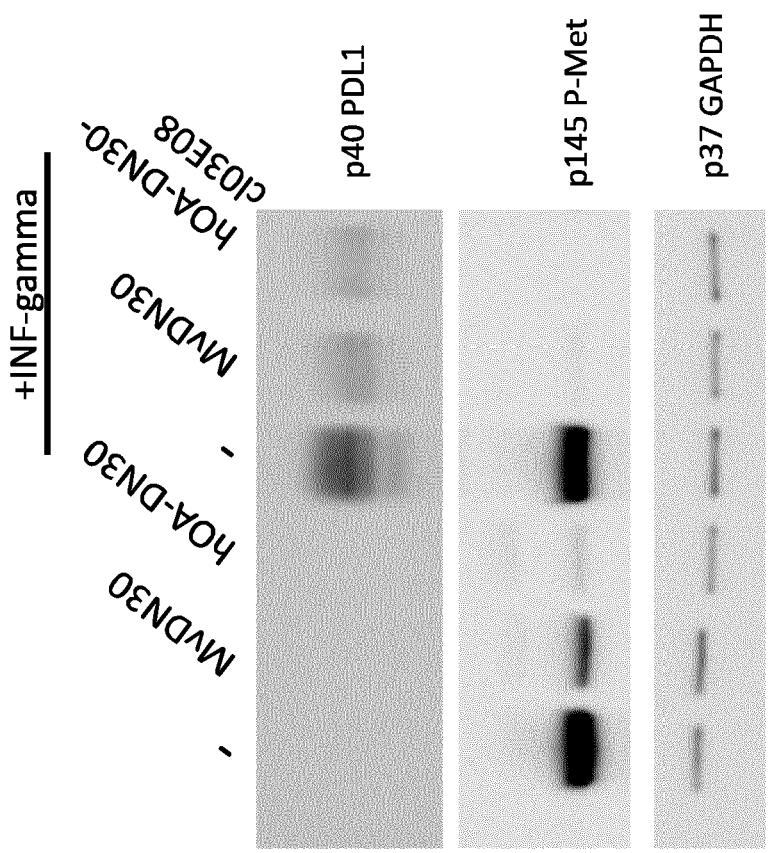
FIG. 10: Modulation of PD-L1 expression by hOA-DN30-c103E08. GTL-16 were cells treated with 50 ng/ml of IFN-gamma alone or in combination with 250 nM of hOA-DN30-c103E08. After 48 hrs, cells were lysed; PD-L1 expression and Met activation on total protein extracts were evaluated by Western blot. As a loading control, filters were probed with anti-GAPDH antibodies.

The present inventors analyzed if inhibition of Met by hOA-DN30-c103E08 could modulate the IFNgamma pathway and consequently PD-L1 regulation (FIG. 10). MET-addicted GTL-16 cells were treated with INFgamma for 48 hrs and analyzed for IFNgamma-inducible PD-L1 expression. In an unstimulated condition, PD-L1 was not detectable, while upon exposure to IFNgamma, it was consistently up-regulated. Treatment with hOA-DN30-C103E08 for 48 hrs significantly impaired the up-regulation of PD-L1 induced by IFNgamma.

hOA-DN30-c103E08 Profile In Vivo.

Figure 11:
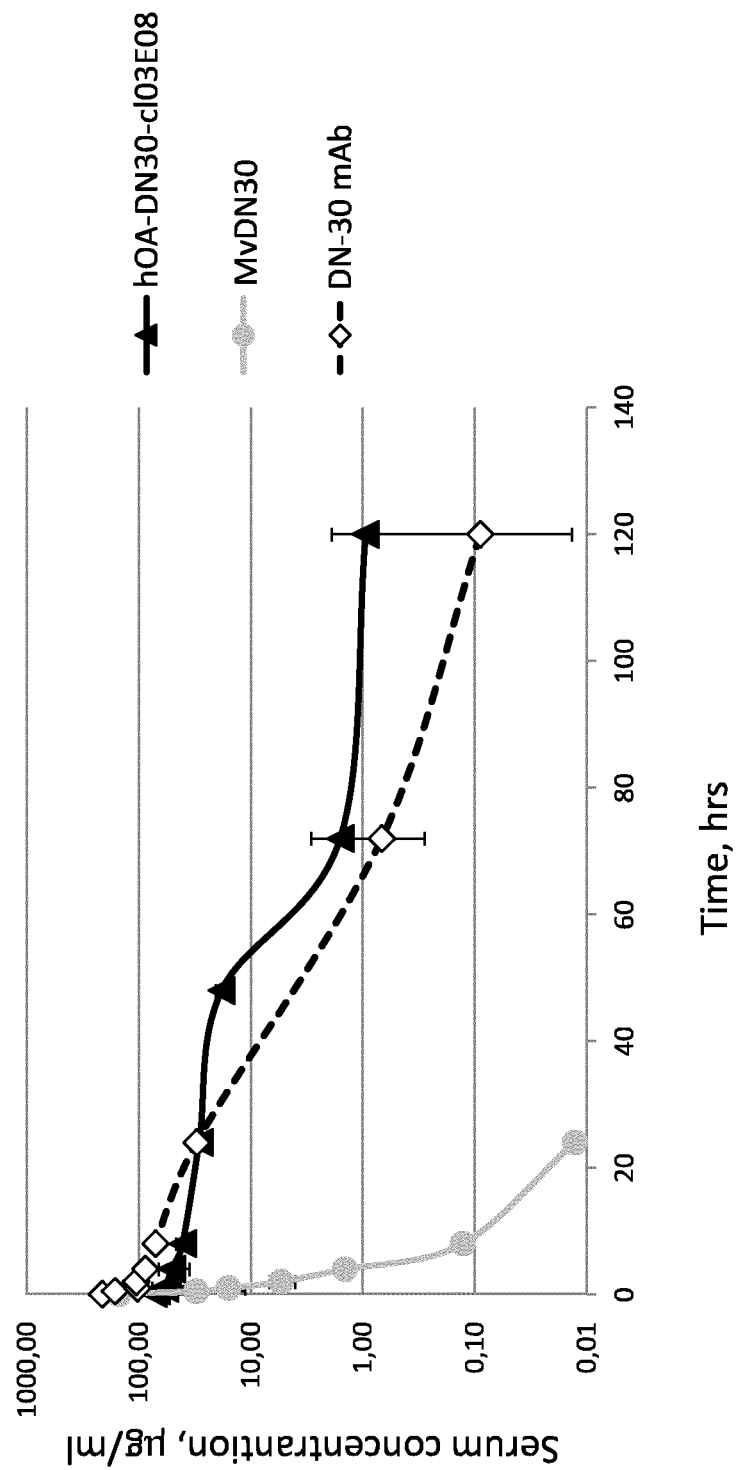
FIG. 11: Pharmacokinetic profile in vivo of MvDN30, DN30 mAb, and hOA-DN30-c103E08. Immuno-deficient mice were injected intravenously with a single dose (100 µg) of MvDN30, DN30 mAb, or hOA-DN30. Peripheral blood was collected at different time points. Serum concentrations of the therapeutic molecules were measured by ELISA. Graph represents the amount of circulating molecules as a function of time. Samples are in triplicate; bars represent standard deviations.
Figure 12:
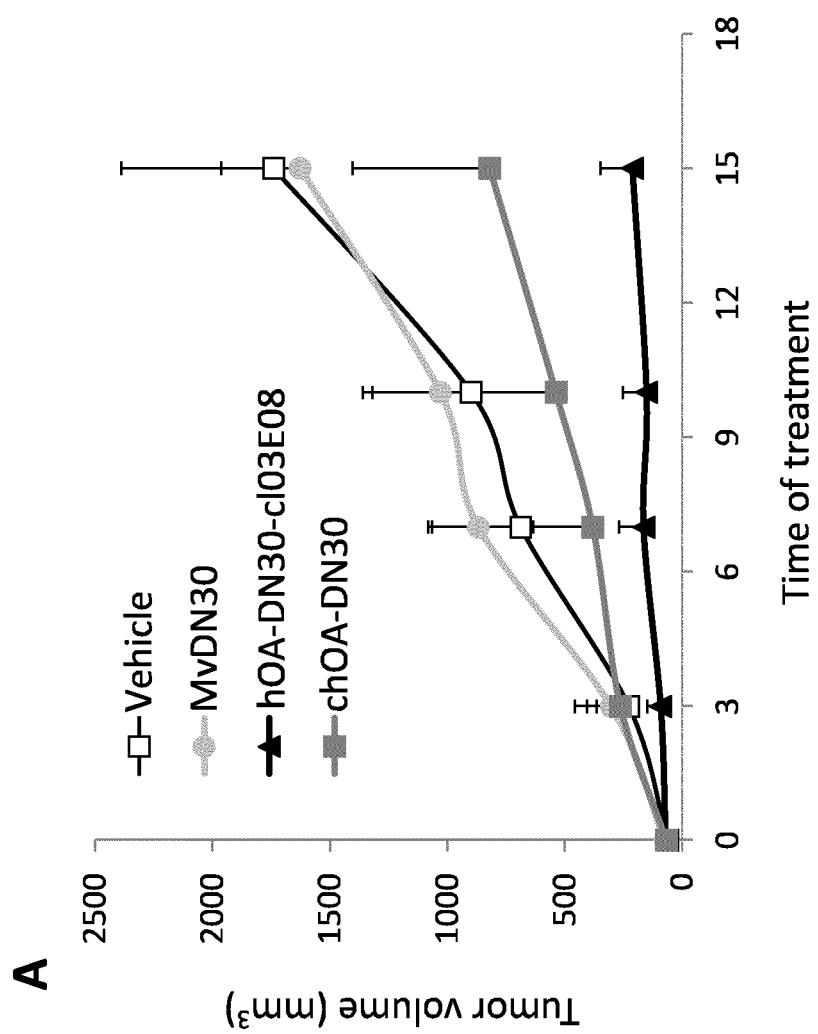
FIG. 12: Inhibition of MET-addicted tumor growth in vivo by treatment with the monovalent DN30 derivatives. $1\times10^6$ GTL-16 MET-addicted gastric carcinoma cells were inoculated in the flank of immune-deficient NOD-SCID mice. When the tumors reached an average volume of 68.4+5.4 mm$^3$, mice were randomized in 4 homogeneous groups and treated with 30 mg/kg of MvDN30, chOA-DN30, or hOA-DN30-c103E08 by intravenous injection 2 times per week. As a control, a group was treated with the same volume of PBS (Vehicle). Tumor growth was monitored periodically with a caliper. After 15 days, mice were sacrificed. (A) Kinetics of tumor growth; (B) Tumor volumes at the end of the experiment reported as percentage of the untreated group. hOA-DN30-c103E08 inhibits MET-addicted tumor growth more efficiently than the chOA-DN30.
Figure 13:
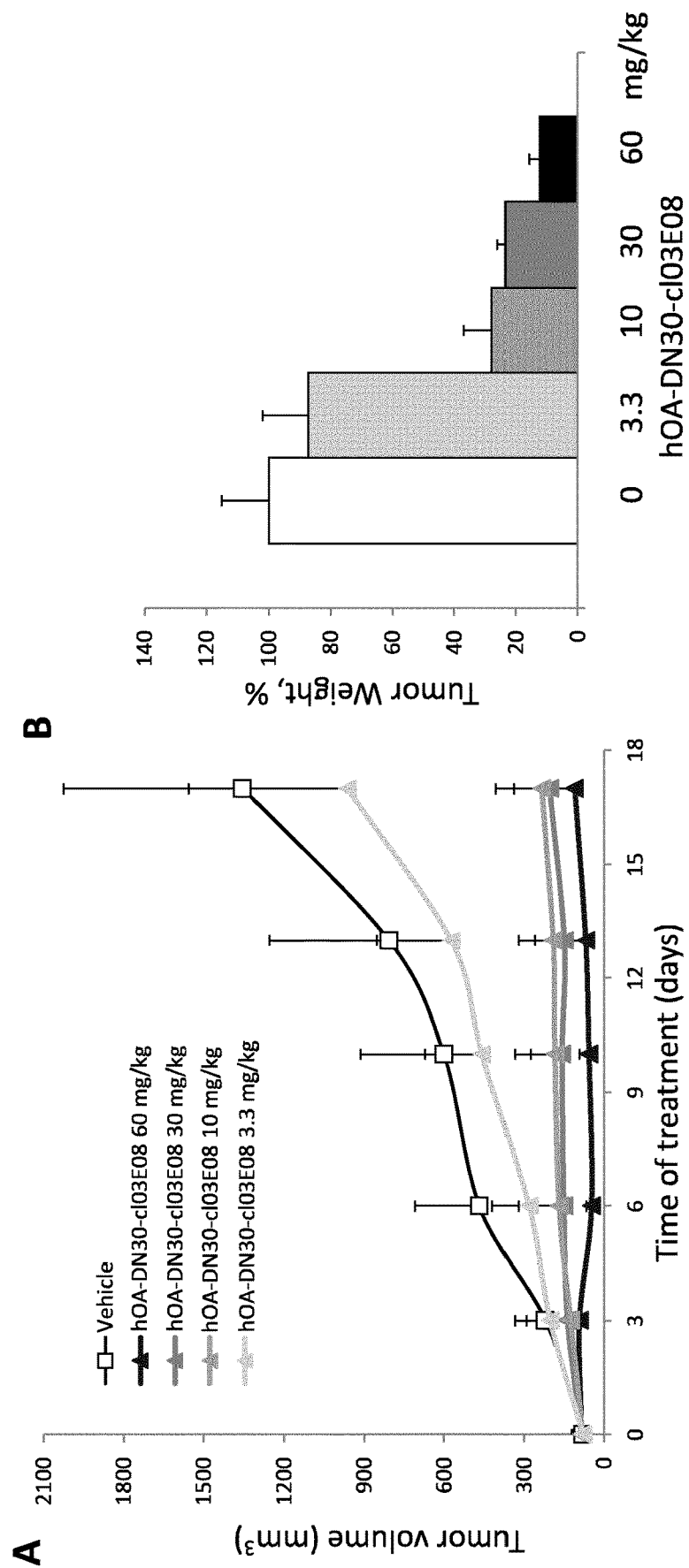
FIG. 13: Dose-response inhibition of MET-addicted tumor growth in vivo by hOA-DN30-c103E08 treatment. $1\times10^6$ GTL-16 MET-addicted gastric carcinoma cells were inoculated in the flank of immunodeficient NOD-SCID mice. After 8 days, the tumors reached an average volume of 80.7+2 mm$^3$ and the mice were randomized in 5 homogeneous groups and treated with increasing concentrations of hOA-DN30-c103E08 by intravenous injection. As a control, a group was treated with the same volume of PBS (Vehicle). Tumor growth was monitored periodically with a caliper. After 17 days, mice were sacrificed, and the tumors were excised and weighted. (A) kinetics of tumor growth; (B) Tumor weights. hOA-DN30-c103E08 inhibits MET-addicted tumor growth with a dose-response profile.

The present inventors studied the pharmacokinetic properties of hOA-DN30-C103E08, in comparison with MvDN30 and the chimeric DN30 mAb. A single dose of the above mentioned molecules were delivered by intravenous injection to immunodeficient mice. Peripheral blood from the treated mice was collected at different time points after the delivery. The circulating concentrations of the studied molecules were determined by ELISA performed on serum samples. hOA-DN30-c103E08 circulating levels were comparable to the ones measured for the mAb, and always higher than MvDN30 (FIG. 11). shows a favorable pharmacokinetic hOA-DN30-c103E08 Impairs Growth of MET-Addicted Tumors In Vivo The ability of DN30-derivatives to inhibit tumor growth in vivo was tested on a MET-addicted model. 1×10$^6$ GTL-16 cells were sub-cutaneously injected in the flank of NOD-SCID mice. After 1 week, mice carrying palpable tumors in were randomized 4 homogenous treatment groups: Vehicle (n=6), MvDN30 (n=6), hOA-DN30-c103E08 (n=5), chOA-DN30 (n=5). Antibodies were delivered by intravenous injection twice/week at 30 mg/Kg; to administer the same amount of molecules, MvDN30 was delivered following the same schedule at 15 mg/kg, as the molecular weight of the One-arm antibodies are double with respect to MvDN30 (i.e. around 100 KDa for OA-DN30 formats and around 50 KDa for MvDN30). MvDN30 was not effective—as expected from its short plasma half-life—while both the One-Arm derivatives inhibited tumor growth (FIG. 12A) (P=0.0007 and 0.05 for hOA-DN30-c103E08 and for chOA-DN30 respectively versus vehicle). Surprisingly hOA-DN30-c103E08 was exceedingly more effective than chOA-DN30: the treated masses were, in the case of hOA-DN30-c103E08, 87.8% and, in the case of chOA-DN30, 52.9% smaller than controls (FIG. 12B) (P=0.009 for hOA-DN30-c103E08 versus chOA-DN30). The present inventors further analyzed the inhibitory activity of the hOA-DN30-c103E08 performing a dose response experiment. Maintaining the experimental conditions described above, mice were randomized in 5 homogenous groups and treated by i.v. injection three times/week with different doses of hOA-DN30-c103E08. Doses of 10, 30, and 60 mg/kg were highly effective in blocking tumor growth, while treatment with 3.3 mg/kg was not statistically different from controls (FIG. 13).

Material and Methods

Cell Culture

A549 human lung adenocarcinoma cells, HPAF-II human pancreatic adenocarcinoma cells, C2C12 mouse muscle myoblasts, H9C2 (2-1) rat cardiac myoblasts, MDCK dog kidney cells, and Cos-7 monkey kidney cells were obtained from ATCC/LGC Standards S.r.l. (Sesto San Giovanni, Italy); GTL-16 cell line is a clone derived from MKN-45 cells (human gastric carcinoma cells available by the Japanese Collection of Research Bioresources, Osaka, Japan) that differs in MET gene copy number from the parental cell line[32]. GTL-16 cell line is available by Advanced Biotechnology Center (ABC), Interlab Cell Line Collection (ICLC) Italy, with accession number ICLC PD 08003. EBC-1, human lung from Japanese Collection of Research cancer, were Bioresources). DN30 hybridoma is available by Advanced Biotechnology Center (ABC), Interlab Cell Line Collection (ICLC) Italy, with accession number ICLC PD 05006.

All the cells were cultured as suggested by the supplier. All cell cultures were tested for *mycoplasma* contamination.

Generation of the Chimeric and Human One-Arm Form of the DN30 Antibody.

For the chimeric DN30 antibody: three separate CDNAs encoding respectively the light chain (VL-CL), the heavy chain (VH-CH1-cH2-CH3), and the Fc domain (CH2-CH3) have been generated by gene synthesis. Variable regions (mouse sequences) were from the DN30 antibody (SEQ ID: 15 and 16); constant regions of human origin derived from human immunoglobulins, in particular the light chain includes the human kappa type constant domain (GenBank sequence ID #: DI165992), and the heavy chain includes the human IgG1 constant domains (GenBank sequence ID #: DJ392898). At the C-terminus of the encoding sequences, the heavy chain includes a His-TAG (SEQ ID: 38, 39) and the Fc includes a strep-TAG (SEQ ID: 40, 41).

For the humanized DN30 antibody: Humanization by germ line screening of the DN30 mouse antibody has been done by Fair Journey Biologics using a phage display library approach. They started from the identification of deviating FR (frame) residues and the analysis of the closest human V germline, chosen from germlines with identical canonical fold combination for CDR1-CDR2, using available tools and databases: abYsistool from Dr. Andrew Martin at UCL plus, http://www.bioc.uzh.ch/plueckthun/antibody/and http://www2.mrc-lmb.cam.ac.uk/vbase/. Upon generation of phage display libraries—in which randomization of the VH and VL region has been performed—four affinity-driven phage display rounds of selection have been done. At the end of the process, five different DN30 humanized variants with the highest human identity and homology were selected, namely clones 03E08, 03G05, 03F04, 03H08 and 04H08. Variable regions were linked through classical molecular biology techniques to the constant domain derived human sequences from immunoglobulins, i.e. human kappa light chain and IgG1 heavy chain constant domains.

For formatting the chimeric and the humanized antibodies into the One-Arm form (chOA-DN30 and hOA-DN30 antibodies): specific amino acid modifications have been inserted in the CH3 region to produce the 'knob into hole' structure[28,29]. 'Knobs-into-holes' was demonstrated to be an effective design strategy for enhancing the formation of heterodimers over homodimers. The strategy is based on the domain interface remodeling, introducing sterically complementary mutations in the CH3 region of the antibody Fc fragment, the most extensive site of protein-protein interaction between the H chains of human IgG molecules. One chain, the VH-CH1-CH2-CH3 polypeptide, includes the $^{389}T\rightarrow W$ (Knob mutation), in which a small amino acid is substituted by a larger one; conversely, the other chain, the CH2-CH3 polypeptide, includes the replacement of large residues with smaller ones: $^{389}T\rightarrow S$; $^{391}L\rightarrow A$; $^{438}Y\rightarrow V$ (Hole mutations). These mutations were selected upon optimization by phage display technology[33], in which residues 389, 391 and 438, that are in proximity to the knob on the partner CH3 domain, were randomly substituted. Knobs-into-holes engineering facilitates the assembly of a heterodimer, including the three different amino acid chains (VL-CL+VH-CH1-CH2-CH3+CH2-CH3) in place of homodimers i.e. the bona fide antibody (VL-CL+VH-CH1-CH2-CH3) 2 or the Fc domain only (CH2-CH3) 2.

At the N-terminal, the CH2-CH3 polypeptide includes a sequence corresponding to a truncated human Hinge region. The deletion is necessary to exclude the cysteine at position 233 according to the EU numbering scheme of Kabat that is involved in the formation of an inter-chain disulfide bond with the cysteine at the C-terminal position of the light chain constant domain (CL). Moreover, to allow the CH2-CH3 polypeptide to enter the RER/Golgi pathway of protein synthesis—as light (VL-CL) and heavy chains (VH-CH1-CH2-CH3) of the antibody do—at the N-terminus, before the truncated Hinge region, a sequence corresponding to the signal peptide of the DN30 Heavy chain is included.

The chimeric anti-Met antibody fragment (chOA-DN30) disclosed herein is made of:
(i) a light chain variable domain having the amino acid sequence set forth in SEQ ID No.: 15; variable domain having the
(ii) a heavy chain amino acid sequence set forth in SEQ ID No.: 16;
(iii) a human light chain constant (CL) domain having the amino acid sequence set forth in SEQ ID No.: 9;
(iv) a human heavy chain constant CH1 domain having the amino acid sequence set forth in SEQ ID No.:
(v) a first human Fc polypeptide having the amino acid sequence set forth in SEQ ID No.: 11; and
(vi) a second human Fc polypeptide having the amino acid sequence set forth in SEQ ID No.: 12.

The humanized anti-Met antibody fragment (hOA-DN30-c103E08) object of the present disclosure is made of:
(i) a humanized light chain variable domain having the amino acid sequence set forth in SEQ ID No.: 7;
(ii) a humanized heavy chain variable domain having the amino acid sequence set forth in SEQ ID No.: 8;
(iii) a human light chain constant (CL) domain having the amino acid sequence set forth in SEQ ID No.: 9;
(iv) a human heavy chain constant CH1 domain having the amino acid sequence set forth in SEQ ID No.: 10;
(v) a first human Fc polypeptide having the amino acid sequence set forth in SEQ ID No.: 11; and
(vi) a second human Fc polypeptide having the amino acid sequence set forth in SEQ ID No.: 12.

The humanized anti-Met antibody fragment (hOA-DN30-c103G05) is made of:
(i) a humanized light chain variable domain having the amino acid sequence set forth in SEQ ID No.: 17;
(ii) a humanized heavy chain variable domain having the amino acid sequence set forth in SEQ ID No.: 18;
(iii) a human light chain constant (CL) domain having the amino acid sequence set forth in SEQ ID No.: 9;
(iv) a human heavy chain constant CH1 domain having the amino acid sequence set forth in SEQ ID No.: 10;
(v) a first human Fc polypeptide having the amino acid sequence set forth in SEQ ID No.: 11; and
(vi) a second human Fc polypeptide having the amino acid sequence set forth in SEQ ID No.: 12.

The humanized anti-Met antibody fragment (hOA-DN30-c103F04) is made of:
(i) a humanized light chain variable domain having the amino acid sequence set forth in SEQ ID No.: 19;
(ii) a humanized heavy chain variable domain having the amino acid sequence set forth in SEQ ID No.: 20;
(iii) a human light chain constant (CL) domain having the amino acid sequence set forth in SEQ ID No.: 9;
(iv) a human heavy chain constant CH1 domain having the amino acid sequence set forth in SEQ ID No.: 10;
(v) a first human Fc polypeptide having the amino acid sequence set forth in SEQ ID No.: 11; and
(vi) a second human Fc polypeptide having the amino acid sequence set forth in SEQ ID No.: 12.

The humanized anti-Met antibody fragment (hOA-DN30-c103H08) object of the present disclosure is made of:
(i) a humanized light chain variable domain having the amino acid sequence set forth in SEQ ID No.: 21;
(ii) a humanized heavy chain variable domain having the amino acid sequence set forth in SEQ ID No.: 22;
(iii) a human light chain constant (CL) domain having the amino acid sequence set forth in SEQ ID No.: 9;
(iv) a human heavy chain constant CH1 domain having the amino acid sequence set forth in SEQ ID No.: 10;
(v) a first human Fc polypeptide having the amino acid sequence set forth in SEQ ID No.: 11; and
(vi) a second human Fc polypeptide having the amino acid sequence set forth in SEQ ID No.: 12.

The humanized anti-Met antibody fragment (hOA-DN30-c104H08) object of the present disclosure is made of:
(i) a humanized light chain variable domain having the amino acid sequence set forth in SEQ ID No.: 23;
(ii) a humanized heavy chain variable domain having the amino acid sequence set forth in SEQ ID No.: 24;
(iii) a human light chain constant (CL) domain having the amino acid sequence set forth in SEQ ID No.: 9;
(iv) a human heavy chain constant CH1 domain having the amino acid sequence set forth in SEQ ID No.: 10;
(v) a first human Fc polypeptide having the amino acid sequence set forth in SEQ ID No.: 11; and
(vi) a second human Fc polypeptide having the amino acid sequence set forth in SEQ ID No.: 12.

Expression and Purification of Chimeric and Human One Arm Antibodies

The CDNAs encoding the above described light chains (nucleotide sequence set forth in SEQ ID No.: 25, 26, 27, 28, 29 for the humanized light chains and SEQ ID No.: 30 for the chimeric light chain), heavy chains (nucleotide sequence set forth in SEQ ID No.: 31, 32, 33, 34, 35 for the humanized heavy chain and SEQ ID No.: 36 for the chimeric heavy chain) and Fc (nucleotide sequence set forth in SEQ ID No.: 37) were cloned into commonly available expression vectors (e.g. pcDNA3.1 plasmids cat. #V79020 Invitrogen Corporation, Camarillo, CA) and used to transfect ExpiCHO-S cells (cat. #: A29127, ThermoFisher Scientific). The vector ratio was optimized to maximize the output of the (the desired 97.5 kDa heterodimer OA-Ab) and to minimize the presence of any 150 kDa bivalent homodimer (bona fide Mab). The optimal ratio 1:2 was: 1: respectively for Light chain, Heavy chain full size ("knob" vector) and Fc ("hole" vector). This condition resulted in the least amount of homodimer present, with the heterodimer being approximately 85% of the total protein. Transient expression was powered by ExpiFectamine™ CHO transfection reagent (cat. #A29130, ThermoFisher Scientific). Supernatants were harvested after 9 days of production. The OA-DN30 antibodies were purified using a Hitrap MabSelect Sure column (cat. #GE29-0491-04, Sigma Aldrich) on an ÄKTA Pure 25 antibodies were chromatography system. The OA-DN30 subsequently eluted using 0.1 M citrate buffer at pH 3.0. Eluted fractions were collected and neutralized with 1M Tris-HCl pH 9.0 (at a ratio of 0.15 ml per ml of eluted protein). The OA-DN30 antibodies were further purified on a 1× PBS (pH 7.4)-equilibrated Superdex 200 26/600 size exclusion column (cat. #GE28-9893-36, Sigma Aldrich) on a GE AKTA Prime Liquid Chromatography System (GE Healthcare Life Sciences), where fractions containing the OA-Ab were separated from homodimeric fractions (mAb or Fc). Preparative SEC fractions containing the OA-DN30 antibodies were pooled and analyzed by SDS-PAGE to ascertain the purity. The pooled fractions were also tested for endotoxin levels. The final pooled fractions from the preparative SEC purifications, showing the absence of any bivalent homodimer, and the presence of a small amount (<5%) of a smaller=70 kDa band, which corresponds to the Knob-Knob Fc homodimer.

Generation, Expression, and Purification of Mutated Met Ectodomain

CDNA sequence of human MET ectodomain (DecoyMet) carrying a single amino acid substitution was synthetically generated starting from the human Met ectodomain sequence as disclosed in GenBank at deposit number X54559, and using the QuickChange II Site-Directed Mutagenesis Kit (cat. #200524 Agilent Technologies, Santa Clara, CA), following the instruction of the manufacturer. The procedure requires the design of sense and antisense oligonucleotides, that include the desired point mutation. The following oligos has been employed:

```
mutation K842E:
                                    (SEQ ID No.: 42)
sn. 5'-gtacataatcctgtgtttgagccttttgaaaagccagtg-3';

(SEQ ID No.: 43)
as. 5'-cactggcttttcaaaaggctcaaacacaggattatgtac-3'.
```

Engineered soluble receptor was produced by transient transfection of HEK-293T cells with pcDNA3.1 plasmids (cat. #V79020 Invitrogen Corporation, Camarillo, CA) expressing cDNA encoding for DecoyMet mutant. Transfected cells were starved for three days and cell culture supernatants containing the soluble receptor were collected. Purification of the recombinant proteins was done by affinity chromatography using HisTrap HP columns (cat. #17524701 GE Healthcare, Freiburg, Germany) according to manufacturer's instructions. Large-scale protein production and purification was performed by U-Protein Express BV (Utrecht, The Netherlands).

The variant of human DecoyMet (DecoyMETK842E) has the amino acid sequences set forth in SEQ ID No.: 14.

Analysis of the Purified Proteins by SDS-PAGE+Blue Coomassie

Purified OA-DN30 antibodies (1 μg) were separated into a 4-12% acrylamide gradient gel by SDS-PAGE in the presence in the absence of B-mercapto ethanol following standard methods. Molecular weight markers (cat. #1610374, Bio-Rad) were included in the analysis. Polypeptides separated into the gel were revealed by Gel Code Blue Stain reagent (cat. #24590, Thermo Fisher Scientific).

ELISA Binding Assays

For analysis of the interaction between Met and the DN30 derivatives, purified Met-Fc chimeras (cat #. 358-MT-100 R&D Systems, 100 ng/well) were immobilized on ELISA plates. After saturation with 0.5% BSA incubated 1 hr at 37° C., increasing concentrations of the antibodies (MvDN30, chOA-DN30 or hOA-DN30 antibodies, 0-500 nM prepared in PBS-BSA 0.5%-Tween 0.1%)) were added in liquid phase. Binding was revealed using HRP-conjugated anti-human k chain antibody (cat. #A7164, Sigma-Aldrich) followed by incubation with TMB (cat. #T8665, Sigma Aldrich). Colorimetric assay was quantified by the multi-label plate reader VICTOR-X4 (Perkin Elmer Instruments INC., Whaltman, MA). Data were analyzed and fit using Prism software (GraphPad).

For ELISA binding analysis of hOA-DN30-c103E08 (liquid phase) to Met-Fc chimera (solid phase) derived from different species, Met of human (cat #. 358-MT-100 R&D Systems), murine Sino (cat. #50622-M02H, Biological), rat (cat. #80004-R02H, Sino Biological), and monkey (cat. #90304-C02H, Sino Biological) origin were included in the assay. The procedure was same as the one described above.

Flow-Cytometer Binding Analysis

For hOA-DN30-c103E08 binding to Met expressed at the surface of cells, $2 \times 10^5$ EBC-1, C2C12, H9C2, MDCK, or Cos-7 cells were treated with StemPro™ Accutase™ Cell Dissociation Reagent (cat. #A1110501, ThermoFisher Scientific) collected and incubated for 1 hour at 4° C. in PBS-2% FCS. Antibody staining was performed by incubating the cells for 30 min at 4° C. with 10 μg/ml of hOA-DN30-c103E08 in PBS-2% BSA. After 6 washes with PBS-2% BSA, cells were incubated with anti-human IgG-APC (cat. #109-606-088 Jackson Immuno Research) diluted 1:100 for 30 min al 4° C. and then washed to removed unbound antibodies. Cells were co-stained with DAPI (3 μl of 1 μg/ml working solution, Sigma-Aldrich, cat. #10236276001) for 5 min at 4° C. and analyzed for Met expression by Summit 4.3 software (Dako). The fluorescence signal derived from the isotype control (anti human APC IgG) was set as a threshold (0<MFI<101). Cells were considered positive for Met expression if the Mean Fluorescence Intensity (MFI) was higher than the threshold (MFI>101).

Analysis of Met Shedding

Sub-confluent A549 monolayers were washed twice with PBS and then incubated in serum-free medium with increasing concentrations (37, 111, 333, 1000 nM) of DN-30 derivatives. After 48 hours, conditioned medium was collected and cells were lysed with Laemmli Buffer. Met protein levels were determined in 15 μg of total cellular proteins by Western blot using anti-Met antibodies (3D4, cat. #08-1366 Invitrogen Corporation); as a loading control, filters were probed also with anti-vinculin antibodies (clone hVIN-1, cat. #V9131 Sigma Life Science). Met ectodomain levels were determined in 15 μl of cell culture supernatant by Western blotting using an anti-human HGFR/Met antibody directed against the extracellular domain of the receptor (cat. #AF276, R&D Systems). Anti-mouse IgG1 HRP-conjugated secondary antibodies (cat. #JI115035003, Jackson ImmunoResearch) and the ECL System (cat. #W1015, Promega,) were used for protein detection. Western Blot bands were quantified using ImageJ software.

MET Phosphorylation Assays

Serum-starved GTL-16 cells were incubated for 24 h with DN30 derivatives (1000 or 250 nM). Total cellular lysates were analyzed by Western blot using the following primary antibodies: anti-Met phospho-Tyr1234/1235 (D26, cat. #3077 Cell Signaling Technology); anti-Met (3D4, cat. #08-1366 Invitrogen Corporation); and anti-vinculin (clone hVIN-1, cat. #V9131 Sigma Life Science). Anti-mouse IgG1 and anti-rabbit IgG (cat. #JI111035003) HRP-conjugated secondary antibodies and the ECL System were used for protein detection. Western Blot bands were quantified using ImageJ software.

In Vitro Biological Assays

For cell scattering assays, HPAF-II cells (8000/well) were seeded in 96-well plates in complete culture medium. To analyze the agonistic activity of the antibodies, after 24 hrs, HGF (8 ng/ml, positive control, cat. #294-HG-025, R & D Systems) or the antibodies (DN30 mAb, MvDN30, chOA-DN30, hOA-DN30 antibodies, all at the concentration of 200 nM), were added to the culture medium. To analyze the inhibitory activity, increasing concentrations (0-4 µM) of hOA-DN30-c103E08, alone or in 1:1 combination with DecoyMetK842E, were added. After an additional time of 24 hrs, cells were stimulated with 6.25 ng/ml HGF for 24 hrs. Cells were then fixed with 11% glutaraldehyde (cat. #340855 Sigma-Aldrich), stained with 0.1% Crystal Violet (cat. #C3886 Sigma-Aldrich) and analyzed by microscope observation (Microscope Leica DM2000). Images were captured with QICAM Fast 1394 color digital Camera (QImaging).

For cell invasion assays, HPAF-II cells ($1.5 \times 10^5$/well) were suspended in serum-free culture medium in the presence of 0.5 µM hOA-DN30-c103E08 alone or in combination with 1 µM DecoyMetK842E, and seeded on the upper compartment of transwell chambers pre-coated with 30 µg/well of Matrigel Matrix (cat. #354234, Corning Inc.). Culture medium supplemented with 2% FBS and 6.25 ng/ml HGF was added to the lower compartment of the chambers. After 24 hrs, cells on the upper side of the transwell filters were mechanically removed, while cells migrated through the membrane were fixed with 11% glutaraldehyde and stained with 0.1% Crystal Violet. Cell invasion was quantified with Image-J software.

For vitality assay, GTL-16 cells were seeded 2000 cells/well in a 96 well plate in 10% FBS culture medium. After 24 hrs, medium was replaced with a fresh one with 10% FBS plus the molecules to be tested (increasing concentrations—from 0 to 10 µM). Cell after 72 hrs using the viability was evaluated CellTiter-Glo (cat. #G7573 Promega Corp), according to the manufacturer's instructions. Chemo-luminescence was detected with VICTOR X4.

For proliferation assay, 350000 GTL-16 cells were plated in 6 well plates in 10% FCS medium. After 24 hrs, cells were treated with a fixed concentration (1 µM) of DN30 derivatives for further 48 hrs. Then, 10 UM EdU (cat. #A10044, Thermo Fisher) was added to the culture medium for a further 2 hrs. The % of cells in S phase was determined by cytofluorimeter analysis following the procedure of the Click-iT™ EdU Alexa Fluor™ 488 Flow Cytometry Assay (cat. #C10425, Thermo Fisher).

For cytotoxicity assay, 2000 GTL-16 cells were plated in 96 well plates in 10% FCS medium. After 24 hrs, cells were treated with increasing concentrations of the DN30 derivatives for a further 48 hrs. Cell cytotoxicity was evaluated by Cell-Tox™ Green cytotoxicity assay (cat. #G8741, Promega) following manufacturer's instructions.

PD-L1 Expression Analysis

Sub-confluent GT1-16 cells were treated with 50 ng/ml of IFNγ-1b (Miltenyi Biotec, cat. #130-096-484) for 48 hours (replaced every 24 hours) in combination with 250 nM hOA-DN30-c103E08. Monolayers were then lysed in Laemmli buffer and 45 µg of total proteins were subjected to 8% SDS-PAGE gel. Proteins were transferred from the gel onto iBlot Transfer nitrocellulose membranes (Life technologies, cat. #IB23001) following standard methods. PD-L1 expression s detected by anti-PD-L1 antibody (E1L3N, cat. #13684, Cell Signaling Technology). P-Met levels were checked by anti-MET phospho-Tyr1234/1235 (D26) antibodies. As loading control, filters were probed with anti-GAPDH (D4C6R, cat. #97166 Cell Signaling Technology). Secondary HRP-conjugated goat anti-mouse IgG (cat. #JI115035003) or anti-rabbit IgG (cat. #JI111035144) (both from Jackson ImmunoResearch) and the ECL System were used for protein detection.

In Vivo Experiments

All animal procedures were performed according to protocols approved by Ethical Committee for animal experimentation of the Fondazione Piemontese per 1a Ricerca sul Cancro and by Italian Ministry of Health. NOD-SCID mice were purchased from Charles River (Calco, Italy).

For pharmacokinetic analysis NOD-SCID mice were injected intravenously with a single dose (100 µg) of hOA-DN30-c103E08. Peripheral blood was collected at different time points: 10', 30', 1 hr, 4 hrs, 8 hrs, 24 hrs, 48 hrs, 72 hrs, 120 hrs. Serum concentrations of the therapeutic molecules were measured by ELISA as described above in the binding assay section, interpolating the absorbance values of the samples on the linear part of a standard curve obtained by serial dilutions of the different purified molecules. Each time point was the average value of 4 mice.

For tumor growth analysis $1 \times 10^6$ GTL-16 cells were inoculated in the flank of NOD-SCID mice. Tumor growth was monitored by caliper measurement twice weekly. Tumor volume was calculated using the formula: $V = 4/3 \pi (x/2)(y/2)(z/2)$, where x, y and z are height, width and depth of the tumor mass. When the tumors reached a volume of 70-100 mm³ (approximately one week after cell injection) mice were randomized in homogeneous groups. In one case, groups were generated (PBS-vehicle, MvDN30, chOA-DN30, hOA-DN30-c103E08; all the antibodies 30 mg/kg, 2 times per week); in the other case, 5 groups were generated (PBS-vehicle, hOA-DN30-c103E08 60 mg/kg, 30 mg/kg, 10 mg/kg, 3.3 mg/kg; all the doses 3 times per week). Molecules were administered by intravenous injection. At the end of the experiments (15 or 17 days of treatment) mice were sacrificed, tumors were excised and weighted.

Statistical Analysis

Average and standard deviation (SD) were calculated using Microsoft Office Excel 2010 software (Microsoft Corporation). To calculate $K_d$ values, data from ELISA assays were analyzed and fitted according to nonlinear regression, one site binding hyperbola curve, using GraphPad Prism software (GraphPad Software). To calculate $IC_{50}$ and $EC_{50}$ values, data were analyzed and fitted according to nonlinear regression, sigmoidal dose-response curve, using GraphPad Prism software. All experiments were repeated at least two times. Figures show one representative experiment.

REFERENCES

1. Comoglio PM, Trusolino L, Boccaccio C. Known and novel roles of the MET oncogene in cancer: a coherent approach to targeted therapy. Nat Rev Cancer 2018; 18 (6): 341-358; doi 10.1038/s41568-018-0002-y.
2. Kong-Beltran M, Seshagiri S, Zha J, Zhu W, Bhawe K, Mendoza N et al. Somatic mutations lead to an oncogenic deletion of met in lung cancer. Cancer Res 2006; 66 (1): 283-289; doi 10.1158/0008-5472.CAN-05-2749.
3. Gandino L, Longati P, Medico E, Prat M, Comoglio PM. Phosphorylation of serine 985 negatively regulates the hepatocyte growth factor receptor kinase. J Biol Chem 1994; 269 (3): 1815-1820.
4. Petrelli A, Gilestro GF, Lanzardo S, Comoglio PM, Migone N, Giordano s. The endophilin-CIN85-Cbl complex mediates ligand-dependent downregulation of c-Met. Nature 2002; 416 (6877): 187-190; doi 10.1038/416187a.
5. Trusolino L, Bertotti A, Comoglio PM. MET signalling: principles and functions in development, organ regeneration and cancer. Nat Rev Mol Cell Biol 2010; 11 (12): 834-848; doi 10.1038/nrm3012.
6. Prat M, Crepaldi T, Pennacchietti S, Bussolino F, Comoglio PM. Agonistic monoclonal antibodies against the Met receptor dissect the biological responses to HGF. J Cell Sci 1998; 111 (Pt 2): 237-247.
7. Pacchiana G, Chiriaco C, Stella MC, Petronzelli F, De Santis R, Galluzzo M et al. Monovalency unleashes the full therapeutic potential of the DN-30 anti-Met antibody. J Biol Chem 2010; 285 (46): 36149-36157; e-pub ahead of print 2010-9-10; doi 10.1074/jbc.M110.134031.
8. Cignetto S, Modica C, Chiriaco C, Fontani L, Milla P, Michieli P et al. Dual Constant Domain-Fab: A novel strategy to improve half-life and potency of a Met therapeutic antibody. Mol Oncol 2016; 10 (6): 938-948; e-pub ahead of print 2016-3-28; doi 10.1016/j.molonc.2016.03.004.
9. Wang Q, Yang S, Wang K, Sun SY. MET inhibitors for targeted therapy of EGFR TKI-resistant lung cancer. J Hematol Oncol 2019; 12 (1): 63; e-pub ahead of print 2019-6-21; doi 10.1186/s13045-019-0759-9.
10. Schelter F, Kobuch J, Moss ML, Becherer JD, Comoglio PM, Boccaccio C et al. A disintegrin and metalloproteinase-10 (ADAM-10) mediates DN30 antibody-induced shedding of the met surface receptor. J Biol Chem 2010; 285 (34): 26335-26340; doi 10.1074/jbc.M110.106435.
11. Foveau B, Ancot F, Leroy C, Petrelli A, Reiss K, Vingtdeux V et al. Down-regulation of the met receptor tyrosine kinase by presenilin-dependent regulated intramembrane proteolysis. Mol Biol Cell 2009; 20 (9): 2495-2507; doi 10.1091/mbc.E08-09-0969.
12. Vigna E, Chiriaco C, Cignetto S, Fontani L, Basilico C, Petronzelli F et al. Inhibition of ligand-independent constitutive activation of the Met oncogenic receptor by the engineered chemically-modified antibody DN30. Mol Oncol 2015; 9 (9): 1760-1772; doi 10.1016/j.molonc.2015.05.007.
13. Jones PT, Dear PH, Foote J, Neuberger MS, Winter G. Replacing the complementarity-determining regions in a human antibody with those from a mouse. Nature 1986; 321 (6069): 522-525; doi 10.1038/321522a0.
14. Riechmann L, Clark M, Waldmann H, Winter G. Reshaping human antibodies for therapy. Nature 1988; 332 (6162): 323-327; doi 10.1038/332323a0.
15. Presta LG. Antibody engineering. Curr Opin Biotechnol 1992; 3 (4): 394-398.
16. Vaswani SK, Hamilton RG. Humanized antibodies as potential therapeutic drugs. Ann Allergy Asthma Immunol 1998; 81 (2): 105-115; quiz 115-106, 119; doi 10.1016/S1081-1206 (10) 62794-9.
17. Hurle MR, Gross M. Protein engineering techniques for antibody humanization. Curr Opin Biotechnol 1994; 5 (4): 428-433.
18. Harris WJ. Production of humanized monoclonal antibodies for in vivo imaging and therapy. Biochem Soc Trans 1995; 23 (4): 1035-1038.
19. Bloom JW, Madanat MS, Marriott D, Wong T, Chan SY. Intrachain disulfide bond in the core hinge region of human IgG4. Protein Sci 1997; 6 (2): 407-415; doi 10.1002/pro.5560060217.
20. Humphreys DP, Chapman AP, Reeks DG, Lang V, Stephens PE. Formation of dimeric Fabs in *Escherichia coli*: effect of hinge size and isotype, presence of interchain disulphide bond, Fab' expression levels, tail piece sequences and growth conditions. J Immunol Methods 1997; 209 (2): 193-202.
21. Ferracini R, Longati P, Naldini L, *Vigna* E, Comoglio PM. Identification of the major autophosphorylation site of the Met/hepatocyte growth factor receptor tyrosine kinase. J Biol Chem 1991; 266 (29): 19558-19564.
22. Ponzetto C, Bardelli A, Zhen Z, Maina F, dalla Zonca P, Giordano S et al. A multifunctional docking site mediates signaling and transformation by the hepatocyte growth factor/scatter factor receptor family. Cell 1994; 77 (2): 261-271.
23. Gherardi E, Love CA, Esnouf RM, Jones EY. The sema domain. Curr Opin Struct Biol 2004; 14 (6): 669-678; doi 10.1016/j.sbi.2004.10.010 . . .
24. Bork P, Doerks T, Springer TA, Snel B. Domains in plexins: links to integrins and transcription factors. Trends Biochem Sci 1999; 24 (7): 261-263.
25. Merchant M, Ma X, Maun HR, Zheng Z, Peng J, Romero M et al. Monovalent antibody design and mechanism of action of onartuzumab, a MET antagonist with anti-tumor activity as a therapeutic agent. Proc Natl Acad Sci USA 2013; 110 (32): E2987-2996; doi 10.1073/pnas.1302725110.
26. Makabe K, Nakanishi T, Tsumoto K, Tanaka Y, Kondo H, Umetsu M et al. Thermodynamic consequences of mutations in vernier zone residues of a humanized anti-human epidermal growth factor receptor murine antibody, 528. J Biol Chem 2008; 283 (2): 1156-1166; e-pub ahead of print 2007-10-17; doi 10.1074/jbc.M706190200.
27. Basilico C, Modica C, Maione F, *Vigna* E, Comoglio PM. Targeting the MET oncogene by concomitant inhibition of receptor and ligand via an antibody-"decoy" strategy. Int J Cancer 2018; e-pub ahead of print 2018-4-25; doi 10.1002/ijc.31550.
28. Ridgway JB, Presta LG, Carter P. 'Knobs-into-holes' engineering of antibody CH3 domains for heavy chain heterodimerization. Protein Eng 1996; 9 (7): 617-621.
29. Zhu Z, Presta LG, Zapata G, Carter P. Remodeling domain interfaces to enhance heterodimer formation. Protein Sci 1997; 6 (4): 781-788; doi 10.1002/pro.5560060404.
30. Zou W, Chen L. Inhibitory B7-family molecules in the tumour microenvironment. Nat Rev Immunol 2008; 8 (6): 467-477; doi 10.1038/nri2326.

31. Garcia-Diaz A, Shin DS, Moreno BH, Saco J, Escuin-Ordinas H, Rodriguez GA et al. Interferon Receptor Signaling Pathways Regulating PD-L1 and PD-L2 Expression. Cell Rep 2017; 19 (6): 1189-1201; doi 10.1016/j.celrep.2017.04.031.

32 Rege-Cambrin G, Scaravaglio P, Carozzi F, Giordano S, Ponzetto C, Comoglio PM et al. Karyotypic analysis of gastric carcinoma cell lines carrying an amplified c-met oncogene. Cancer Genet Cytogenet 1992; 64 (2): 170-173.

33. Atwell S, Ridgway JB, Wells JA, Carter P. Stable heterodimers from remodeling the domain interface of a homodimer using a phage display library. J Mol Biol 1997; 270 (1): 26-35; doi 10.1006/jmbi.1997.1116.

The invention claimed is:

1. An anti-Met antibody fragment comprising a single antigen binding arm and an Fc region, wherein the anti-Met antibody fragment comprises:
   a) a first polypeptide comprising in the N terminal to C terminal direction a light chain variable domain (VL) and a human light chain constant domain (CL), wherein the VL comprises the amino acid sequence of residues 21-131 of SEQ ID NO: 7 and the CL comprises the amino acid sequence of SEQ ID NO: 9;
   b) a second polypeptide comprising in the N terminal to C terminal direction a heavy chain variable domain (VH), a human heavy chain constant domain 1 (CH1) and a first Fc domain, wherein the VH comprises the amino acid sequence of residues 20-131 of SEQ ID NO: 8, the CH1 comprises the amino acid of SEQ ID NO: 10, and the first Fc domain comprises the amino acid of SEQ ID NO: 11; and
   c) a third polypeptide comprising a second Fc domain comprising the amino acid sequence of residues 20-246 of SEQ ID NO: 12.

2. An anti-Met antibody fragment comprising a single antigen binding arm and an Fc region, wherein the anti-Met antibody fragment comprises a first polypeptide, a second polypeptide and a third polypeptide comprising the amino acid sequence of the mature polypeptide encoded by the nucleotide sequence of SEQ ID NO:
   25, 31, and 37, respectively, when the nucleotide sequence is expressed in a CHO cell.

3. A pharmaceutical composition comprising the anti-Met antibody fragment of claim 1 and a pharmaceutically acceptable vehicle.

4. A pharmaceutical composition comprising the anti-Met antibody fragment of claim 2 and a pharmaceutically acceptable vehicle.

5. An isolated nucleic acid encoding the anti-Met antibody fragment of claim 1.

6. An isolated nucleic acid encoding the anti-Met antibody fragment of claim 2.

7. A mammalian host cell comprising the isolated nucleic acid of claim 5.

8. A mammalian host cell comprising the isolated nucleic acid of claim 6.

9. A method of producing the anti-Met antibody fragment of claim 1 comprising (i) culturing a mammalian host cell comprising a nucleic acid encoding the anti-Met antibody fragment under suitable conditions to produce the anti-Met antibody fragment, and (ii) purifying the anti-Met antibody fragment.

10. A method of producing the anti-Met antibody fragment of claim 2 comprising (i) culturing a CHO host cell comprising a nucleic acid encoding the anti-Met antibody fragment under suitable conditions to produce the anti-Met antibody fragment and (ii) purifying the anti-Met antibody fragment.

* * * * *